United States Patent
Fan et al.

(10) Patent No.: US 12,331,061 B2
(45) Date of Patent: Jun. 17, 2025

(54) COMPOUNDS HAVING BET, ESTROGEN RECEPTOR, AND ANDROGEN RECEPTOR DEGRADATION ACTIVITY AND USES THEREOF

(71) Applicant: ACCUTAR BIOTECHNOLOGY INC., Brooklyn, NY (US)

(72) Inventors: Jie Fan, Brooklyn, NY (US); Wei He, Brooklyn, NY (US); Ke Liu, Brooklyn, IN (US)

(73) Assignee: Accutar Biotechnology Inc., Brooklyn, NY (US)

(*) Notice: Subject to any disclaimer, the term of this patent is extended or adjusted under 35 U.S.C. 154(b) by 830 days.

(21) Appl. No.: 17/604,014

(22) PCT Filed: Apr. 17, 2020

(86) PCT No.: PCT/US2020/028767
§ 371 (c)(1),
(2) Date: Oct. 15, 2021

(87) PCT Pub. No.: WO2020/214952
PCT Pub. Date: Oct. 22, 2020

(65) Prior Publication Data
US 2022/0220124 A1    Jul. 14, 2022

Related U.S. Application Data

(60) Provisional application No. 62/835,825, filed on Apr. 18, 2019.

(51) Int. Cl.
*C07D 495/14* (2006.01)
*C07D 211/88* (2006.01)
*C07D 401/12* (2006.01)
*C07D 401/14* (2006.01)

(52) U.S. Cl.
CPC .......... *C07D 495/14* (2013.01); *C07D 211/88* (2013.01); *C07D 401/12* (2013.01); *C07D 401/14* (2013.01)

(58) Field of Classification Search
CPC ............... C07D 495/14; C07D 211/88; C07D 401/12
See application file for complete search history.

(56) References Cited

U.S. PATENT DOCUMENTS

| | | | |
|---|---|---|---|
| 5,254,587 A | 10/1993 | Burzynski | |
| 11,802,131 B2 * | 10/2023 | Norcross | C07D 401/12 |
| 2018/0155322 A1 | 6/2018 | Crew et al. | |

OTHER PUBLICATIONS

International Search Report of International Application No. PCT/US2020/028767, mail date Aug. 14, 2020 (4 pages).
Pubchem, Substance Record for SID 354115955, Available Date: Jan. 29, 2018 [retrieved on Jul. 28, 2020]. Retrieved from the Internet: URL:https://pubchem.ncbi.nlm.nih.gov/substance/354115955.

* cited by examiner

*Primary Examiner* — Kamal A Saeed
(74) *Attorney, Agent, or Firm* — Finnegan, Henderson, Farabow, Garrett & Dunner, LLP

(57) ABSTRACT

Compounds, pharmaceutical compositions containing such compounds, and their use in prevention and treatment of cancer and other related diseases and conditions are disclosed. In an embodiment, the disclosed compounds have the following Formula (I) and pharmaceutically acceptable salts thereof:

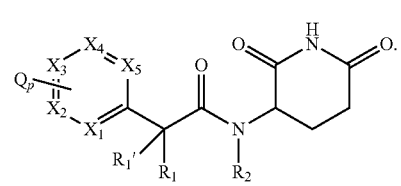

Formula (I)

36 Claims, 4 Drawing Sheets

COMPOUNDS HAVING BET, ESTROGEN RECEPTOR, AND ANDROGEN RECEPTOR DEGRADATION ACTIVITY AND USES THEREOF

CROSS-REFERENCE TO RELATED APPLICATION

This is a National Stage Application under 35 U.S.C. § 371 of International Patent Application No. PCT/US2020/028767, filed Apr. 17, 2020, which claims the benefit of priority of U.S. Provisional Patent Application No. 62/835,825, filed Apr. 18, 2019, both of which are incorporated herein by reference in their entirety.

FIELD OF THE DISCLOSURE

The present disclosure relates to novel compounds, pharmaceutical compositions containing such compounds, and their use in prevention and treatment of diseases and conditions, such as cancer.

BACKGROUND OF THE DISCLOSURE

Bromodomain (BRD) containing proteins play an important role in chromatin remodeling through interactions with post-translationally-modified histones. The BET family of proteins (BRD2, BRD3, BRD4, and BRDT) share a common domain architecture, featuring two amino-terminal bromodomains and a divergent carboxy-terminal recruitment domain, and can bind acetylated lysine residues in histones and other proteins. The BET family of proteins plays a critical role in cellular proliferation and cell cycle progression, and as a result, many small molecule BET inhibitors have been developed to treat uncontrolled cell growth. The potency of such direct inhibitors has been limited, however.

Estrogen, a female sex hormone that binds Estrogen receptors (ERs) ERα and ERβ, governs a wide range of physiological processes including the development of the female reproductive system, the maintenance of bone mass, and the protection of cardiovascular tissue and the central nervous system. Estrogen binding to ERα and ERβ triggers a conformational change in the receptor, resulting in receptor homodimerization. The ER homodimer then binds to estrogen-response elements (EREs) in the promoters of specific target genes and regulates their expression with the help of transcriptional coregulators. Several thousand canonical ER target genes have been identified, many of which regulate cellular proliferation and survival. Deregulation of ER signaling, specifically through ERα, is a well-established driver of uncontrolled cellular proliferation, and ultimately cancer. ER+ breast cancer accounts for approximately 75% of all breast cancers diagnosed, as well as some ovarian and endometrial cancers. Development of antiestrogens as therapeutic agents has been a decades-long investigation.

Antiestrogen (hormonal) therapy is the first treatment of choice for most ER+ breast cancer patients. Currently, three classes of antiestrogen therapies are widely used: 1) aromatase inhibitors, such as letrozole and anastrozole, which decrease estrogen production by inhibiting aromatase activity, thus suppressing circulating levels of estrogen, 2) selective estrogen modulators (SERM), such as tamoxifen, toremifene and raloxifene, which competitively bind ER and serve as antagonists in breast cells, and 3) selective estrogen receptor down regulators (SERDs), such as fulvestrant, which exhibit pure antagonism. SERDs competitively bind ER with high affinity, impair receptor dimerization and nuclear localization, and induce ER degradation through the ubiquitin-proteasome pathway.

Clear limitations have been observed with all three classes of therapies. Aromatase inhibitors decrease bone mineral density and increase risk of fracture. SERMs often display partial agonism, resulting in incomplete blockade of estrogen-mediated activity and potential toxicities in some tissues. Further, tamoxifen and toremifene increase the risk of developing endometrial cancer, and Raloxifene increases the incidence of blood clots, deep vein thrombosis, and pulmonary embolism. The SERD Fulvestrant has poor pharmacokinetic properties and downregulates ERα by only half after 6-months of treatment. Most importantly, patients eventually develop resistance to all currently used anti-estrogen therapies.

Androgenic steroids, such as testosterone and dihydrotestosterone (DHT), are the male sex hormones required for development of the male reproductive system and secondary sexual characteristics. Androgen activity is mediated via the androgen receptor (AR), a member of the ligand-dependent nuclear transcription factor family that also includes ER. Like estrogen-mediated activation of ER, binding of androgen to AR also triggers a conformational change that leads to homodimerization of AR. The AR homodimer then binds to androgen-response elements (AREs) within the promoters of target genes and regulates their expression with the help of transcriptional coregulators. Many AR target genes play critical roles in regulating cellular proliferation and survival, and deregulation of AR signaling is a major driver of prostate cancer development and progression. Thus, blocking androgen/AR signaling is a fundamental approach to treating prostate cancer. Currently, two classes of antiandrogen therapies are widely used: 1) reduction of androgen production by either surgical castration or administration of luteinizing hormone-releasing hormone superagonists or the CYP17 inhibitor Abiraterone, and 2) administration of small molecule antagonists that directly block androgen/AR interaction, such as flutamide, bicalutamide, enzalutamide, apalutamide, and darolutamide.

While current therapies can significantly prolong the survival of patients suffering from prostate cancer, resistance and relapse eventually develop. One mechanism by which resistance and relapse occurs is through reactivation of AR signaling, which can occur via increased accumulation or synthesis of androgens, augmented AR expression, or point mutations in AR that alter the affinity of the receptor to AR antagonists. Thus, new therapies that more effectively block AR signaling are needed.

Accordingly, a clear need exists to develop new therapeutics for the treatment of diseases that benefit from inhibition of ER, AR, and/or BET-domain containing proteins, without the harmful side effects associated with current therapeutics. One approach to achieving this goal would be to utilize the naturally occurring cellular ubiquitin-mediated degradation. Without being bound by theory, it is believed that degradation of ER, AR, or BET-domain containing proteins may be induced by bringing any one of the proteins into close proximity with an E3 ubiquitin ligase.

The phthalimide class of compounds, such as thalidomide, pomalidomide and lenalidomide, have been well known for its anti-cancer immunomodulatory activities and widely used for treating multiple myeloma, myelodysplastic syndrome (MDS), and non-Hodgkin's lymphoma (NHL). Their mechanism of action remained elusive, however, until 2010, when their molecular target was identified as cereblon (CRBN), the substrate receptor of the CUL4-Rbx1-DDB1-CRBN E3 ubiquitin ligase complex. Phthalimide compounds were shown to be able to hijack CRBN E3 ligase complex to form novel protein-protein interactions with several proteins, including IKZF1, IKZF3, CK1α, SALL4, and potentially many others, resulting in the ubiquitination and subsequent degradation of these proteins. While degradation of IKZF1 and IKZF3 produces therapeutic effects in treating multiple myeloma, and degradation of CK1α is beneficial for treating MDS, unwanted SALL4 degradation leads to the infamous thalidomide teratogenicity. Inspired by this observation, phthalimide compounds have recently been extended to generate hetero-bifunctional molecules, so called PROteolysis-TArgeting Chimeras (PROTACs), in which phthalimide E3 ligands are paired with protein targeting ligands via various linkers. PROTACs containing phthalimide E3 ligands have been shown to be capable of recruiting the CRBN E3 ligase complex to various substrate proteins, resulting in their targeted degradation. Successfully targeted substrate proteins include BRDs, ER, AR, and many kinases, with PROTACs targeting BET family members having been developed that show superior efficacy relative to direct inhibitors in ability to block signaling and inhibit cell growth. Thus, PROTACs offer many new avenues for drug discovery. PROTACs using phthalimide compounds carry significant therapeutic risks, however, due to their simultaneous off-target degradation of IKZF1, IKZF3, CK1α, SALL4 and potentially many additional undiscovered proteins. Thus, a need exists to develop new CRBN ligands that lack the intrinsic target degradation activity of phthalimide compounds.

Summary of the Embodiments

In some embodiments, provided herein, are compounds of Formula (I) and pharmaceutically acceptable salts thereof:

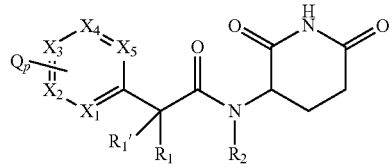

Formula (I)

wherein:
$X^1$, $X^2$, $X^3$, $X^4$, and $X^5$ are independently selected from C-Q, CH, and N;
$R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form a 5 to 7 member heterocyclic or heteroaryl ring;
Q is

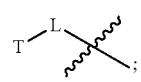

;

p is 1;
L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;
T is a targeting ligand;
$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and
each $R^4$ is independently selected from $C_1$-$C_6$ alkyl, halo, cyano, and hydroxyl.

In some embodiments provided herein, are compounds of Formula (Ia), and pharmaceutically acceptable salts thereof:

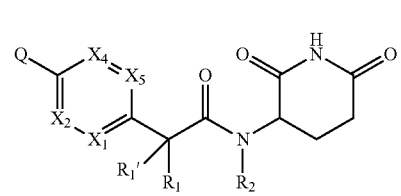

Formula (Ia)

wherein:
$X^1$, $X^2$, $X^4$, and $X^5$ are independently selected from CH and N; $R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form 5 to 7 member heterocyclic or heteroaryl ring;
Q is T

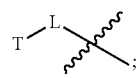

;

L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;
T is a targeting ligand;
$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and
each $R^4$ is independently selected from $C_1$-$C_6$ alkyl, halo, cyano, and hydroxyl.

In some embodiments provided herein, are compounds of Formula (Ib) and pharmaceutically acceptable salts thereof:

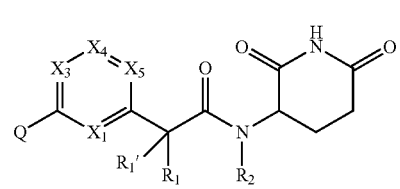

Formula (Ib)

wherein:
$X^1$, $X^3$, $X^4$, and $X^5$ are independently selected from CH and N;
$R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form 5 to 7 member heterocyclic or heteroaryl ring;
Q is L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;
T is a targeting ligand;
$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and
each $R^4$ is independently selected from $C_1$-$C_6$ alkyl, halo, cyano, and hydroxyl.

In some embodiments provided herein, are compounds of Formula (Ic) and pharmaceutically acceptable salts thereof:

Formula (Ic)

wherein:
$X^2$, $X^3$, $X^4$, and $X^5$ are independently selected from CH and N;
$R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form 5 to 7 member heterocyclic or heteroaryl ring;
Q is L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;
T is a targeting ligand;
$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and
each $R^4$ is independently selected from $C_1$-$C_6$ alkyl, halo, cyano, and hydroxyl.

Also disclosed herein is a method of treating cancer, wherein the cancer is selected from melanoma, breast cancer, prostate cancer, lung cancer, neuroblastoma, glioblastoma, hematologic malignancy, squamous-cell carcinoma, NUT carcinoma, basal cell carcinoma, adenocarcinoma, bladder cancer, bowel cancer, cervical cancer, colon cancer, esophageal cancer, head and neck cancer, kidney cancer, renal cell carcinoma, liver cancer, hepatocellular carcinoma, ovarian cancer, pancreatic cancer, stomach cancer, sarcoma, hemangiosarcoma, Kaposi's sarcoma, liposarcoma, myosarcoma, peripheral neuroepithelioma, synovial sarcoma, glioma, astrocytoma, oligodendroglioma, ependymoma, ganglioneuroma, ganglioglioma, medulloblastoma, pineal cell tumor, meningioma, meningeal sarcoma, neurofibroma, Schwannoma, uterine cancer, testicular cancer, thyroid cancer, carcinosarcoma, Wilms' tumor, and teratocarcinoma.

BRIEF DESCRIPTION OF THE FIGURES

The accompanying drawings, which are incorporated in and constitute a part of this specification, illustrate the disclosed embodiments and, together with the description, explain the principles of the disclosed embodiments. In the drawings.

DETAILED DESCRIPTION

Definitions

Figure 1A:
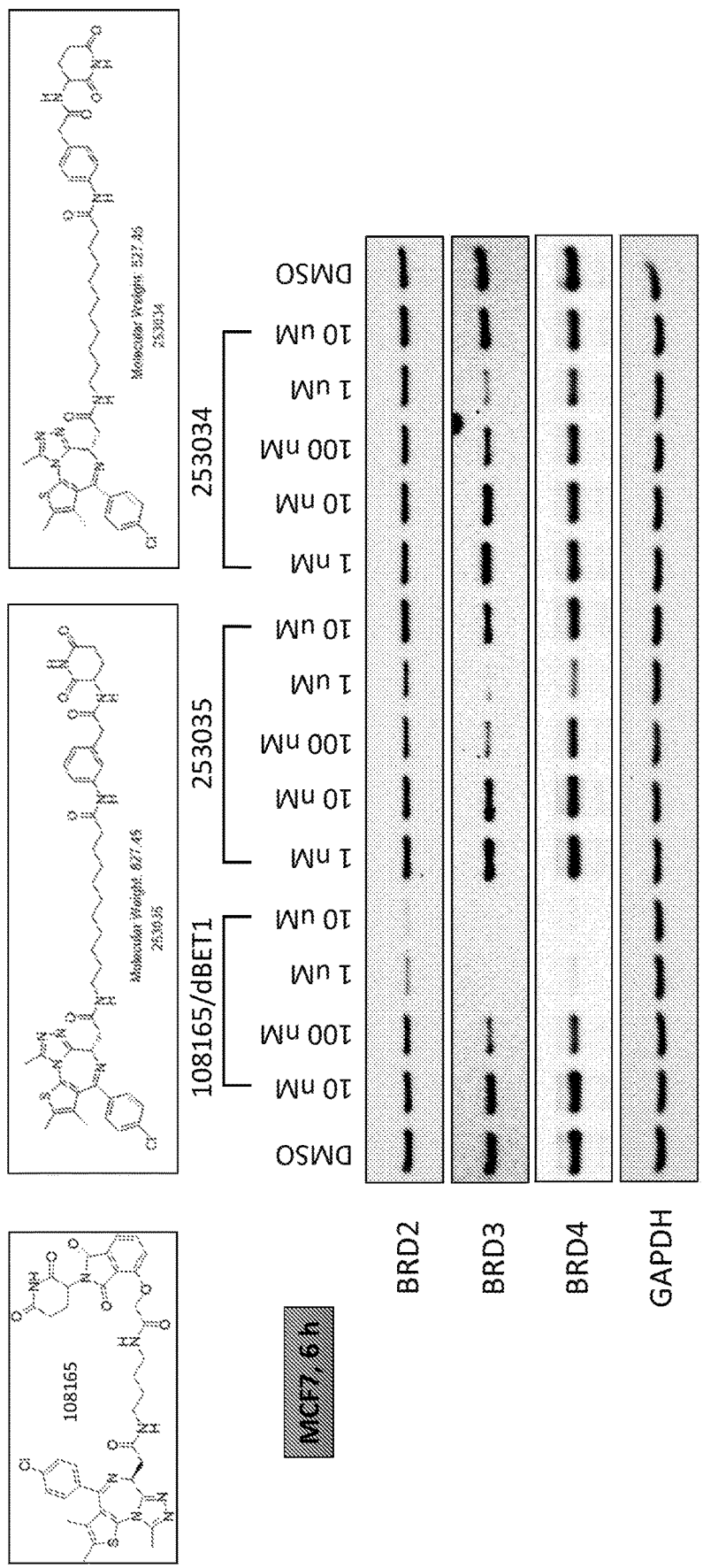
FIG. 1a and FIG. 1b illustrate the degradative activity of exemplary compounds 253035 and 253034 towards BRD2, BRD3 and BRD4 in a MCF7 cell line 6 hours after administration. 108165 (dBET1) was used as a positive control for BET degradative activity.

As used herein, "cancer" refers to diseases, disorders, and conditions that involve abnormal cell growth with the potential to invade or spread to other parts of the body. Exemplary cancers include, but are not limited to, breast cancer, lung cancer, ovarian cancer, endometrial cancer, prostate cancer, and esophageal cancer.

"Subject" refers to an animal, such as a mammal, that has been or will be the object of treatment, observation, or experiment. The methods described therein may be useful for both human therapy and veterinary applications. In one embodiment, the subject is a human.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder. For example, treating a cholesterol disorder may comprise decreasing blood cholesterol levels.

As used herein, "prevention" or "preventing" refers to a reduction of the risk of acquiring a given disease or disorder.

A dash ("-") that is not between two letters or symbols is used to indicate a point of attachment for a substituent. For example, —CN is attached through the carbon atom.

By "optional" or "optionally" it is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently unstable.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

The term "alkenyl" as used herein refers to an unsaturated straight or branched hydrocarbon having at least one carbon-carbon double bond, such as a straight or branched group of 2-8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkyl" as used herein refers to a saturated straight or branched hydrocarbon, such as a straight or branched group of 1-8 carbon atoms, referred to herein as ($C_1$-$C_8$)alkyl. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_5$)alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "aryl" as used herein refers to a mono-, bi-, or other multi-carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$C_6$-aryl."

The term "cyano" as used herein refers to —CN.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

The term "heteroaryl" as used herein refers to a mono-, bi-, or multi-cyclic, aromatic ring system containing one or more heteroatoms, for example 1-3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl."

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," ACS Symposium Series, Vol. 14, and in Roche, E. B., ed. *Bioreversible Carriers in Drug Design*, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The term "sulfhydryl" as used herein refers to —SH.

The term "targeting ligand" as used herein refers to a compound or a portion of a compound that binds to a target protein. In some embodiments, a targeting ligand is a portion of a PROTAC compound.

The term "target protein" as used herein refers to the protein bound by a targeting ligand. In some embodiment, the target protein is a non-CRBN protein bound one of the PROTACs disclosed herein. In some embodiments, addition of one of the PROTACs disclosed herein to a solution comprising a target protein and CRBN can increase association between CRBN and the target protein relative to the same solution lacking the PROTAC. In some embodiments, addition of one of the PROTACs of the present disclosure to a solution comprising CRBN and the target protein can increase the number of ubiquitin moieties attached to the target protein relative to the same solution lacking the PROTAC. In some embodiments, addition of one of the PROTACs disclosed herein to a solution comprising CRBN and a target protein can increase the degradation rate of the target protein relative to the same solution lacking the PROTAC.

In some embodiments, the targeting ligand binds to a target protein selected from a protein containing a BET domain, an Estrogen Receptor (ER), and an Androgen Receptor (AR). In some embodiments the target protein may contain a BET domain. In some embodiments, the targeting ligand may bind one or more of BRD2, BRD3, BRD4 and/or BRDT. In some embodiments, the target protein may be BRD2. In some embodiments, the target protein may be BRD3. In some embodiments, the target protein may be BRD4. In some embodiments, the targeting protein may be BRDT. In some embodiments, the target protein may be ER. In some embodiments, the ER may be ERα or ERβ. In some embodiments, the target protein may be AR.

In some embodiments, the targeting ligand may be a SERM, such as, e.g., tamoxifen, toremifene, or raloxifene. In some embodiments, the targeting ligand may be tamoxifen. In some embodiments, the targeting ligand may be a SERD, such as, e.g., fulvestrant. In some embodiments, the targeting ligand may be a small molecule antagonist that directly blocks androgen/AR interaction, such as, e.g., flutamide, bicalutamide, enzalutamide, apalutamide, or darolutamide. In some embodiments, the targeting ligand may be bicalutamide or a derivative thereof. In some embodiments, the targeting ligand may be enzalutamide or a derivative thereof. In some embodiments, the targeting ligand may be a BET inhibitor. In some embodiments the targeting ligand may be JQ1 or a derivative thereof.

Chemical names were generated using PerkinElmer ChemDraw® Professional, version 18.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

Additionally, unless otherwise stated, structures described herein are also meant to include compounds that differ only in the presence of one or more isotopically enriched atoms. For example, compounds having the present structures except for the replacement of hydrogen by deuterium ($^2$H) or tritium ($^3$H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein, are compounds of Formula (I) or pharmaceutically acceptable salts thereof:

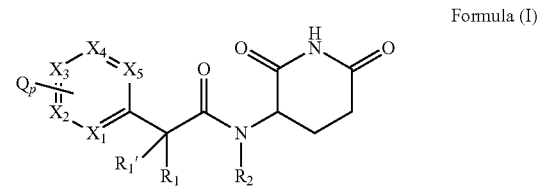

Formula (I)

wherein:

$X^1$, $X^2$, $X^3$, $X^4$, and $X^5$ are independently selected from C-Q, CH, and N;

$R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form a 5 to 7 member heterocyclic or heteroaryl ring;

Q is

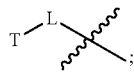;

p is 1;

L is a linker of 1 to 22 carbon atoms in length, wherein one or more carbon atoms are each optionally and independently replaced by a group selected from C(O), O, NR$^3$, S, SO, SO$_2$, C$_2$-alkenyl, C$_2$-alkynyl, cycloalkyl, aryl, heterocycle, and heteroaryl, each of which can be substituted with 0, 1, 2, or 3 R$^4$;

T is a targeting ligand;

R$^3$ is independently selected from H, C$_1$-C$_6$ alkyl, aryl, heteroaryl, and acyl, where acyl can contain C$_1$-C$_6$ alkyl, C$_1$-C$_6$ cycloalkyl, aryl and heteroaryl, each of which can be substituted with 0, 1, 2, or 3 R$^4$; and each R$^4$ is independently selected from C$_1$-C$_6$ alkyl, halo, cyano, and hydroxyl.

In some embodiments provided herein, are compounds of Formula (Ia), and pharmaceutically acceptable salts thereof:

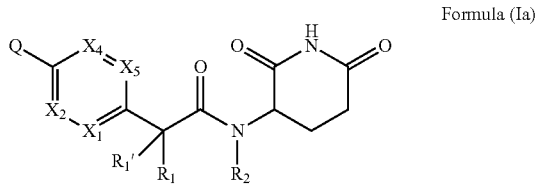

Formula (Ia)

wherein:

X$^1$, X$^2$, X$^4$, and X$^5$ are independently selected from CH and N;

R$^1$, R$^{1'}$ and R$^2$ are independently selected from H, C$_1$-C$_6$ alkyl, C$_3$-C$_6$ cycloalkyl, aryl, halo, hydroxy, and sulfhydryl, each of which is substituted with 0, 1, 2, or 3 R$^4$, wherein R$^1$ and R$^{1'}$ can be connected to form a 3 to 6 member heterocyclic or heteroaryl ring, and R$^1$ and R$^2$ can be connected to form 5 to 7 member heterocyclic or heteroaryl ring;

Q is

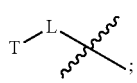

L is a linker of 1 to 22 carbon atoms in length, wherein one or more carbon atoms are each optionally and independently replaced by a group selected from C(O), O, NR$^3$, S, SO, SO$_2$, C$_2$-alkenyl, C$_2$-alkynyl, cycloalkyl, aryl, heterocycle, and heteroaryl, each of which can be substituted with 0, 1, 2, or 3 R$^4$;

T is a targeting ligand;

R$^3$ is independently selected from H, C$_1$-C$_6$ alkyl, aryl, heteroaryl, and acyl, where acyl can contain C$_1$-C$_6$ alkyl, C$_1$-C$_6$ cycloalkyl, aryl and heteroaryl, each of which can be substituted with 0, 1, 2, or 3 R$^4$; and each R$^4$ is independently selected from C$_1$-C$_6$ alkyl, halo, cyano, and hydroxyl.

In some embodiments provided herein, are compounds of Formula (Ib) and pharmaceutically acceptable salts thereof:

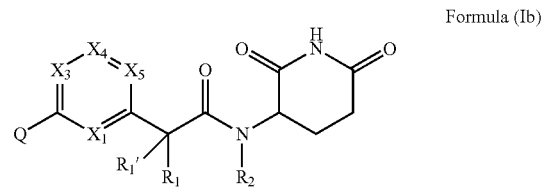

Formula (Ib)

wherein:

X$^1$, X$^3$, X$^4$, and X$^5$ are independently selected from CH and N;

R$^1$, R$^{1'}$ and R$^2$ are independently selected from H, C$_1$-C$_6$ alkyl, C$_3$-C$_6$ cycloalkyl, aryl, halo, hydroxy, and sulfhydryl, each of which is substituted with 0, 1, 2, or 3 R$^4$, wherein R$^1$ and R$^{1'}$ can be connected to form a 3 to 6 member heterocyclic or heteroaryl ring, and R$^1$ and R$^2$ can be connected to form 5 to 7 member heterocyclic or heteroaryl ring;

Q is

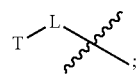

L is a linker of 1 to 22 carbon atoms in length, wherein one or more carbon atoms are each optionally and independently replaced by a group selected from C(O), O, NR$^3$, S, SO, SO$_2$, C$_2$-alkenyl, C$_2$-alkynyl, cycloalkyl, aryl, heterocycle, and heteroaryl, each of which can be substituted with 0, 1, 2, or 3 R$^4$;

T is a targeting ligand;

R$^3$ is independently selected from H, C$_1$-C$_6$ alkyl, aryl, heteroaryl, and acyl, where acyl can contain C$_1$-C$_6$ alkyl, C$_1$-C$_6$ cycloalkyl, aryl and heteroaryl, each of which can be substituted with 0, 1, 2, or 3 R$^4$; and each R$^4$ is independently selected from C$_1$-C$_6$ alkyl, halo, cyano, and hydroxyl.

In some embodiments provided herein, are compounds of Formula (Ic) and pharmaceutically acceptable salts thereof:

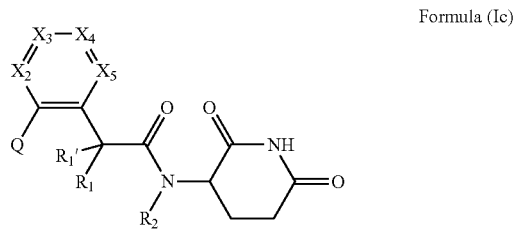

Formula (Ic)

wherein:

X$^2$, X$^3$, X$^4$, and X$^5$ are independently selected from CH and N;

R$^1$, R$^{1'}$ and R$^2$ are independently selected from H, C$_1$-C$_6$ alkyl, C$_3$-C$_6$ cycloalkyl, aryl, halo, hydroxy, and sulfhydryl, each of which is substituted with 0, 1, 2, or 3 R$^4$, wherein R$^1$ and R$^{1'}$ can be connected to form a 3 to 6 member heterocyclic or heteroaryl ring, and R$^1$ and R$^2$ can be connected to form 5 to 7 member heterocyclic or heteroaryl ring;

Q i

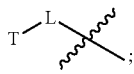

L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;

T is a targeting ligand;

$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and each $R^4$ is independently selected from $C_1$-$C_6$ alkyl, halo, cyano, and hydroxyl.

In some embodiments, $R^1$, $R^{1'}$, and $R^2$ may each be independently selected from H, $C_1$-$C_3$ alkyl, $C_3$-$C_6$ cycloalkyl, aryl, halo, hydroxy, and sulfhydryl, each of which may be substituted with 0, 1, 2, or 3 $R^4$. In some embodiments, $R^1$, $R^{1'}$ and $R^2$ may each be independently selected from H, $C_1$ alkyl, $C_3$ cycloalkyl, halo, and hydroxy, each of which may be substituted with 0, 1, 2, or 3 $R^4$. In some embodiments, $R^1$, $R^{1'}$ and $R^2$ may each be independently selected from H, $C_1$ alkyl, and $C_3$ cycloalkyl. In some embodiments, $R^1$ may be chosen from H, $C_1$ alkyl, and $C_3$ cycloalkyl. In some embodiments, $R^{1'}$ may be chosen from H, $C_1$ alkyl, and $C_3$ cycloalkyl. In some embodiments, $R^1$ and $R^{1'}$ may be connected to form a 3-6 membered ring. In some embodiments, $R^1$ and $R^{1'}$ may be connected to form a 3 membered ring. In some embodiments, $R^1$ and $R^2$ may be connected to form a 5-7 membered ring. In some embodiments, $R^1$ and $R^2$ may be connected to form a 6 membered heteroaryl ring. In some embodiments, $R^2$ may be H or $C_1$ alkyl.

In some embodiments, $R^1$ may be H. In some embodiments, $R^1$ may be $C_1$ alkyl. In some embodiments, $R^1$ may be $C_3$ cycloalkyl. In some embodiments, $R^{1'}$ may be H. In some embodiments, $R^{1'}$ may be $C_1$ alkyl. In some embodiments, $R^{1'}$ may be $C_3$ cycloalkyl. In some embodiments, $R^2$ may be H. In some embodiments, $R^2$ may be $C_1$ alkyl.

In some embodiments, $R^1$ may be H, $R^{1'}$ may be H, and $R^2$ may be H. In some embodiments, $R^1$ may be $C_1$ alkyl, $R^{1'}$ may be H, and $R^2$ may be H. In some embodiments, $R^{1'}$ may be H, $R^{1'}$ may be C, alkyl, and $R^2$ may be H. In some embodiments, $R^1$ may be $C_1$ alkyl, $R^{1'}$ may be H, and $R^2$ may be H, and the stereocenter carbon to which R1 and R1' are bound is in an S configuration. In some embodiments, $R^1$ may be $C_1$ alkyl, $R^{1'}$ may be H, and $R^2$ may be H, and the stereocenter carbon to which $R^1$ and $R^{1'}$ are bound is in an R configuration. In some embodiments, $R^1$ may be $C_1$ alkyl, $R^{1'}$ may be $C_1$ alkyl, $R^2$ may be H, and $R^{1'}$ and $R^{1'}$ may be connected to form a $C_3$ cyclopropyl ring.

In some embodiments, $R^4$ may be $C_1$ alkyl.

In some embodiments, $X^1$, $X^2$, $X^3$, $X^4$, and $X^5$ may be independently chosen from C-Q or CH. In some embodiments, $X^1$ may be N and $X^2$, $X^3$, $X^4$, and $X^5$ may be independently chosen from C-Q or CH. In some embodiments, $X^2$ may be N and $X^1$, $X^3$, $X^4$, and $X^5$ may be independently chosen from C-Q or CH. In some embodiments, $X^3$ may be N and $X^1$, $X^2$, $X^4$, and $X^5$ may be independently chosen from C-Q or CH. In some embodiments, $X^4$ may be N and $X^1$, $X^2$, $X^3$, and $X^5$ may be independently chosen from C-Q or CH. In some embodiments, $X^5$ may be N and $X^1$, $X^2$, $X^3$, and $X^4$ may be independently chosen from C-Q or CH.

In some embodiments, $X^3$ may be C-Q and $X^1$, $X^2$, $X^4$, and $X^5$ may be CH. In some embodiments, $X^3$ may be C-Q, $X^2$ may be N, and $X^1$, $X^4$ and $X^5$ may be CH. In some embodiments, $X^3$ may be C-Q, $X^1$ may be N, and $X^2$, $X^4$ and $X^5$ may be CH. In some embodiments, $X^3$ may be C-Q, $X^4$ may be N, and $X^1$, $X^2$ and $X^5$ may be CH. In some embodiments, $X^3$ may be C-Q, $X^5$ may be N, and $X^1$, $X^2$ and $X^4$ may be CH. In some embodiments, $X^3$ may be C-Q, $X^2$ and $X^4$ may be N, and $X^1$ and $X^5$ may be CH. In some embodiments, $X^3$ may be C-Q, $X^1$ and $X^2$ may be N, and $X^4$ and $X^5$ may be CH.

In some embodiments, $X^2$ may be C-Q and $X^1$, $X^3$, $X^4$, and $X^5$ may be CH. In some embodiments, $X^2$ may be C-Q, $X^1$ may be N, and $X^3$, $X^4$, and $X^5$ may be CH. In some embodiments, $X^2$ may be C-Q, $X^3$ may be N, and $X^1$, $X^4$, and $X^5$ may be CH. In some embodiments, $X^2$ may be C-Q, $X^4$ may be N, and $X^1$, $X^3$, and $X^5$ may be CH. In some embodiments, $X^2$ may be C-Q, $X^5$ may be N, and $X^1$, $X^3$, and $X^4$ may be CH.

In some embodiments, $X^1$ may be C-Q and $X^2$, $X^3$, $X^4$, and $X^5$ may be CH. In some embodiments, $X^1$ may be C-Q, $X^2$ may be N, and $X^3$, $X^4$, and $X^5$ may be CH. In some embodiments, $X^1$ may be C-Q, $X^3$ may be N, and $X^2$, $X^4$ and $X^5$ may be CH. In some embodiments, $X^1$ may be C-Q, $X^4$ may be N, and $X^2$, $X^3$ and $X^5$ may be CH. In some embodiments, $X^1$ may be C-Q, $X^5$ may be N, and $X^2$, $X^3$ and $X^4$ may be CH.

In some embodiments, L may be a linker of 1 to 16 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which is independently substituted with 0, 1, 2, or 3 $R^4$. In some embodiments, L may be a linker of 3 to 15 carbon atoms in length. In some embodiments, L may be a linker of 3 to 12 carbon atoms in length. In some embodiments, L may be a linker of 3 to 10 carbon atoms in length. In some embodiments, L may be a linker of 3 to 8 carbon atoms in length. In some embodiments, L may be a linker of 3 to 5 carbon atoms in length. In some embodiments, L may be a linker of 6 to 13 carbon atoms in length. In some embodiments, L may be a linker of 8 to 13 carbon atoms in length. In some embodiments, L may be a linker of 10 to 13 carbon atoms in length.

In some embodiments, L may be a linker wherein two carbon atoms are each independently replaced by a heterocycle, each of which is independently substituted with 0, 1, 2, or 3 $R^4$. In some embodiments, L may be a linker wherein one carbon atom is replaced by a heterocycle and one carbon atom is replaced by a cycloalkyl, each of which is independently substituted with 0, 1, 2, or 3 $R^4$. In some embodiments, L may be a linker wherein two or more carbon atoms are each independently replaced by a group selected from C(O), O, $NR^3$, S, SO, $SO_2$, $C_2$-alkenyl, $C_2$-alkynyl, cycloalkyl, aryl, heterocycle, and heteroaryl, each of which is independently substituted with 0, 1, 2, or 3 $R^4$. In some embodiments, L may be a linker wherein one or more carbon atoms is each independently replaced by a group selected from C(O), O, $NR^3$, $C_2$-alkynyl, and heterocycle each of which is substituted with 0, 1, 2, or 3 $R^4$. In some embodiments, L may be a linker wherein two or more carbon atoms are each independently replaced by a group selected from C(O), O, $NR^3$, $C_2$-alkynyl, and heterocycle each of which is substituted with 0, 1, 2, or 3 $R^4$.

In some embodiments, $R^3$ may be independently selected from H and $C_1$-$C_6$ alkyl.
In some embodiments, L may be selected from
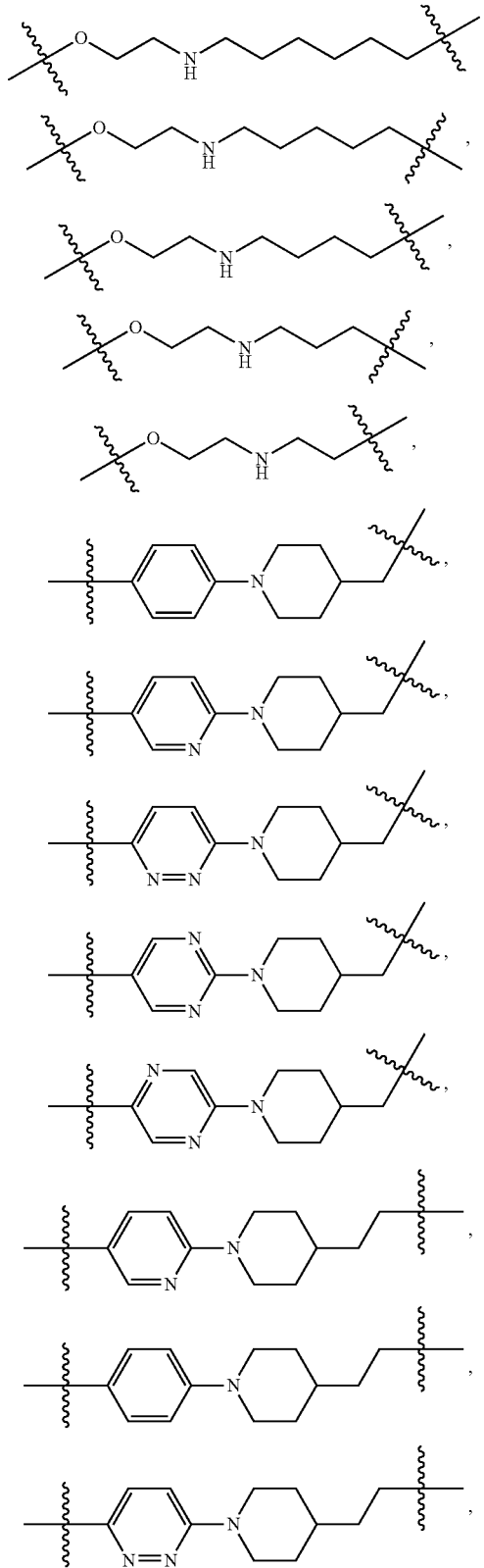
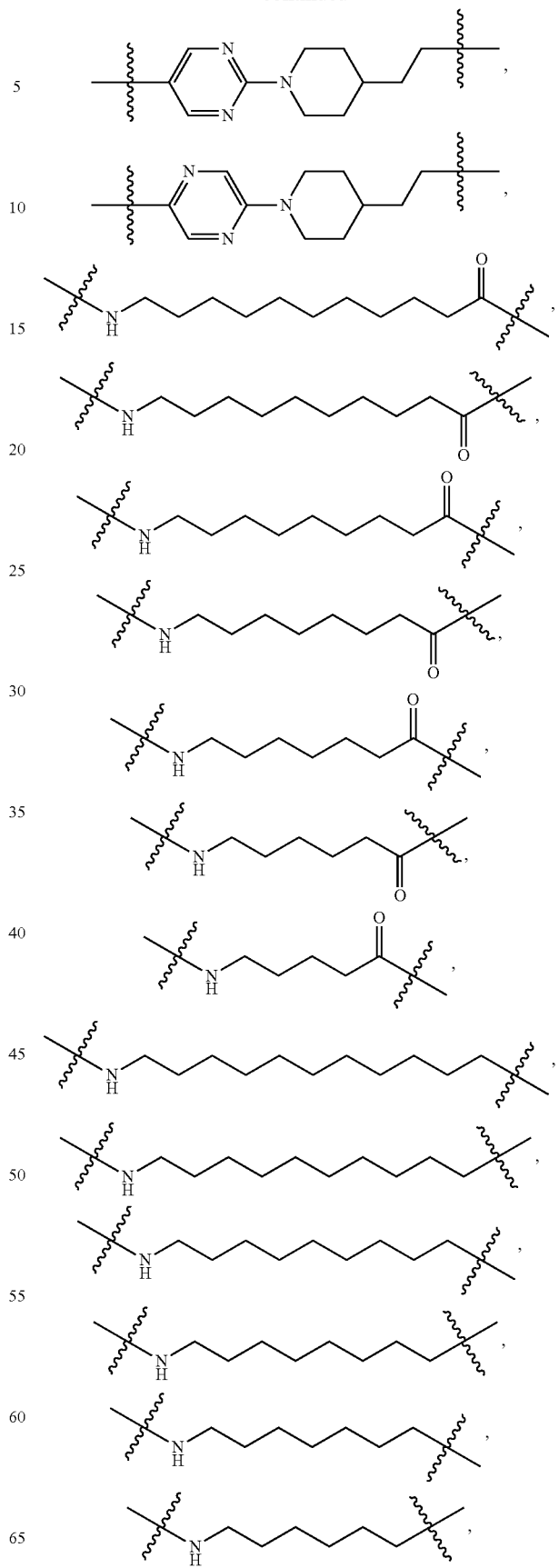

-continued
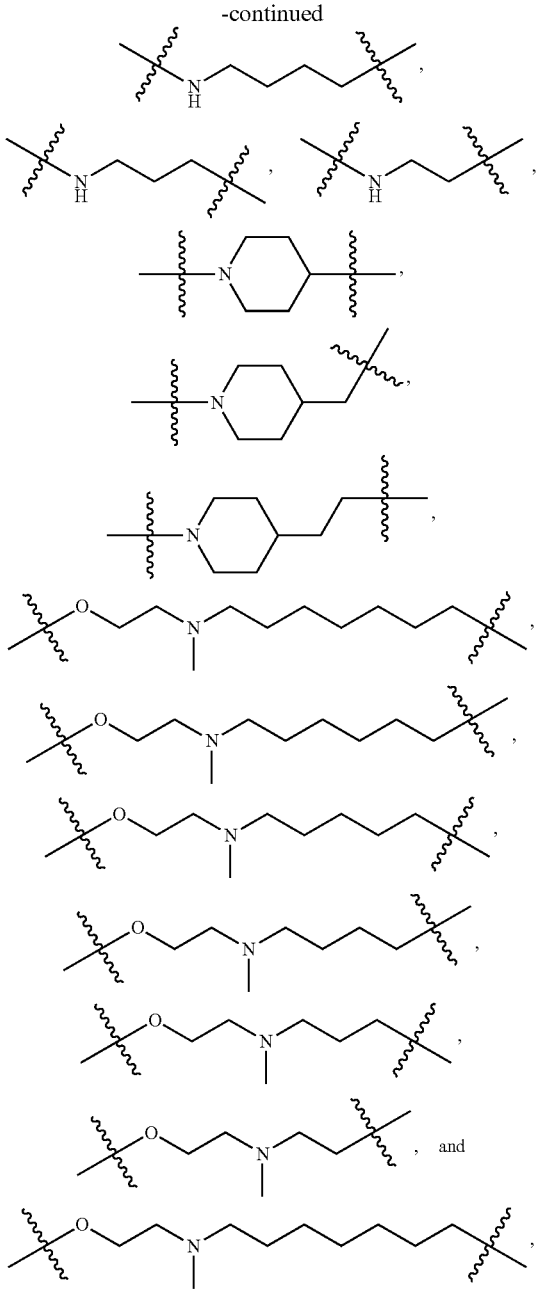
In some embodiments, L may be
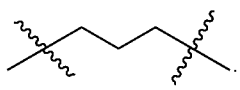 [SMILES: *CCC*]
In some embodiments, L may be
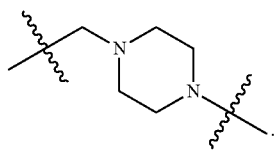 [SMILES: *CN1CCN(*)CC1]
In some embodiments, L may be
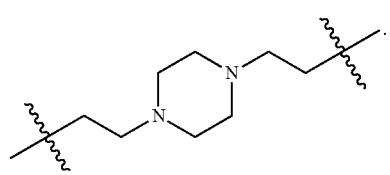 [SMILES: *CCN1CCN(CC*)CC1]
In some embodiments, L may be
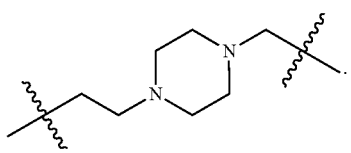 [SMILES: *CCN1CCN(C*)CC1]
In some embodiments, L may be
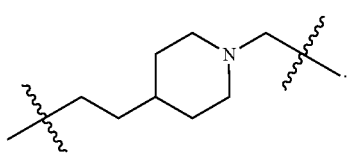 [SMILES: *CCC1CCN(C*)CC1]
In some embodiments, L may be
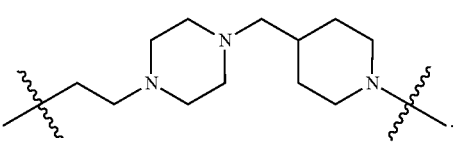 [SMILES: *CCN1CCN(CC2CCN(*)CC2)CC1]
In some embodiments, L may be
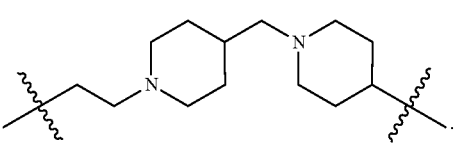 [SMILES: *CCN1CCC(CN2CCC(*)CC2)CC1]
In some embodiments, L may be
In some embodiments, L may be
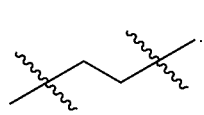

In some embodiments, L may be
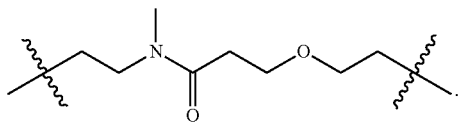 [SMILES: *CCOCCC(=O)N(C)CC*]
In some embodiments, L may be
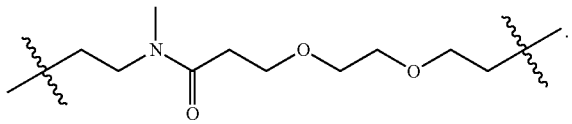 [SMILES: *CCOCCOCCC(=O)N(C)CC*]
In some embodiments, L may be
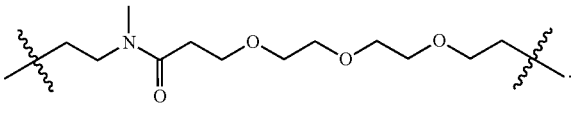 [SMILES: *CCOCCOCCOCCC(=O)N(C)CC*]
In some embodiments, L may be
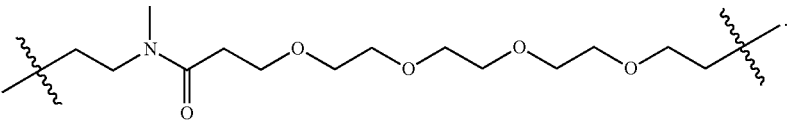 [SMILES: *CCOCCOCCOCCOCCC(=O)N(C)CC*]
In some embodiments, L may be
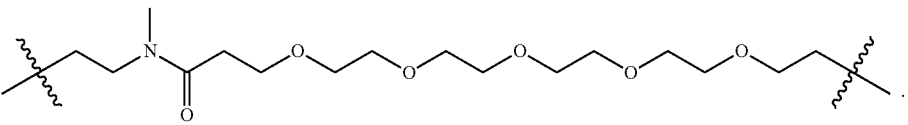 [SMILES: *CCOCCOCCOCCOCCOCCC(=O)N(C)CC*]
In some embodiments, L may be
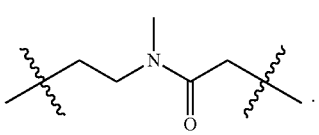 [SMILES: *CCN(C)C(=O)C*]
In some embodiments, L may be
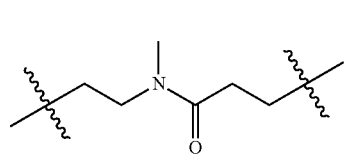
In some embodiments, L may be
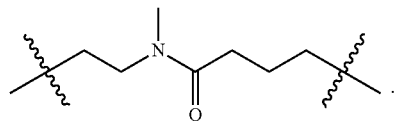 [SMILES: *CCCC(=O)N(C)CC*]
In some embodiments, L may be
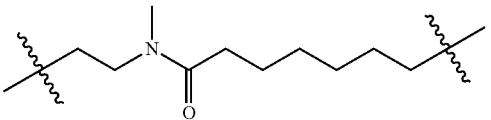
In some embodiments, L may be
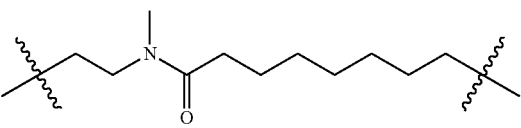
In some embodiments, L may be
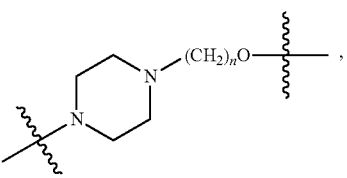
In some embodiments, L may be
where n may be 2 to 8.

In some embodiments, L may be
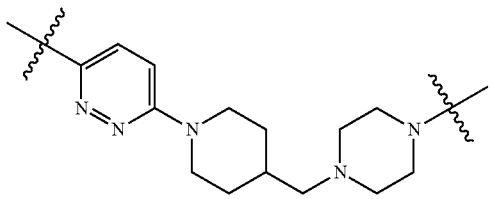
In some embodiments, L may be
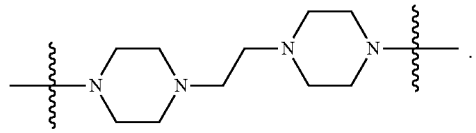
In some embodiments, L may be
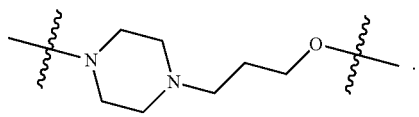 [SMILES: *OCCCN1CCN(*)CC1]
In some embodiments, L may be
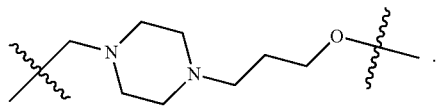 [SMILES: *CN1CCN(CCCO*)CC1]
In some embodiments, L may be
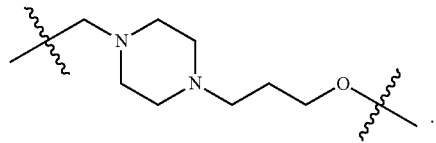 [SMILES: *CN1CCN(CCCO*)CC1]
In some embodiments, L may be
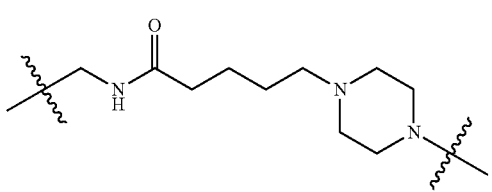
In some embodiments, L may be
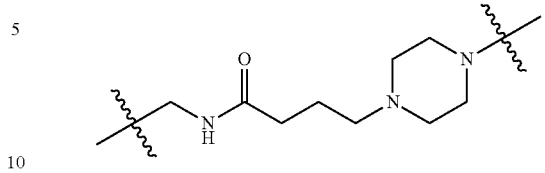
In some embodiments, L may be
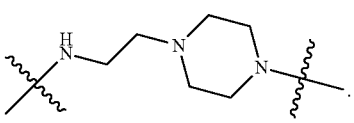 [SMILES: *NCCN1CCN(*)CC1]
In some embodiments, L may be
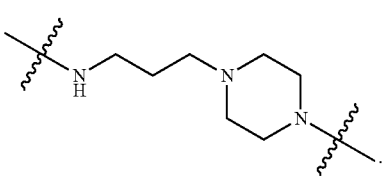 [SMILES: *NCCCN1CCN(*)CC1]
In some embodiments, L may be
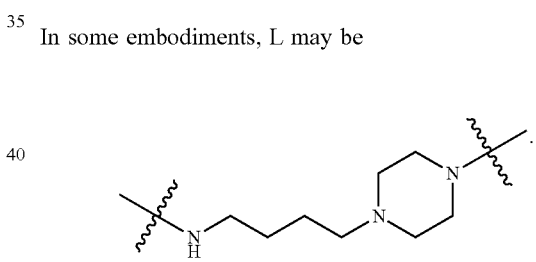
In some embodiments, L may be
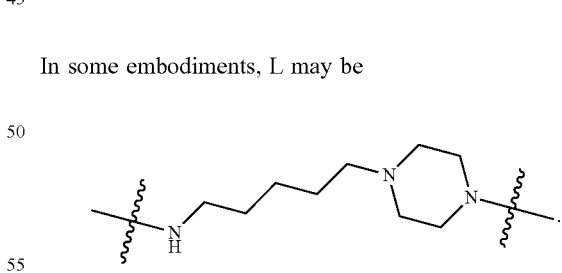

In some embodiments, L may be

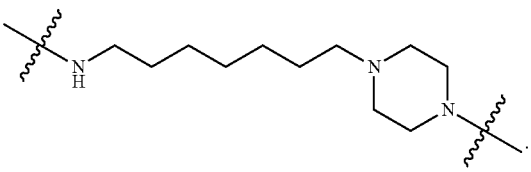 [SMILES: *NCCCCCCCN1CCN(*)CC1]

In some embodiments, L may be

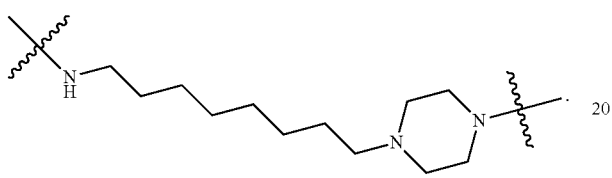

In some embodiments, L may be

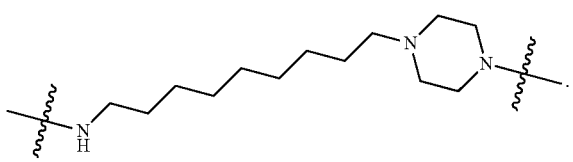 [SMILES: *NCCCCCCCCCN1CCN(*)CC1]

In some embodiments, L may be

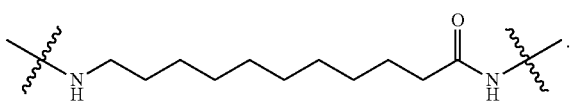 [SMILES: *NCCCCCCCCCCC(=O)N*]

In some embodiments, L may be

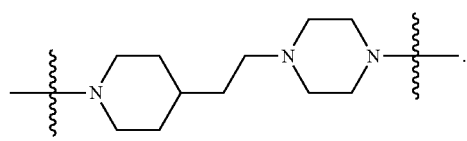 [SMILES: *N1CCC(CCN2CCN(*)CC2)CC1]

In some embodiments, L may be

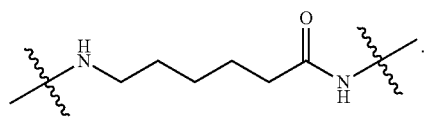 [SMILES: *NCCCCCC(=O)N*]

In some embodiments, L may be

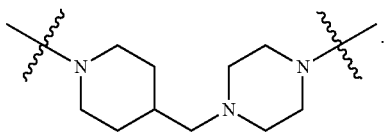 [SMILES: *N1CCC(CN2CCN(*)CC2)CC1]

In some embodiments, the targeting ligand may bind ER. In some embodiments, the targeting ligand may have the following formula, and pharmaceutically acceptable salts thereof:

Formula (II)

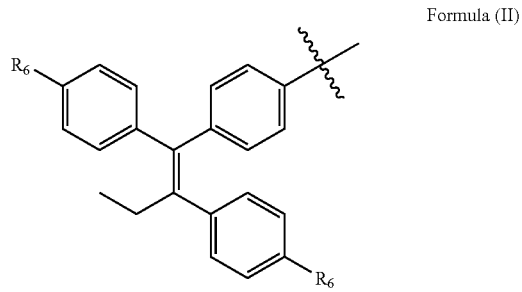

wherein:
- $R^5$ is selected from H, $C_1$-$C_6$ alkyl, halo, hydroxy, and sulfhydryl, each of which is substituted with 0, 1, 2, or 3 $R^1$;
- $R^6$ is selected from H, OH, $C_1$-$C_6$ alkyl, and acyl, each of which is substituted with 0, 1, 2, or 3 $R^8$;
- each $R^8$ is independently selected from $C_1$-$C_6$ alkyl, halo, cyano, and hydroxy; and wherein

is a bond to L.

In some embodiments, the targeting ligand has the following formula, and pharmaceutically acceptable salts thereof:

Formula (III)

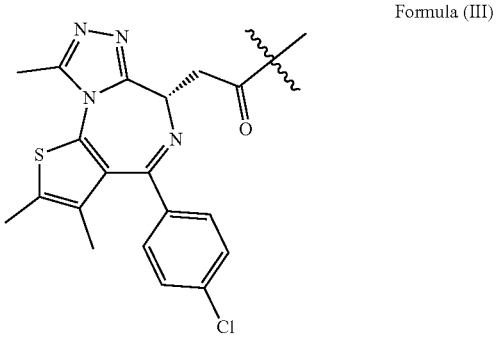 [SMILES: *C(=O)C[C@@H]1N=C(c2ccc(Cl)cc2)c2c(sc(C)c2C)-n2c(C)nnc21]

wherein

is a bond to L.

In some embodiments, the targeting ligand has the following formula, and pharmaceutically acceptable salts thereof:

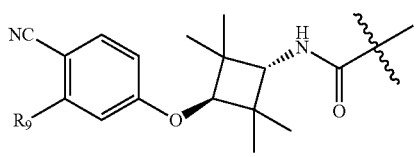

Formula (IV)

wherein $R^9$ is selected from Cl, CH$_3$, CF$_3$, and OCH$_3$, and wherein

is a bond to L.

In some embodiments, the targeting ligand has the following formula, and pharmaceutically acceptable salts thereof:

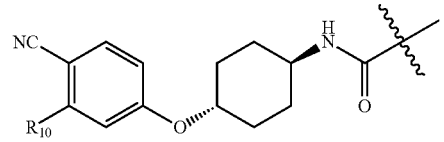

(Formula V)

wherein $R^{10}$ is selected from Cl, CH$_3$, CF$_3$, and OCH$_3$, and wherein

is a bond to L.

In some embodiments, the targeting ligand has the following formula, and pharmaceutically acceptable salts thereof:

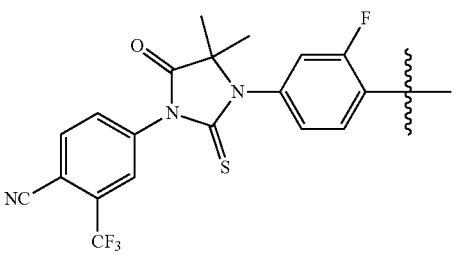

Formula (VI)

wherein

is a bond to L.

In some embodiments, the targeting ligand has the following formula, and pharmaceutically acceptable salts thereof:

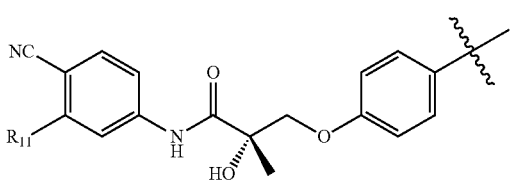

Formula (VII)

wherein $R^{11}$ is selected from Cl, CH$_3$, CF$_3$, and OCH$_3$; and wherein

is a bond to L.

In some embodiments, at least one of $X^1$, $X^2$, $X^3$, $X^4$, or $X^5$ may be not N, or $R^{1'}$ or $R^1$ may be not H.

In some embodiments, provided herein is a compound, or a pharmaceutically acceptable salt thereof, chosen from:

N-((1r,4r)-4-(3-chloro-4-cyanophenoxy)cyclohexyl)-6-(4-((4-(3-(2-((2,6-dioxopiperidin-3-yl)(methyl)amino)-2-oxoethyl)phenyl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)(methyl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(2-(2-((2,6-dioxopiperidin-3-yl)(methyl)amino)-2-oxoethyl)pyridin-4-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)(methyl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)amino)-2-oxoethyl)phenyl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)(methyl)amino)-2-oxoethyl)phenyl)piperazin-1-yl)methyl)piperidin-1-yl)pyridazine-3-carboxamide;

N-((1r,4r)-4-(3-chloro-4-cyanophenoxy)cyclohexyl)-6-(4-((4-(5-(2-((2,6-dioxopiperidin-3-yl)(methyl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)(methyl)amino)-2-oxoethyl)pyridin-3-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)amino)-2-oxoethyl)pyridin-3-yl)piperazin-1-yl)methyl)piperidin-1-yl)pyridazine-3-carboxamide;

(2S)—N-(4-cyano-3-(trifluoromethyl)phenyl)-3-(4-(4-(2-(4-(3-(2-((2,6-dioxopiperidin-3-yl)(methyl)amino)-2-oxoethyl)phenyl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(5-(2-((2,6-dioxopiperidin-3-yl)(methyl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(4-(2-((2,6-dioxopiperidin-3-yl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(2-(2-((2,6-dioxopiperidin-3-yl)(methyl)amino)-2-oxoethyl)pyridin-4-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(6-(2-((2,6-dioxopiperidin-3-yl)(methyl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(6-(2-((2,6-dioxopiperidin-3-yl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(4-(2-((2,6-dioxopiperidin-3-yl)(methyl)amino)-2-oxoethyl)phenyl)piperazin-1-yl)ethyl)piperazin-1-yl)phenoxy)-2-hydroxy-2-methylpropanamide;

N-(4-cyano-3-(trifluoromethyl)phenyl)-3-(4-(4-(3-(4-(2-((2,6-dioxopiperidin-3-yl)(methyl)amino)-2-oxoethyl)phenoxy)propyl)piperazin-1-yl)phenoxy)-2-hydroxy-2-methylpropanamide;

N-(4-cyano-3-(trifluoromethyl)phenyl)-3-(4-(4-(3-(4-(2-((2,6-dioxopiperidin-3-yl)amino)-2-oxoethyl)phenoxy)propyl)piperazin-1-yl)phenoxy)-2-hydroxy-2-methylpropanamide;

N-(4-cyano-3-(trifluoromethyl)phenyl)-3-(4-((4-(3-(3-(2-((2,6-dioxopiperidin-3-yl)amino)-2-oxoethyl)phenoxy)propyl)piperazin-1-yl)methyl)phenoxy)-2-hydroxy-2-methylpropanamide;

N-(4-cyano-3-(trifluoromethyl)phenyl)-3-(4-((4-(3-(3-(2-((2,6-dioxopiperidin-3-yl)(methyl)amino)-2-oxoethyl)phenoxy)propyl)piperazin-1-yl)methyl)phenoxy)-2-hydroxy-2-methylpropanamide;

N-(4-(3-((4-cyano-3-(trifluoromethyl)phenyl)amino)-2-hydroxy-2-methyl-3-oxopropoxy)benzyl)-5-(4-(4-(2-((2,6-dioxopiperidin-3-yl)amino)-2-oxoethyl)pyridin-2-yl)piperazin-1-yl)pentanamide;

N-(4-(3-((4-cyano-3-(trifluoromethyl)phenyl)amino)-2-hydroxy-2-methyl-3-oxopropoxy)benzyl)-5-(4-(4-(2-((2,6-dioxopiperidin-3-yl)(methyl)amino)-2-oxoethyl)pyridin-2-yl)piperazin-1-yl)pentanamide;

N-(4-((S)-3-((4-cyano-3-(trifluoromethyl)phenyl)amino)-2-hydroxy-2-methyl-3-oxopropoxy)benzyl)-4-(4-(4-(2-((2,6-dioxopiperidin-3-yl)amino)-2-oxoethyl)pyridin-2-yl)piperazin-1-yl)butanamide; and N-(4-((S)-3-((4-cyano-3-(trifluoromethyl)phenyl)amino)-2-hydroxy-2-methyl-3-oxopropoxy)benzyl)-4-(4-(4-(2-((2,6-dioxopiperidin-3-yl)(methyl)amino)-2-oxoethyl)pyridin-2-yl)piperazin-1-yl)butanamide.

In some embodiments, provided herein is a compound, or pharmaceutically acceptable salt thereof, chosen from:

2-((S)-4-(4-chlorophenyl)-2,3,9-trimethyl-6H-thieno[3,2-f][1,2,4]triazolo[4,3-a][1,4]diazepin-6-yl)-N-(2-(4-(3-(2-((2,6-dioxopiperidin-3-yl)amino)-2-oxoethyl)phenyl)piperazin-1-yl)ethyl)acetamide;

2-((S)-4-(4-chlorophenyl)-2,3,9-trimethyl-6H-thieno[3,2-f][1,2,4]triazolo[4,3-a][1,4]diazepin-6-yl)-N-(3-(4-(3-(2-((2,6-dioxopiperidin-3-yl)amino)-2-oxoethyl)phenyl)piperazin-1-yl)propyl)acetamide;

2-((S)-4-(4-chlorophenyl)-2,3,9-trimethyl-6H-thieno[3,2-f][1,2,4]triazolo[4,3-a][1,4]diazepin-6-yl)-N-(4-(4-(3-(2-((2,6-dioxopiperidin-3-yl)amino)-2-oxoethyl)phenyl)piperazin-1-yl)butyl)acetamide;

2-((S)-4-(4-chlorophenyl)-2,3,9-trimethyl-6H-thieno[3,2-f][1,2,4]triazolo[4,3-a][1,4]diazepin-6-yl)-N-(5-(4-(3-(2-((2,6-dioxopiperidin-3-yl)amino)-2-oxoethyl)phenyl)piperazin-1-yl)pentyl)acetamide;

2-((S)-4-(4-chlorophenyl)-2,3,9-trimethyl-6H-thieno[3,2-f][1,2,4]triazolo[4,3-a][1,4]diazepin-6-yl)-N-(6-(4-(3-(2-((2,6-dioxopiperidin-3-yl)amino)-2-oxoethyl)phenyl)piperazin-1-yl)hexyl)acetamide;

2-((S)-4-(4-chlorophenyl)-2,3,9-trimethyl-6H-thieno[3,2-f]
[1,2,4]triazolo[4,3-a][1,4]diazepin-6-yl)-N-(7-(4-(3-(2-
((2,6-dioxopiperidin-3-yl)amino)-2-oxoethyl)phenyl)pip-
erazin-1-yl)heptyl)acetamide;

2-((S)-4-(4-chlorophenyl)-2,3,9-trimethyl-6H-thieno[3,2-f]
[1,2,4]triazolo[4,3-a][1,4]diazepin-6-yl)-N-(8-(4-(3-(2-
((2,6-dioxopiperidin-3-yl)amino)-2-oxoethyl)phenyl)pip-
erazin-1-yl)octyl)acetamide;

2-((S)-4-(4-chlorophenyl)-2,3,9-trimethyl-6H-thieno[3,2-f]
[1,2,4]triazolo[4,3-a][1,4]diazepin-6-yl)-N-(9-(4-(3-(2-
((2,6-dioxopiperidin-3-yl)amino)-2-oxoethyl)phenyl)pip-
erazin-1-yl)nonyl)acetamide;

11-(2-((S)-4-(4-chlorophenyl)-2,3,9-trimethyl-6H-thieno[3,
2-f][1,2,4]triazolo[4,3-a][1,4]diazepin-6-yl)acetamido)-
N-(3-(2-((2,6-dioxopiperidin-3-yl)(methyl)amino)-2-
oxoethyl)phenyl)undecanamide;

2-((S)-4-(4-chlorophenyl)-2,3,9-trimethyl-6H-thieno[3,2-f]
[1,2,4]triazolo[4,3-a][1,4]diazepin-6-yl)-N-(8-(4-(4-(2-
((2,6-dioxopiperidin-3-yl)amino)-2-oxoethyl)phenyl)pip-
erazin-1-yl)octyl)acetamide;

2-((S)-4-(4-chlorophenyl)-2,3,9-trimethyl-6H-thieno[3,2-f]
[1,2,4]triazolo[4,3-a][1,4]diazepin-6-yl)-N-(7-(4-(4-(2-
((2,6-dioxopiperidin-3-yl)amino)-2-oxoethyl)phenyl)pip-
erazin-1-yl)heptyl)acetamide;

11-(2-((S)-4-(4-chlorophenyl)-2,3,9-trimethyl-6H-thieno[3,
2-f][1,2,4]triazolo[4,3-a][1,4]diazepin-6-yl)acetamido)-
N-(3-((2S)-1-((2,6-dioxopiperidin-3-yl)amino)-1-oxo-
propan-2-yl)phenyl)undecanamide;

11-(2-((S)-4-(4-chlorophenyl)-2,3,9-trimethyl-6H-thieno[3,
2-f][1,2,4]triazolo[4,3-a][1,4]diazepin-6-yl)acetamido)-
N-(3-((2R)-1-((2,6-dioxopiperidin-3-yl)amino)-1-oxo-
propan-2-yl)phenyl)undecanamide;

1-(3-(11-(2-((S)-4-(4-chlorophenyl)-2,3,9-trimethyl-6H-
thieno[3,2-f][1,2,4]triazolo[4,3-a][1,4]diazepin-6-yl)ac-
etamido)undecanamido)phenyl)-N-(2,6-dioxopiperidin-
3-yl)cyclopropane-1-carboxamide;

2-((S)-4-(4-chlorophenyl)-2,3,9-trimethyl-6H-thieno[3,2-f]
[1,2,4]triazolo[4,3-a][1,4]diazepin-6-yl)-N-(8-(4-(4-(2-
((2,6-dioxopiperidin-3-yl)amino)-2-oxoethyl)pyridin-2-
yl)piperazin-1-yl)octyl)acetamide 2-(2-(4-(8-(2-((S)-4-(4-chlorophenyl)-2,3,9-trimethyl-6H-
thieno[3,2-f][1,2,4]triazolo[4,3-a][1,4]diazepin-6-yl)ac-
etamido)octyl)piperazin-1-yl)pyridin-4-yl)-N-(2,6-di-
oxopiperidin-3-yl)-N-methylacetamide;

11-(2-((S)-4-(4-chlorophenyl)-2,3,9-trimethyl-6H-thieno[3,
2-f][,2,4]triazolo[4,3-a][1,4]diazepin-6-yl)acetamido)-N-
(3-(2-((2,6-dioxopiperidin-3-yl)amino)-2-oxoethyl)phe-
nyl)undecanamide;

6-(2-((S)-4-(4-chlorophenyl)-2,3,9-trimethyl-6H-thieno[3,
2-f][1,2,4]triazolo[4,3-a][1,4]diazepin-6-yl)acetamido)-
N-(4-(2-((2,6-dioxopiperidin-3-yl)amino)-2-oxoethyl)
phenyl)hexanamide;

6-(2-((S)-4-(4-chlorophenyl)-2,3,9-trimethyl-6H-thieno[3,
2-f][1,2,4]triazolo[4,3-a][1,4]diazepin-6-yl)acetamido)-
N-(3-(2-((2,6-dioxopiperidin-3-yl)amino)-2-oxoethyl)
phenyl)hexanamide; and 11-(2-((S)-4-(4-chlorophenyl)-2,3,9-trimethyl-6H-thieno[3,
2-f][1,2,4]triazolo[4,3-a][1,4]diazepin-6-yl)acetamido)-
N-(4-(2-((2,6-dioxopiperidin-3-yl)amino)-2-oxoethyl)
phenyl)undecanamide.

In some embodiments, provided herein is a compound, or pharmaceutically acceptable salt thereof, chosen from:

(E)-N-(2,6-dioxopiperidin-3-yl)-2-(3-(4-((1-(4-(1-(4-hy-
droxyphenyl)-2-phenylbut-1-en-1-yl)phenyl)piperidin-
4-yl)methyl)piperazin-1-yl)phenyl)-N-methylacet-
amide;

(E)-N-(2,6-dioxopiperidin-3-yl)-2-(2-(4-((1-(4-(1-(4-hy-
droxyphenyl)-2-phenylbut-1-en-1-yl)phenyl)piperidin-4-
yl)methyl)piperazin-1-yl)pyridin-4-yl)-N-methylacet-
amide;

(E)-N-(2,6-dioxopiperidin-3-yl)-2-(2-(4-((1-(4-(1-(4-hy-
droxyphenyl)-2-phenylbut-1-en-1-yl)phenyl)piperidin-4-
yl)methyl)piperazin-1-yl)pyridin-4-yl)acetamide;

(E)-N-(2,6-dioxopiperidin-3-yl)-2-(4-(4-((1-(4-(1-(4-hy-
droxyphenyl)-2-phenylbut-1-en-1-yl)phenyl)piperidin-4-
yl)methyl)piperazin-1-yl)pyridin-2-yl)-N-methylacet-
amide;

(E)-N-(2,6-dioxopiperidin-3-yl)-2-(6-(4-((1-(4-(1-(4-hy-
droxyphenyl)-2-phenylbut-1-en-1-yl)phenyl)piperidin-4-
yl)methyl)piperazin-1-yl)pyridin-2-yl)-N-methylacet-
amide;

(E)-N-(2,6-dioxopiperidin-3-yl)-2-(6-(4-((1-(4-(1-(4-hy-
droxyphenyl)-2-phenylbut-1-en-1-yl)phenyl)piperidin-4-
yl)methyl)piperazin-1-yl)pyridin-2-yl)acetamide;

(E)-N-(2,6-dioxopiperidin-3-yl)-2-(4-(4-((1-(4-(1-(4-hy-
droxyphenyl)-2-phenylbut-1-en-1-yl)phenyl)piperidin-4-
yl)methyl)piperazin-1-yl)phenyl)acetamide;

(E)-N-(2,6-dioxopiperidin-3-yl)-2-(4-(4-((1-(4-(1-(4-hy-
droxyphenyl)-2-phenylbut-1-en-1-yl)phenyl)piperidin-4-
yl)methyl)piperazin-1-yl)phenyl)-N-methylacetamide;

(E)-N-(2,6-dioxopiperidin-3-yl)-2-(6-(4-((1-(4-(1-(4-hy-
droxyphenyl)-2-phenylbut-1-en-1-yl)phenyl)piperidin-4-
yl)methyl)piperazin-1-yl)pyridin-3-yl)-N-methylacet-
amide;

(E)-N-(2,6-dioxopiperidin-3-yl)-2-(5-(4-((1-(4-(1-(4-hy-
droxyphenyl)-2-phenylbut-1-en-1-yl)phenyl)piperidin-4-
yl)methyl)piperazin-1-yl)pyridin-2-yl)-N-methylacet-
amide;

(E)-N-(2,6-dioxopiperidin-3-yl)-2-(3-(4-((1-(4-(1-(4-hy-
droxyphenyl)-2-phenylbut-1-en-1-yl)phenyl)piperidin-4-
yl)methyl)piperazin-1-yl)phenyl)acetamide; and (E)-N-(2,6-dioxopiperidin-3-yl)-2-(2-(4-(2-(1-(4-(1-(4-hy-
droxyphenyl)-2-phenylbut-1-en-1-yl)phenyl)piperidin-4-
yl)ethyl)piperazin-1-yl)pyridin-4-yl)acetamide.

In some embodiments, provided herein is a compound, or pharmaceutically acceptable salt thereof, chosen from:

11-(2-((S)-4-(4-chlorophenyl)-2,3,9-trimethyl-6H-thieno[3,
2-f][1,2,4]triazolo[4,3-a][1,4]diazepin-6-yl)acetamido)-
N-(3-(2-((2,6-dioxopiperidin-3-yl)amino)-2-oxoethyl)
phenyl)undecanamide;

11-(2-((S)-4-(4-chlorophenyl)-2,3,9-trimethyl-6H-thieno[3,
2-f][1,2,4]triazolo[4,3-a][1,4]diazepin-6-yl)acetamido)-
N-(4-(2-((2,6-dioxopiperidin-3-yl)amino)-2-oxoethyl)
phenyl)undecanamide;

7-(2-((S)-4-(4-chlorophenyl)-2,3,9-trimethyl-6H-thieno[3,
2-f][1,2,4]triazolo[4,3-a][1,4]diazepin-6-yl)acetamido)-
N-(4-(2-((2,6-dioxopiperidin-3-yl)amino)-2-oxoethyl)
phenyl)heptanamide; and 6-(2-((S)-4-(4-chlorophenyl)-2,3,9-trimethyl-6H-thieno[3,
2-f][1,2,4]triazolo[4,3-a][1,4]diazepin-6-yl)acetamido)-
N-(3-(2-((2,6-dioxopiperidin-3-yl)amino)-2-oxoethyl)
phenyl)hexanamide.

In some embodiments, provided herein is a compound of Formula (I), (Ia), (Ib), or (Ic), or a tautomer, stereoisomer, pharmaceutically acceptable salt or hydrate thereof.

In some embodiments, provided herein is a compound, or pharmaceutically acceptable salt thereof, chosen from the compounds listed in Table 1.

TABLE 1

Exemplary Compounds of the Present Disclosure

| # | Structure | IUPAC Name |
|---|---|---|
| 253035 | 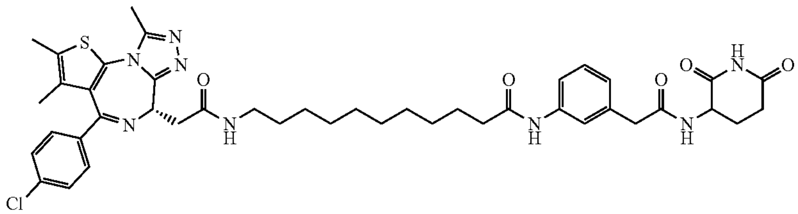 [SMILES: Cc1sc2c(c1C)C(c1ccc(Cl)cc1)=N[C@@H](CC(=O)NCCCCCCCCCCC(=O)Nc1cccc(CC(=O)NC3CCC(=O)NC3=O)c1)c1nnc(C)n1-2] | 11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)amino)-2-oxoethyl)phenyl) undecanamide |
| 253034 | 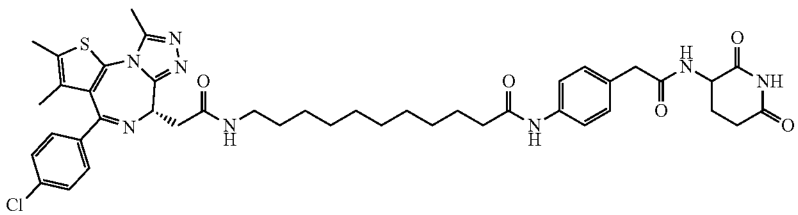 [SMILES: Cc1sc2c(c1C)C(c1ccc(Cl)cc1)=N[C@@H](CC(=O)NCCCCCCCCCCC(=O)Nc1ccc(CC(=O)NC3CCC(=O)NC3=O)cc1)c1nnc(C)n1-2] | 11-(2-((S)-4-(4-chlorophenyl)-2,3,9-trimethyl-6H-thieno[3,2-f][1,2,4]triazolo[4,3-a][1,4]diazepin-6-yl)acetamido)-N-(4-(2-((2,6-dioxopiperidin-3-yl)amino)-2-oxoethyl)phenyl) undecanamide |
| 222174 | 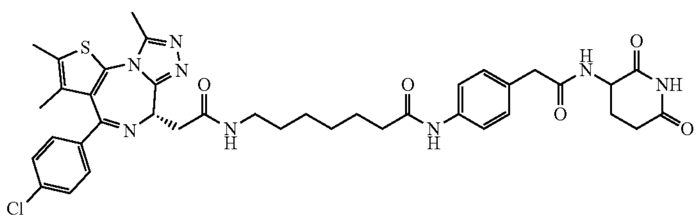 [SMILES: Cc1sc2c(c1C)C(c1ccc(Cl)cc1)=N[C@@H](CC(=O)NCCCCCCC(=O)Nc1ccc(CC(=O)NC3CCC(=O)NC3=O)cc1)c1nnc(C)n1-2] | 7-(2-((S)-4-(4-chlorophenyl)-2,3,9-trimethyl-6H-thieno[3,2-f][1,2,4]triazolo[4,3-a][1,4]diazepin-6-yl)acetamido)-N-(4-(2-((2,6-dioxopiperidin-3-yl)amino)-2-oxoethyl)phenyl)heptanamide; |
| 222175 | 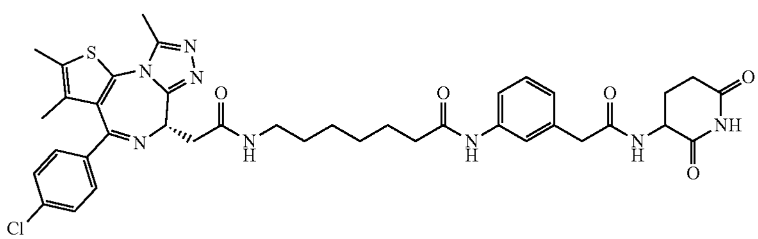 [SMILES: Cc1sc2c(c1C)C(c1ccc(Cl)cc1)=N[C@@H](CC(=O)NCCCCCCC(=O)Nc1cccc(CC(=O)NC3CCC(=O)NC3=O)c1)c1nnc(C)n1-2] | 7-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)amino)-2-oxoethyl)phenyl)heptanamide |
| BET-PRTC1 | 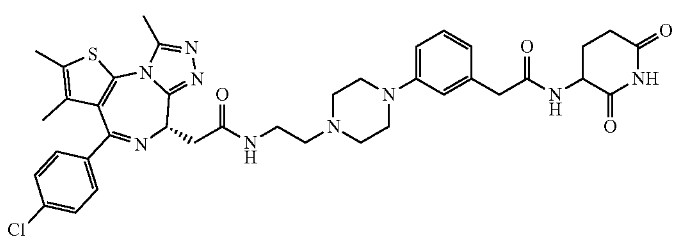 [SMILES: Cc1sc2c(c1C)C(c1ccc(Cl)cc1)=N[C@@H](CC(=O)NCCN1CCN(c3cccc(CC(=O)NC4CCC(=O)NC4=O)c3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(2-(4-(3-(2-((2,6-dioxopiperidin-3-yl)amino)-2-oxoethyl)phenyl)piperazin-1-yl)ethyl)acetamide |
| BET-PRTC2 | 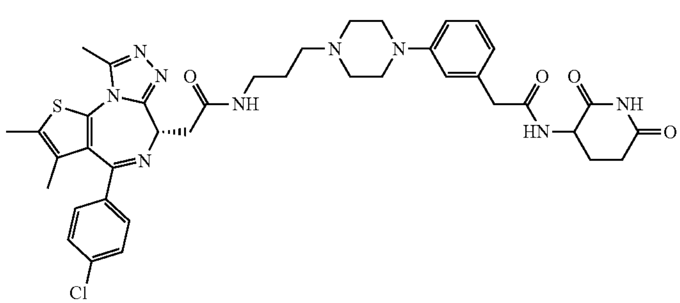 [SMILES: Cc1sc2c(c1C)C(c1ccc(Cl)cc1)=N[C@@H](CC(=O)NCCCN1CCN(c3cccc(CC(=O)NC4CCC(=O)NC4=O)c3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(3-(4-(3-(2-((2,6-dioxopiperidin-3-yl)amino)-2-oxoethyl)phenyl)piperazin-1-yl)propyl)acetamide |

TABLE 1-continued

Exemplary Compounds of the Present Disclosure

| # | Structure | IUPAC Name |
|---|---|---|
| BET-PRTC3 | 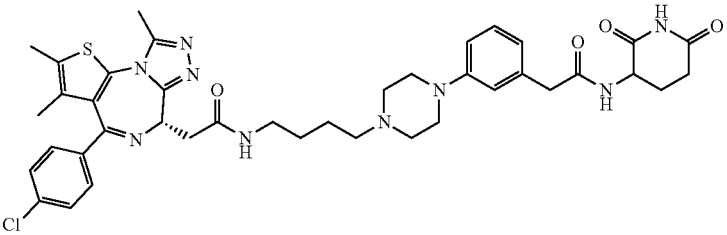 [SMILES: Cc1sc2c(c1C)C(c1ccc(Cl)cc1)=N[C@@H](CC(=O)NCCCCN1CCN(c3cccc(CC(=O)NC4CCC(=O)NC4=O)c3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(4-(4-(3-(2-((2,6-dioxopiperidin-3-yl)amino)-2-oxoethyl)phenyl)piperazin-1-yl)butyl)acetamide |
| BET-PRTC4 | 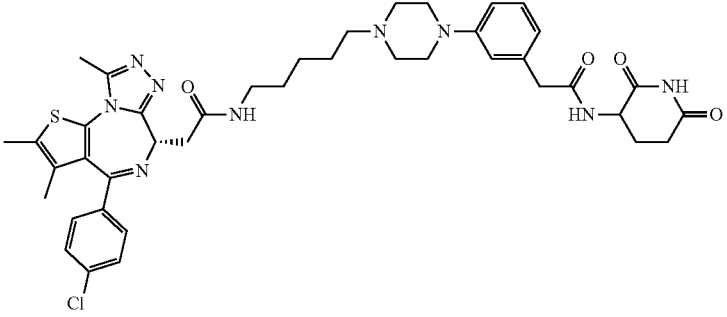 [SMILES: Cc1sc2c(c1C)C(c1ccc(Cl)cc1)=N[C@@H](CC(=O)NCCCCCN1CCN(c3cccc(CC(=O)NC4CCC(=O)NC4=O)c3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(5-(4-(3-(2-((2,6-dioxopiperidin-3-yl)amino)-2-oxoethyl)phenyl)piperazin-1-yl)pentyl)acetamide |
| BET-PRTC5 | 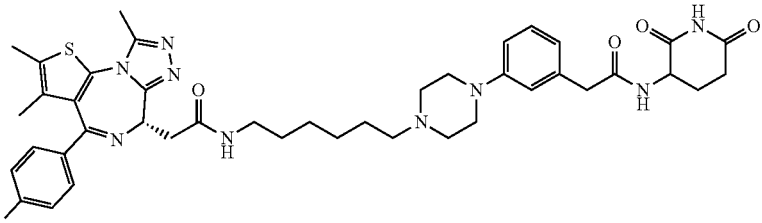 | 2-((S)-4-(4-chlorophenyl)-2,3,9-trimethyl-6H-thieno[3,2-f][1,2,4]triazolo[4,3-a][1,4]diazepin-6-yl)-N-(6-(4-(3-(2-((2,6-dioxopiperidin-3-yl)amino)-2-oxoethyl)phenyl)piperazin-1-yl)hexyl)acetamide |
| BET-PRTC6 | 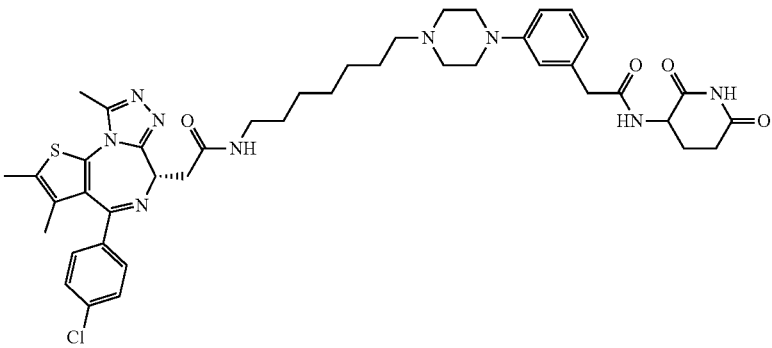 [SMILES: Cc1sc2c(c1C)C(c1ccc(Cl)cc1)=N[C@@H](CC(=O)NCCCCCCCN1CCN(c3cccc(CC(=O)NC4CCC(=O)NC4=O)c3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(7-(4-(3-(2-((2,6-dioxopiperidin-3-yl)amino)-2-oxoethyl)phenyl)piperazin-1-yl)heptyl)acetamide |
| BET-PRTC7 | 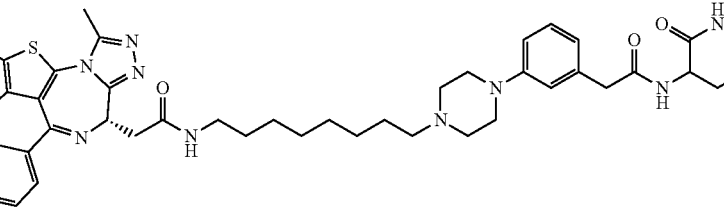 | 2-((S)-4-(4-chlorophenyl)-2,3,9-trimethyl-6H-thieno[3,2-f][1,2,4]triazolo[4,3-a][1,4]diazepin-6-yl)-N-(8-(4-(3-(2-((2,6-dioxopiperidin-3-yl)amino)-2-oxoethyl)phenyl)piperazin-1-yl)octyl)acetamide |

TABLE 1-continued

Exemplary Compounds of the Present Disclosure

| # | Structure | IUPAC Name |
|---|-----------|------------|
| BET-PRTC8 | 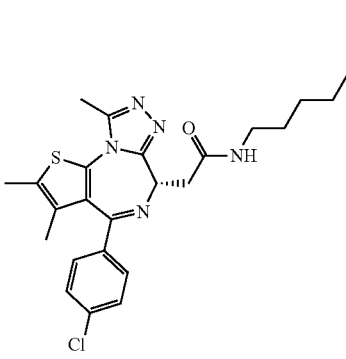 | 2-((S)-4-(4-chlorophenyl)-2,3,9-trimethyl-6H-thieno[3,2-f][1,2,4]triazolo[4,3-a][1,4]diazepin-6-yl)-N-(9-(4-(3-(2-((2,6-dioxopiperidin-3-yl)amino)-2-oxoethyl)phenyl)piperazin-1-yl)nonyl)acetamide |
| BET-PRTC9 | 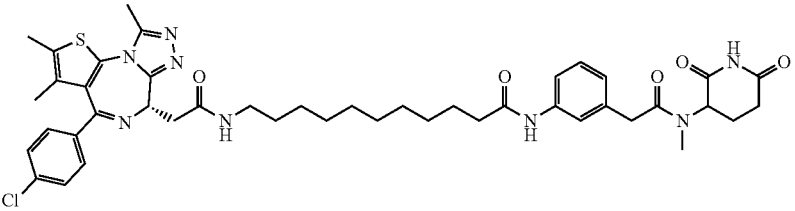 [SMILES: Cc1sc2c(c1C)C(c1ccc(Cl)cc1)=N[C@@H](CC(=O)NCCCCCCCCCCC(=O)Nc1cccc(CC(=O)N(C)C3CCC(=O)NC3=O)c1)c1nnc(C)n1-2] | 11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)(methyl)amino)-2-oxoethyl)phenyl)undecanamide |
| BET-PRTC10 | 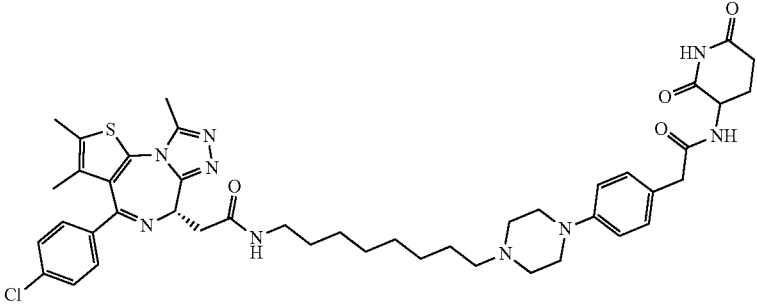 [SMILES: Cc1sc2c(c1C)C(c1ccc(Cl)cc1)=N[C@@H](CC(=O)NCCCCCCCCN1CCN(c3ccc(CC(=O)NC4CCC(=O)NC4=O)cc3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(8-(4-(2-((2,6-dioxopiperidin-3-yl)amino)-2-oxoethyl)phenyl)piperazin-1-yl)octyl)acetamide |
| BET-PRTC11 | 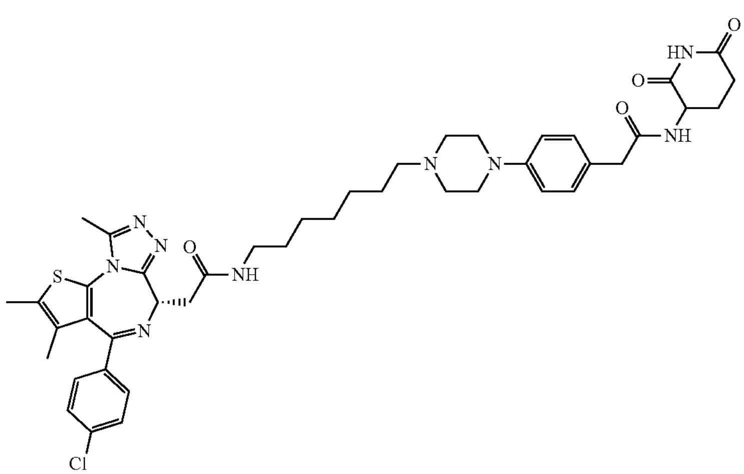 [SMILES: Cc1sc2c(c1C)C(c1ccc(Cl)cc1)=N[C@@H](CC(=O)NCCCCCCCN1CCN(c3ccc(CC(=O)NC4CCC(=O)NC4=O)cc3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(7-(4-(4-(2-((2,6-dioxopiperidin-3-yl)amino)-2-oxoethyl)phenyl)piperazin-1-yl)heptyl)acetamide |

TABLE 1-continued

Exemplary Compounds of the Present Disclosure

| # | Structure | IUPAC Name |
|---|---|---|
| BET-PRTC12 | 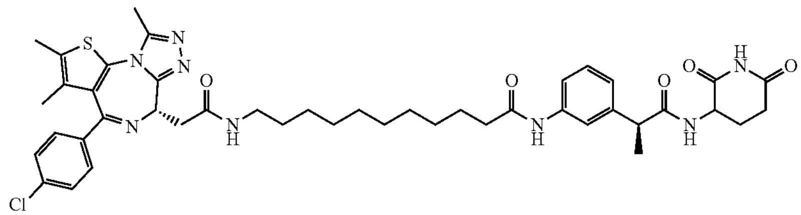 [SMILES: Cc1sc2c(c1C)C(c1ccc(Cl)cc1)=N[C@@H](CC(=O)NCCCCCCCCCCC(=O)Nc1cccc([C@H](C)C(=O)NC3CCC(=O)NC3=O)c1)c1nnc(C)n1-2] | 11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-((2S)-1-((2,6-dioxopiperidin-3-yl)amino)-1-oxopropan-2-yl)phenyl)undecanamide |
| BET-PRTC13 | 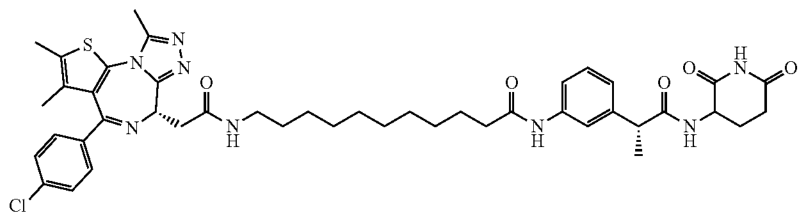 | 11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-((2R)-1-((2,6-dioxopiperidin-3-yl)amino)-1-oxopropan-2-yl)phenyl)undecanamide |
| BET-PRTC14 | 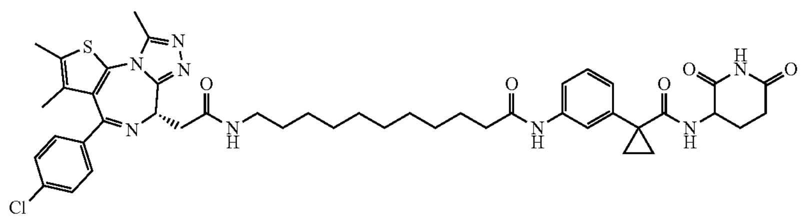 [SMILES: Cc1sc2c(c1C)C(c1ccc(Cl)cc1)=N[C@@H](CC(=O)NCCCCCCCCCCC(=O)Nc1cccc(C3(C(=O)NC4CCC(=O)NC4=O)CC3)c1)c1nnc(C)n1-2] | 1-(3-(11-(2-((S)-4-(4-chlorophenyl)-2,3,9-trimethyl-6H-thieno[3,2-f][1,2,4]triazolo[4,3-a][1,4]diazepin-6-yl)acetamido)undecanamido)phenyl)-N-(2,6-dioxopiperidin-3-yl)cyclopropane-1-carboxamide |
| BET-PRTC15 | 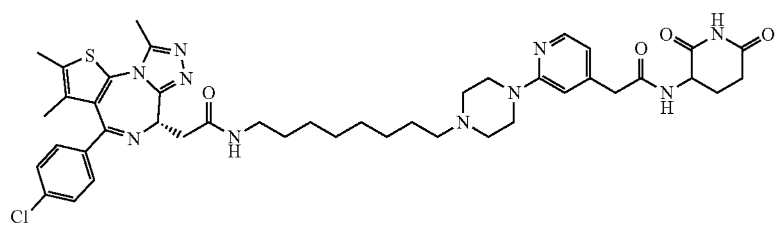 [SMILES: Cc1sc2c(c1C)C(c1ccc(Cl)cc1)=N[C@@H](CC(=O)NCCCCCCCCN1CCN(c3cc(CC(=O)NC4CCC(=O)NC4=O)ccn3)CC1)c1nnc(C)n1-2] | 2-((S)-4-(4-chlorophenyl)-2,3,9-trimethyl-6H-thieno[3,2-f][1,2,4]triazolo[4,3-a][1,4]diazepin-6-yl)-N-(8-(4-(4-(2-((2,6-dioxopiperidin-3-yl)amino)-2-oxoethyl)pyridin-2-yl)piperazin-1-yl)octyl)acetamide |
| BET-PRTC16 | 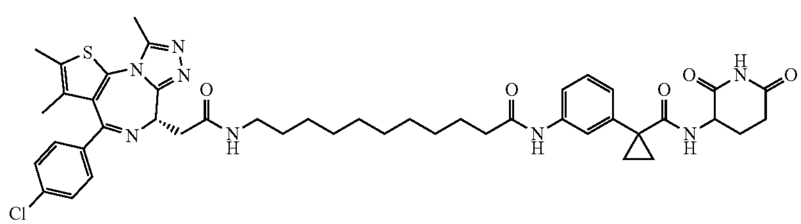 [SMILES: Cc1sc2c(c1C)C(c1ccc(Cl)cc1)=N[C@@H](CC(=O)NCCCCCCCCCCC(=O)Nc1cccc(C3(C(=O)NC4CCC(=O)NC4=O)CC3)c1)c1nnc(C)n1-2] | 2-(2-(4-(8-(2-((S)-4-(4-chlorophenyl)-2,3,9-trimethyl-6H-thieno[3,2-f][1,2,4]triazolo[4,3-a][1,4]diazepin-6-yl)acetamido)octyl)piperazin-1-yl)pyridin-4-yl)-N-(2,6-dioxopiperidin-3-yl)-N-methylacetamide |
| AR-PRTC1 | 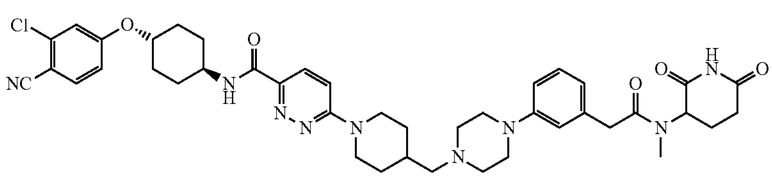 | N-((1r,4r)-4-(3-chloro-4-cyanophenoxy)cyclohexyl)-6-(4-((4-(3-(2-((2,6-dioxopiperidin-3-yl)(methyl)amino)-2-oxoethyl)phenyl)piperazin-1-yl)methyl)piperidin-1-yl)pyridazine-3-carboxamide |
| AR-PRTC2 | 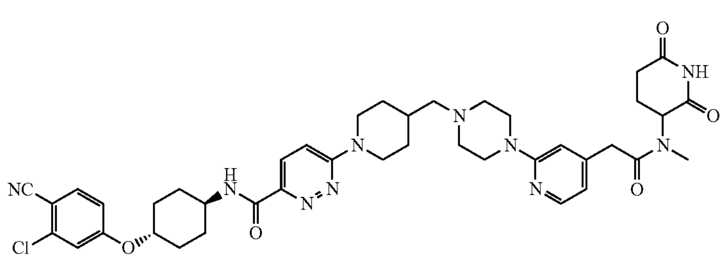 [SMILES: CN(C(=O)Cc1ccnc(N2CCN(CC3CCN(c4ccc(C(=O)N[C@H]5CC[C@H](Oc6ccc(C#N)c(Cl)c6)CC5)nn4)CC3)CC2)c1)C1CCC(=O)NC1=O] | N-((1r,4r)-4-(3-chloro-4-cyanophenoxy)cyclohexyl)-6-(4-((4-(4-(2-((2,6-dioxopiperidin-3-yl)(methyl)amino)-2-oxoethyl)pyridin-2-yl)piperazin-1-yl)methyl)piperidin-1-yl)pyridazine-3-carboxamide |

TABLE 1-continued

Exemplary Compounds of the Present Disclosure

| # | Structure | IUPAC Name |
|---|---|---|
| AR-PRTC3 | 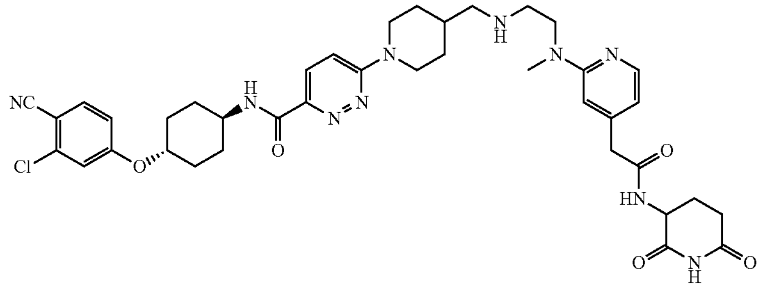 [SMILES: CN(CCNCC1CCN(c2ccc(C(=O)N[C@H]3CC[C@H](Oc4ccc(C#N)c(Cl)c4)CC3)nn2)CC1)c1cc(CC(=O)NC2CCC(=O)NC2=O)ccn1] | N-((1r,4r)-4-(3-chloro-4-cyanophenoxy)cyclohexyl)-6-(4-(((2-((4-(2-((2,6-dioxopiperidin-3-yl)amino)-2-oxoethyl)pyridin-2-yl)(methyl)amino)ethyl)amino)methyl)piperidin-1-yl)pyridazine-3-carboxamide |
| AR-PRTC4 | 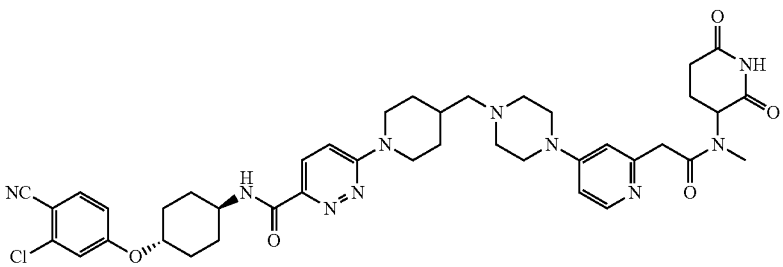 [SMILES: CN(C(=O)Cc1cc(N2CCN(CC3CCN(c4ccc(C(=O)N[C@H]5CC[C@H](Oc6ccc(C#N)c(Cl)c6)CC5)nn4)CC3)CC2)ccn1)C1CCC(=O)NC1=O] | N-((1r,4r)-4-(3-chloro-4-cyanophenoxy)cyclohexyl)-6-(4-((4-(2-(((2,6-dioxopiperidin-3-yl)(methyl)amino)-2-oxoethyl)pyridin-4-yl)piperazin-1-yl)methyl)piperidin-1-yl)pyridazine-3-carboxamide |
| AR-PRTC5 | 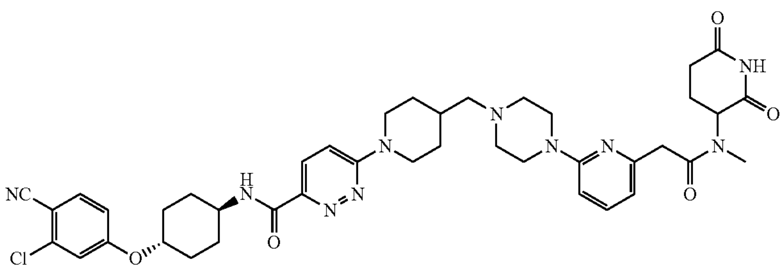 [SMILES: CN(C(=O)Cc1cccc(N2CCN(CC3CCN(c4ccc(C(=O)N[C@H]5CC[C@H](Oc6ccc(C#N)c(Cl)c6)CC5)nn4)CC3)CC2)n1)C1CCC(=O)NC1=O] | N-((1r,4r)-4-(3-chloro-4-cyanophenoxy)cyclohexyl)-6-(4-((4-(6-(2-(((2,6-dioxopiperidin-3-yl)(methyl)amino)-2-oxoethyl)pyridin-2-yl)piperazin-1-yl)methyl)piperidin-1-yl)pyridazine-3-carboxamide |
| AR-PRTC6 | 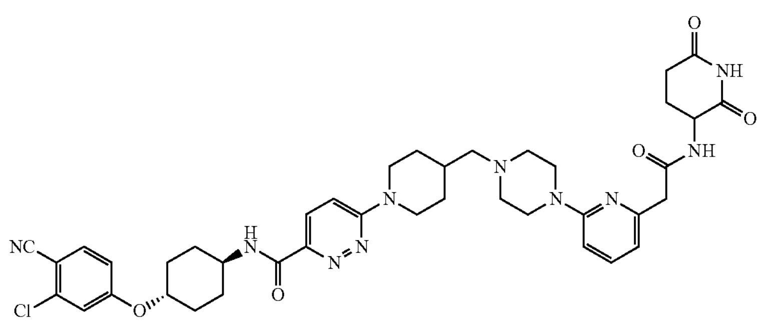 [SMILES: N#Cc1ccc(O[C@H]2CC[C@H](NC(=O)c3ccc(N4CCC(CN5CCN(c6cccc(CC(=O)NC7CCC(=O)NC7=O)n6)CC5)CC4)nn3)CC2)cc1Cl] | N-((1r,4r)-4-(3-chloro-4-cyanophenoxy)cyclohexyl)-6-(4-((4-(6-(2-((2,6-dioxopiperidin-3-yl)amino)-2-oxoethyl)pyridin-2-yl)piperazin-1-yl)methyl)piperidin-1-yl)pyridazine-3-carboxamide |
| AR-PRTC7 | 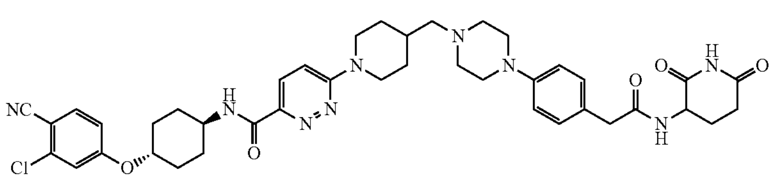 [SMILES: N#Cc1ccc(O[C@H]2CC[C@H](NC(=O)c3ccc(N4CCC(CN5CCN(c6ccc(CC(=O)NC7CCC(=O)NC7=O)cc6)CC5)CC4)nn3)CC2)cc1Cl] | N-((1r,4r)-4-(3-chloro-4-cyanophenoxy)cyclohexyl)-6-(4-((4-(4-(2-((2,6-dioxopiperidin-3-yl)amino)-2-oxoethyl)phenyl)piperazin-1-yl)methyl)piperidin-1-yl)pyridazine-3-carboxamide |
| AR-PRTC8 | 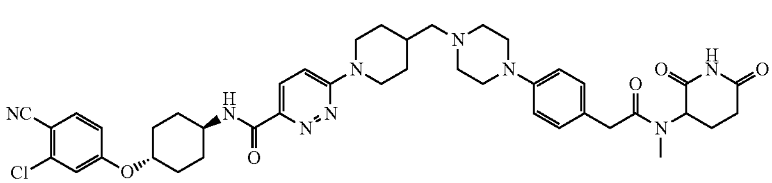 [SMILES: CN(C(=O)Cc1ccc(N2CCN(CC3CCN(c4ccc(C(=O)N[C@H]5CC[C@H](Oc6ccc(C#N)c(Cl)c6)CC5)nn4)CC3)CC2)cc1)C1CCC(=O)NC1=O] | N-((1r,4r)-4-(3-chloro-4-cyanophenoxy)cyclohexyl)-6-(4-((4-(4-(2-(((2,6-dioxopiperidin-3-yl)(methyl)amino)-2-oxoethyl)phenyl)piperazin-1-yl)methyl)piperidin-1-yl)pyridazine-3-carboxamide |

TABLE 1-continued

Exemplary Compounds of the Present Disclosure

| # | Structure | IUPAC Name |
|---|---|---|
| AR-PRTC9 | 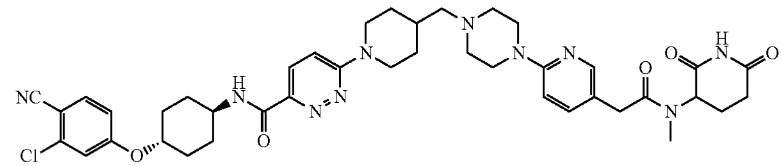 [SMILES: CN(C(=O)Cc1ccc(N2CCN(CC3CCN(c4ccc(C(=O)N[C@H]5CC[C@H](Oc6ccc(C#N)c(Cl)c6)CC5)nn4)CC3)CC2)nc1)C1CCC(=O)NC1=O] | N-((1r,4r)-4-(3-chloro-4-cyanophenoxy)cyclohexyl)-6-(4-((4-(5-(2-((2,6-dioxopiperidin-3-yl)(methyl)amino)-2-oxoethyl)pyridin-2-yl)piperazin-1-yl)methyl)piperidin-1-yl)pyridazine-3-carboxamide |
| AR-PRTC10 | 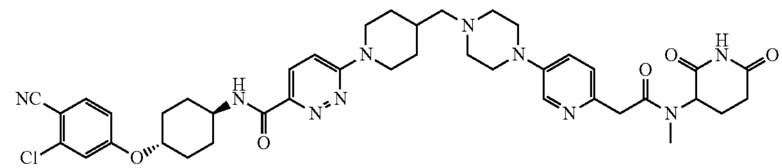 [SMILES: CN(C(=O)Cc1ccc(N2CCN(CC3CCN(c4ccc(C(=O)N[C@H]5CC[C@H](Oc6ccc(C#N)c(Cl)c6)CC5)nn4)CC3)CC2)cn1)C1CCC(=O)NC1=O] | N-((1r,4r)-4-(3-chloro-4-cyanophenoxy)cyclohexyl)-6-(4-((4-(6-(2-((2,6-dioxopiperidin-3-yl)(methyl)amino)-2-oxoethyl)pyridin-3-yl)piperazin-1-yl)methyl)piperidin-1-yl)pyridazine-3-carboxamide |
| AR-PRTC11 | 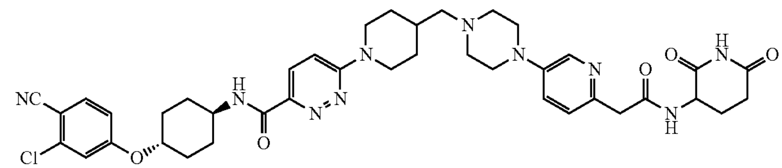 [SMILES: N#Cc1ccc(O[C@H]2CC[C@H](NC(=O)c3ccc(N4CCC(CN5CCN(c6ccc(CC(=O)NC7CCC(=O)NC7=O)nc6)CC5)CC4)nn3)CC2)cc1Cl] | N-((1r,4r)-4-(3-chloro-4-cyanophenoxy)cyclohexyl)-6-(4-((4-(6-(2-((2,6-dioxopiperidin-3-yl)amino)-2-oxoethyl)pyridin-3-yl)piperazin-1-yl)methyl)piperidin-1-yl)pyridazine-3-carboxamide |
| AR-PRTC12 | 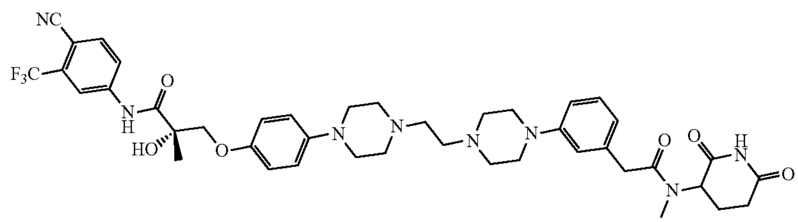 [SMILES: CN(C(=O)Cc1cccc(N2CCN(CCN3CCN(c4ccc(OC[C@](C)(O)C(=O)Nc5ccc(C#N)c(C(F)(F)F)c5)cc4)CC3)CC2)c1)C1CCC(=O)NC1=O] | (2S)-N-(4-cyano-3-(trifluoromethyl)phenyl)-3-(4-(4-(2-(4-(3-(2-((2,6-dioxopiperidin-3-yl)(methyl)amino)-2-oxoethyl)phenyl)piperazin-1-yl)ethyl)piperazin-1-yl)phenoxy)-2-hydroxy-2-methylpropanamide |
| AR-PRTC13 | 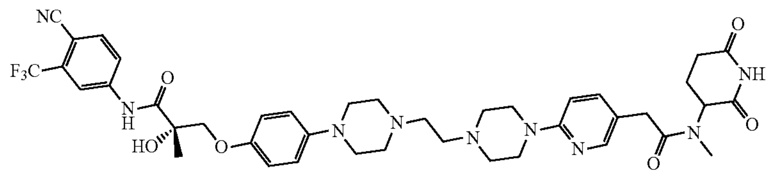 [SMILES: CN(C(=O)Cc1ccc(N2CCN(CCN3CCN(c4ccc(OC[C@](C)(O)C(=O)Nc5ccc(C#N)c(C(F)(F)F)c5)cc4)CC3)CC2)nc1)C1CCC(=O)NC1=O] | (2S)-N-(4-cyano-3-(trifluoromethyl)phenyl)-3-(4-(4-(2-(4-(5-(2-((2,6-dioxopiperidin-3-yl)(methyl)amino)-2-oxoethyl)pyridin-2-yl)piperazin-1-yl)ethyl)piperazin-1-yl)phenoxy)-2-hydroxy-2-methylpropanamide |
| AR-PRTC14 | 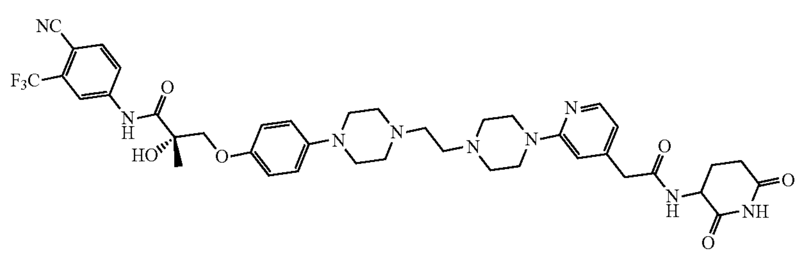 [SMILES: C[C@](O)(COc1ccc(N2CCN(CCN3CCN(c4cc(CC(=O)NC5CCC(=O)NC5=O)ccn4)CC3)CC2)cc1)C(=O)Nc1ccc(C#N)c(C(F)(F)F)c1] | (2S)-N-(4-cyano-3-(trifluoromethyl)phenyl)-3-(4-(4-(2-(4-(4-(2-((2,6-dioxopiperidin-3-yl)amino)-2-oxoethyl)pyridin-2-yl)piperazin-1-yl)ethyl)piperazin-1-yl)phenoxy)-2-hydroxy-2-methylpropanamide |
| AR-PRTC15 | 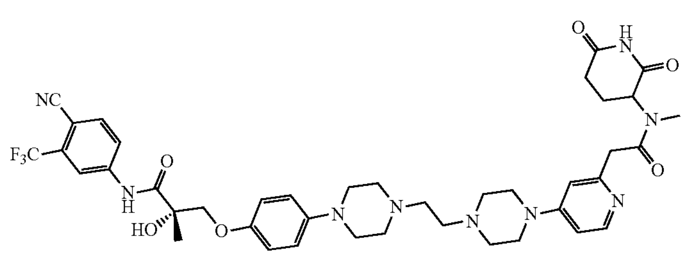 [SMILES: CN(C(=O)Cc1cc(N2CCN(CCN3CCN(c4ccc(OC[C@](C)(O)C(=O)Nc5ccc(C#N)c(C(F)(F)F)c5)cc4)CC3)CC2)ccn1)C1CCC(=O)NC1=O] | (2S)-N-(4-cyano-3-(trifluoromethyl)phenyl)-3-(4-(4-(2-(4-(2-(2-((2,6-dioxopiperidin-3-yl)(methyl)amino)-2-oxoethyl)pyridin-4-yl)piperazin-1-yl)ethyl)piperazin-1-yl)phenoxy)-2-hydroxy-2-methylpropanamide |

TABLE 1-continued

Exemplary Compounds of the Present Disclosure

| # | Structure | IUPAC Name |
|---|---|---|
| AR-PRTC16 | 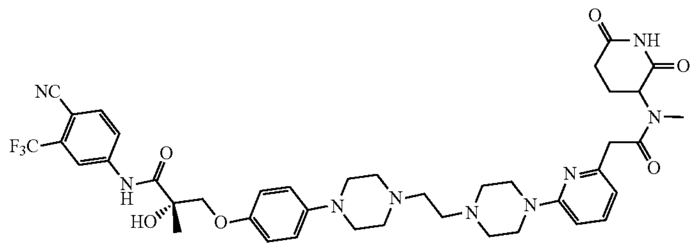 [SMILES: CN(C(=O)Cc1cccc(N2CCN(CCN3CCN(c4ccc(OC[C@](C)(O)C(=O)Nc5ccc(C#N)c(C(F)(F)F)c5)cc4)CC3)CC2)n1)C1CCC(=O)NC1=O] | (2S)-N-(4-cyano-3-(trifluoromethyl)phenyl)-3-(4-(4-(2-(4-(6-(2-((2,6-dioxopiperidin-3-yl)(methyl)amino)-2-oxoethyl)pyridin-2-yl)piperazin-1-yl)ethyl)piperazin-1-yl)phenoxy)-2-hydroxy-2-methylpropanamide |
| AR-PRTC17 | 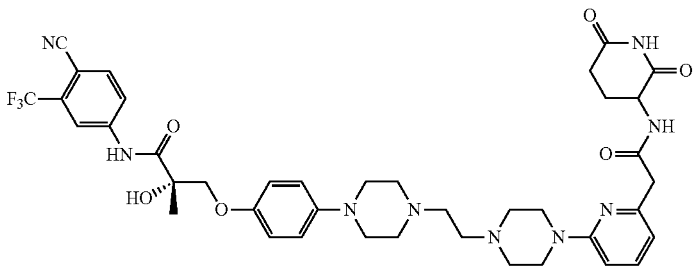 [SMILES: C[C@](O)(COc1ccc(N2CCN(CCN3CCN(c4cccc(CC(=O)NC5CCC(=O)NC5=O)n4)CC3)CC2)cc1)C(=O)Nc1ccc(C#N)c(C(F)(F)F)c1] | (2S)-N-(4-cyano-3-(trifluoromethyl)phenyl)-3-(4-(4-(2-(4-(6-(2-((2,6-dioxopiperidin-3-yl)amino)-2-oxoethyl)pyridin-2-yl)piperazin-1-yl)ethyl)piperazin-1-yl)phenoxy)-2-hydroxy-2-methylpropanamide |
| AR-PRTC18 | 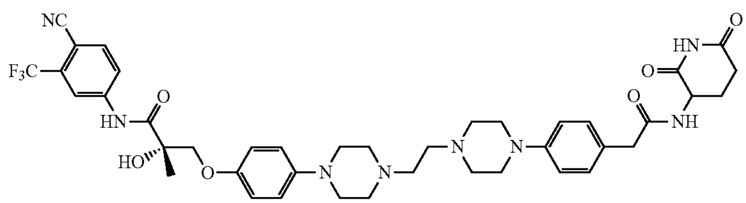 [SMILES: C[C@](O)(COc1ccc(N2CCN(CCN3CCN(c4ccc(CC(=O)NC5CCC(=O)NC5=O)cc4)CC3)CC2)cc1)C(=O)Nc1ccc(C#N)c(C(F)(F)F)c1] | (2S)-N-(4-cyano-3-(trifluoromethyl)phenyl)-3-(4-(4-(2-(4-(4-(2-((2,6-dioxopiperidin-3-yl)amino)-2-oxoethyl)phenyl)piperazin-1-yl)ethyl)piperazin-1-yl)phenoxy)-2-hydroxy-2-methylpropanamide |
| AR-PRTC19 | 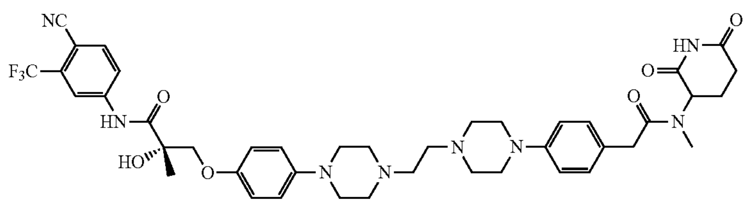 [SMILES: CN(C(=O)Cc1ccc(N2CCN(CCN3CCN(c4ccc(OC[C@](C)(O)C(=O)Nc5ccc(C#N)c(C(F)(F)F)c5)cc4)CC3)CC2)cc1)C1CCC(=O)NC1=O] | (2S)-N-(4-cyano-3-(trifluoromethyl)phenyl)-3-(4-(2-(4-(4-(2-((2,6-dioxopiperidin-3-yl)(methyl)amino)-2-oxoethyl)phenyl)piperazin-1-yl)ethyl)piperazin-1-yl)phenoxy)-2-hydroxy-2-methylpropanamide |
| AR-PRTC20 | 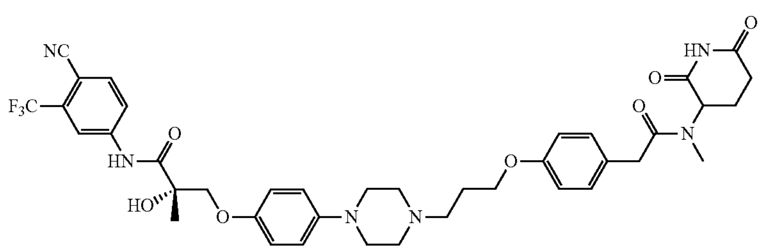 [SMILES: CN(C(=O)Cc1ccc(OCCCN2CCN(c3ccc(OC[C@](C)(O)C(=O)Nc4ccc(C#N)c(C(F)(F)F)c4)cc3)CC2)cc1)C1CCC(=O)NC1=O] | N-(4-cyano-3-(trifluoromethyl)phenyl)-3-(4-(4-(3-(4-(2-((2,6-dioxopiperidin-3-yl)(methyl)amino)-2-oxoethyl)phenoxy)propyl)piperazin-1-yl)phenoxy)-2-hydroxy-2-methylpropanamide |
| AR-PRTC21 | 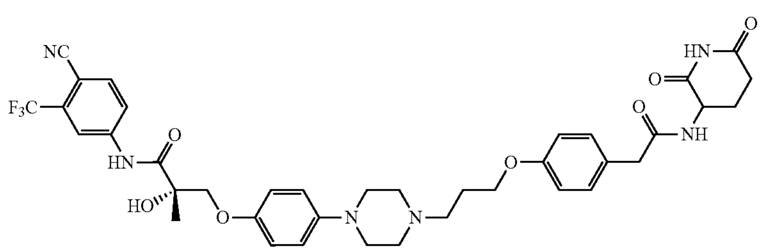 [SMILES: C[C@](O)(COc1ccc(N2CCN(CCCOc3ccc(CC(=O)NC4CCC(=O)NC4=O)cc3)CC2)cc1)C(=O)Nc1ccc(C#N)c(C(F)(F)F)c1] | N-(4-cyano-3-(trifluoromethyl)phenyl)-3-(4-(4-(3-(4-(2-((2,6-dioxopiperidin-3-yl)amino)-2-oxoethyl)phenoxy)propyl)piperazin-1-yl)phenoxy)-2-hydroxy-2-methylpropanamide |
| AR-PRTC22 | 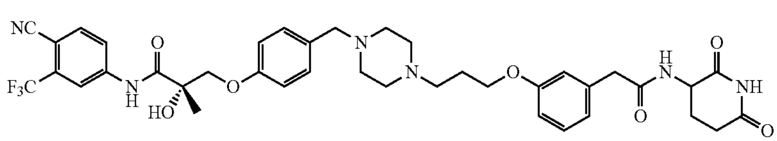 [SMILES: C[C@](O)(COc1ccc(CN2CCN(CCCOc3cccc(CC(=O)NC4CCC(=O)NC4=O)c3)CC2)cc1)C(=O)Nc1ccc(C#N)c(C(F)(F)F)c1] | N-(4-cyano-3-(trifluoromethyl)phenyl)-3-((4-(3-(3-(2-((2,6-dioxopiperidin-3-yl)amino)-2-oxoethyl)phenoxy)propyl)piperazin-1-yl)methyl) |

TABLE 1-continued

Exemplary Compounds of the Present Disclosure

| # | Structure | IUPAC Name |
|---|---|---|
| | | phenoxy)-2-hydroxy-2-methylpropanamide |
| AR-PRTC23 | 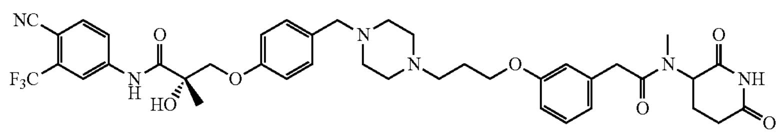 [SMILES: CN(C(=O)Cc1cccc(OCCCN2CCN(Cc3ccc(OC[C@](C)(O)C(=O)Nc4ccc(C#N)c(C(F)(F)F)c4)cc3)CC2)c1)C1CCC(=O)NC1=O] | N-(4-cyano-3-(trifluoromethyl)phenyl)-3-(4-((4-(3-(3-(2-((2,6-dioxopiperidin-3-yl)(methyl)amino)-2-oxoethyl)phenoxy)propyl)piperazin-1-yl)methyl)phenoxy)-2-hydroxy-2-methylpropanamide |
| AR-PRTC24 | 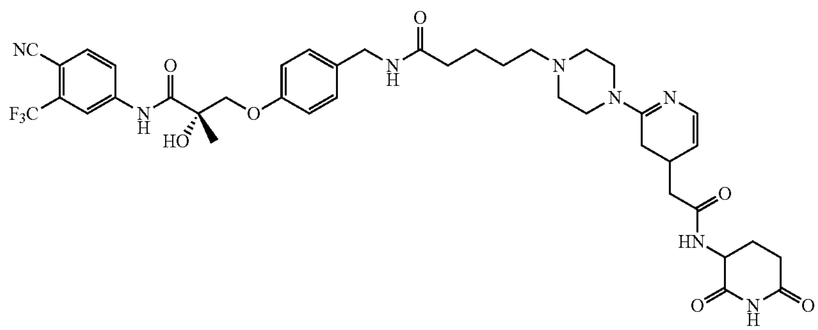 [SMILES: C[C@](O)(COc1ccc(CNC(=O)CCCCN2CCN(C3=NC=CC(CC(=O)NC4CCC(=O)NC4=O)C3)CC2)cc1)C(=O)Nc1ccc(C#N)c(C(F)(F)F)c1] | N-(4-(3-((4-cyano-3-(trifluoromethyl)phenyl)amino)-2-hydroxy-2-methyl-3-oxopropoxy)benzyl)-5-(4-(4-(2-((2,6-dioxopiperidin-3-yl)amino)-2-oxoethyl)-3,4-dihydropyridin-2-yl)piperazin-1-yl)pentanamide |
| AR-PRTC25 | 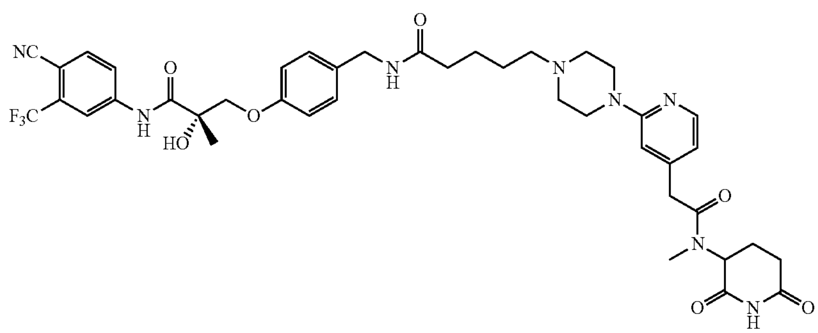 [SMILES: CN(C(=O)Cc1ccnc(N2CCN(CCCCC(=O)NCc3ccc(OC[C@](C)(O)C(=O)Nc4ccc(C#N)c(C(F)(F)F)c4)cc3)CC2)c1)C1CCC(=O)NC1=O] | N-(4-(3-((4-cyano-3-(trifluoromethyl)phenyl)amino)-2-hydroxy-2-methyl-3-oxopropoxy)benzyl)-5-(4-(4-(2-((2,6-dioxopiperidin-3-yl)(methyl)amino)-2-oxoethyl)pyridin-2-yl)piperazin-1-yl)pentanamide |
| AR-PRTC26 | 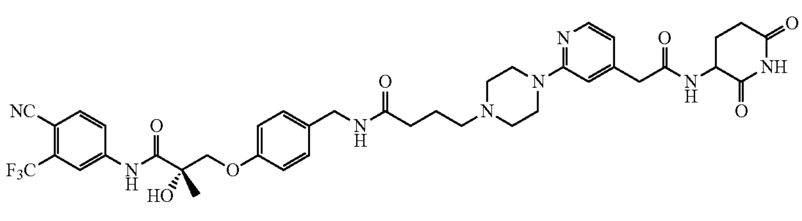 [SMILES: CN(C(=O)Cc1ccnc(N2CCN(CCCC(=O)NCc3ccc(OC[C@](C)(O)C(=O)Nc4ccc(C#N)c(C(F)(F)F)c4)cc3)CC2)c1)C1CCC(=O)NC1=O] | N-(4-((S)-3-((4-cyano-3-(trifluoromethyl)phenyl)amino)-2-hydroxy-2-methyl-3-oxopropoxy)benzyl)-4-(4-(4-(2-((2,6-dioxopiperidin-3-yl)amino)-2-oxoethyl)pyridin-2-yl)piperazin-1-yl)butanamide |
| AR-PRTC27 | 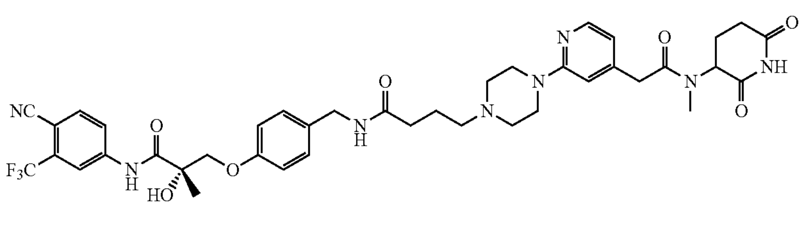 | N-(4-((S)-3-((4-cyano-3-(trifluoromethyl)phenyl)amino)-2-hydroxy-2-methyl-3-oxopropoxy)benzyl)-4-(4-(4-(2-((2,6-dioxopiperidin-3-yl)(methyl)amino)-2-oxoethyl)pyridin-2-yl)piperazin-1-yl)butanamide |

TABLE 1-continued

Exemplary Compounds of the Present Disclosure

| # | Structure | IUPAC Name |
|---|---|---|
| ER-PRTC1 | 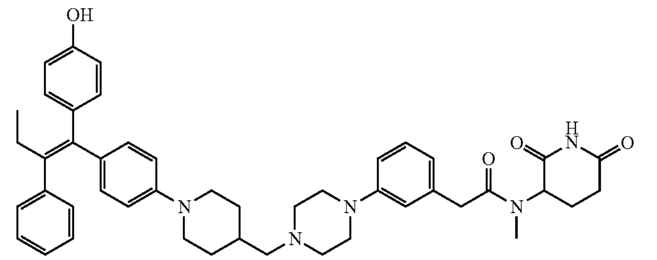 [SMILES: CC/C(=C(\c1ccc(O)cc1)c1ccc(N2CCC(CN3CCN(c4cccc(CC(=O)N(C)C5CCC(=O)NC5=O)c4)CC3)CC2)cc1)c1ccccc1] | (E)-N-(2,6-dioxopiperidin-3-yl)-2-(3-(4-((1-(4-(1-(4-hydroxyphenyl)-2-phenylbut-1-en-1-yl)phenyl)piperidin-4-yl)methyl)piperazin-1-yl)phenyl)-N-methylacetamide |
| ER-PRTC2 | 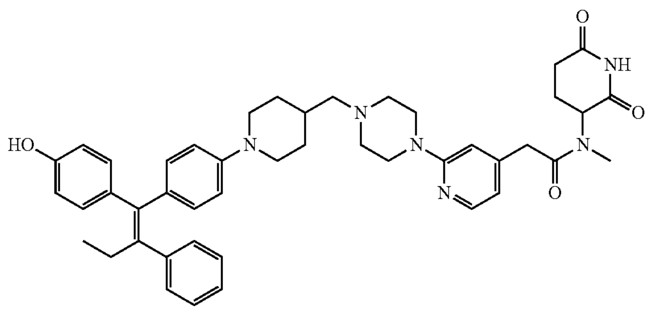 [SMILES: CC/C(=C(\c1ccc(O)cc1)c1ccc(N2CCC(CN3CCN(c4cc(CC(=O)N(C)C5CCC(=O)NC5=O)ccn4)CC3)CC2)cc1)c1ccccc1] | (E)-N-(2,6-dioxopiperidin-3-yl)-2-(2-(4-((1-(4-(1-(4-hydroxyphenyl)-2-phenylbut-1-en-1-yl)phenyl)piperidin-4-yl)methyl)piperazin-1-yl)pyridin-4-yl)-N-methylacetamide |
| ER-PRTC3 | 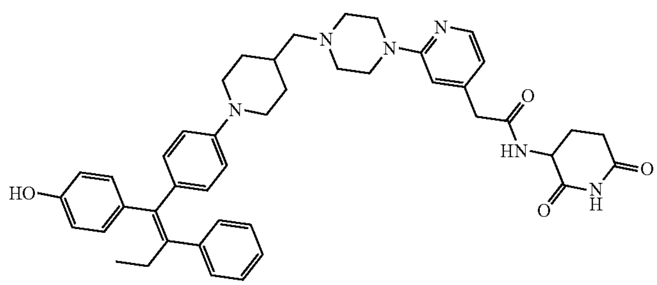 [SMILES: CC/C(=C(\c1ccc(O)cc1)c1ccc(N2CCC(CN3CCN(c4cc(CC(=O)NC5CCC(=O)NC5=O)ccn4)CC3)CC2)cc1)c1ccccc1] | (E)-N-(2,6-dioxopiperidin-3-yl)-2-(2-(4-((1-(4-(1-(4-hydroxyphenyl)-2-phenylbut-1-en-1-yl)phenyl)piperidin-4-yl)methyl)piperazin-1-yl)pyridin-4-yl)acetamide |
| ER-PRTC4 | 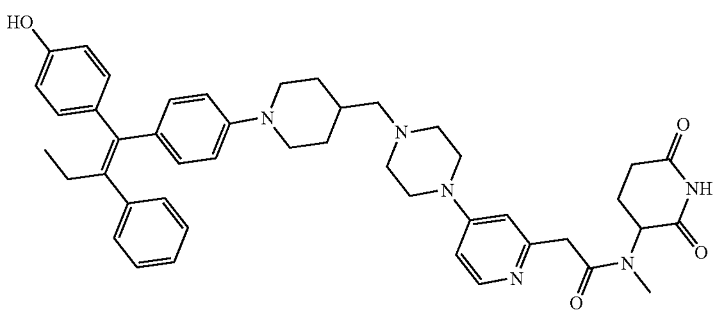 [SMILES: CC/C(=C(\c1ccc(O)cc1)c1ccc(N2CCC(CN3CCN(c4ccnc(CC(=O)N(C)C5CCC(=O)NC5=O)c4)CC3)CC2)cc1)c1ccccc1] | (E)-N-(2,6-dioxopiperidin-3-yl)-2-(4-(4-((1-(4-(1-(4-hydroxyphenyl)-2-phenylbut-1-en-1-yl)phenyl)piperidin-4-yl)methyl)piperazin-1-yl)pyridin-2-yl)-N-methylacetamide |
| ER-PRTC5 | 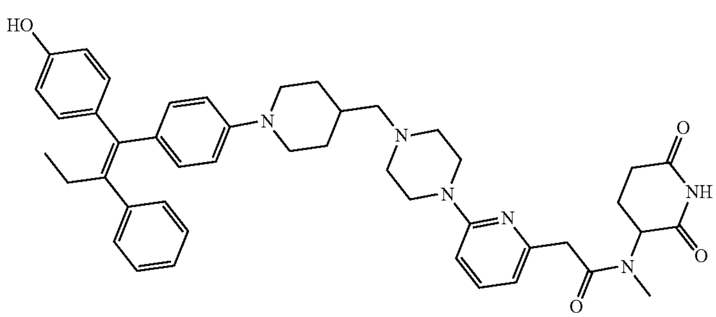 [SMILES: CC/C(=C(\c1ccc(O)cc1)c1ccc(N2CCC(CN3CCN(c4cccc(CC(=O)N(C)C5CCC(=O)NC5=O)n4)CC3)CC2)cc1)c1ccccc1] | (E)-N-(2,6-dioxopiperidin-3-yl)-2-(6-(4-(((1-(4-(1-(4-hydroxyphenyl)-2-phenylbut-1-en-1-yl)phenyl)piperidin-4-yl)methyl)piperazin-1-yl)pyridin-2-yl)-N-methylacetamide |

TABLE 1-continued

Exemplary Compounds of the Present Disclosure

| # | Structure | IUPAC Name |
|---|-----------|------------|
| ER-PRTC6 | 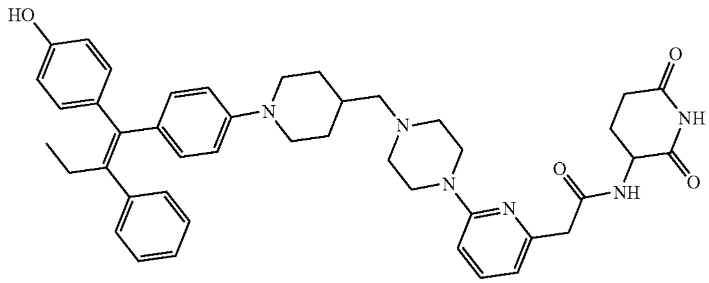 [SMILES: CC/C(=C(\c1ccc(O)cc1)c1ccc(N2CCC(CN3CCN(c4cccc(CC(=O)NC5CCC(=O)NC5=O)n4)CC3)CC2)cc1)c1ccccc1] | (E)-N-(2,6-dioxopiperidin-3-yl)-2-(6-(4-((1-(4-(1-(4-hydroxyphenyl)-2-phenylbut-1-en-1-yl)phenyl)piperidin-4-yl)methyl)piperazin-1-yl)pyridin-2-yl)acetamide |
| ER-PRTC7 | 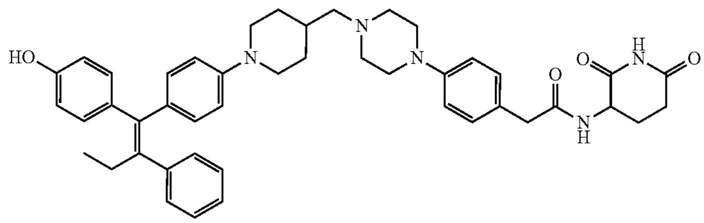 | (E)-N-(2,6-dioxopiperidin-3-yl)-2-(4-(4-((1-(4-(1-(4-hydroxyphenyl)-2-phenylbut-1-en-1-yl)phenyl)piperidin-4-yl)methyl)piperazin-1-yl)phenyl)acetamide |
| ER-PRTC8 | 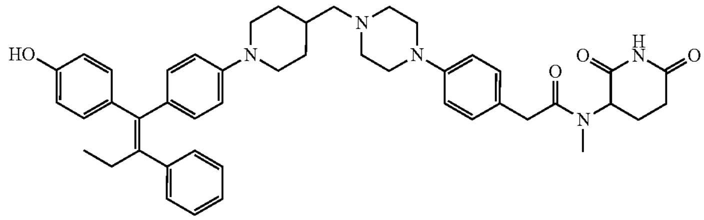 [SMILES: CC/C(=C(\c1ccc(O)cc1)c1ccc(N2CCC(CN3CCN(c4ccc(CC(=O)N(C)C5CCC(=O)NC5=O)cc4)CC3)CC2)cc1)c1ccccc1] | (E)-N-(2,6-dioxopiperidin-3-yl)-2-(4-(4-((1-(4-(1-(4-hydroxyphenyl)-2-phenylbut-1-en-1-yl)phenyl)piperidin-4-yl)methyl)piperazin-1-yl)phenyl)-N-methylacetamide |
| ER-PRTC9 | 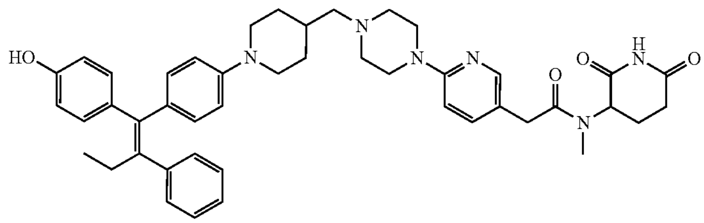 [SMILES: CC/C(=C(\c1ccc(O)cc1)c1ccc(N2CCC(CN3CCN(c4ccc(CC(=O)N(C)C5CCC(=O)NC5=O)cn4)CC3)CC2)cc1)c1ccccc1] | (E)-N-(2,6-dioxopiperidin-3-yl)-2-(6-(4-((1-(4-(1-(4-hydroxyphenyl)-2-phenylbut-1-en-1-yl)phenyl)piperidin-4-yl)methyl)piperazin-1-yl)pyridin-3-yl)-N-methylacetamidex' |
| ER-PRTC10 | 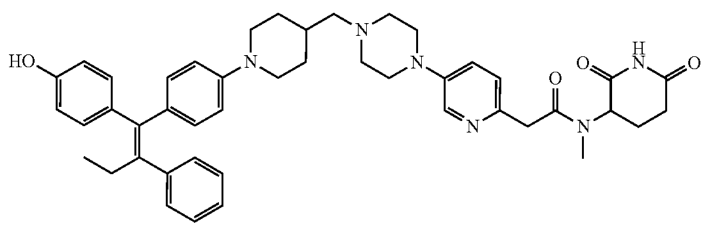 [SMILES: CC/C(=C(\c1ccc(O)cc1)c1ccc(N2CCC(CN3CCN(c4ccc(CC(=O)N(C)C5CCC(=O)NC5=O)nc4)CC3)CC2)cc1)c1ccccc1] | (E)-N-(2,6-dioxopiperidin-3-yl)-2-(5-(4-((1-(4-(1-(4-hydroxyphenyl)-2-phenylbut-1-en-1-yl)phenyl)piperidin-4-yl)methyl)piperazin-1-yl)pyridin-2-yl)-N-methylacetamide |
| ER-PRTC11 | 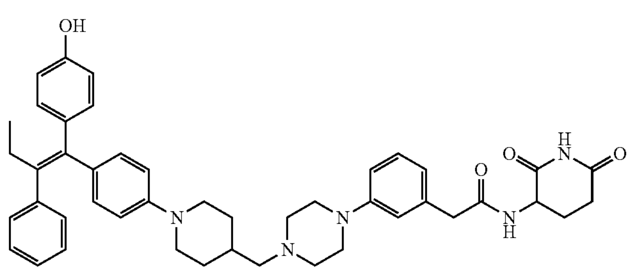 | (E)-N-(2,6-dioxopiperidin-3-yl)-2-(3-(4-((1-(4-(1-(4-hydroxyphenyl)-2-phenylbut-1-en-1-yl)phenyl)piperidin-4-yl)methyl)piperazin-1-yl)phenyl)acetamide |

TABLE 1-continued

Exemplary Compounds of the Present Disclosure

| # | Structure | IUPAC Name |
|---|-----------|------------|
| ER-PRTC12 | 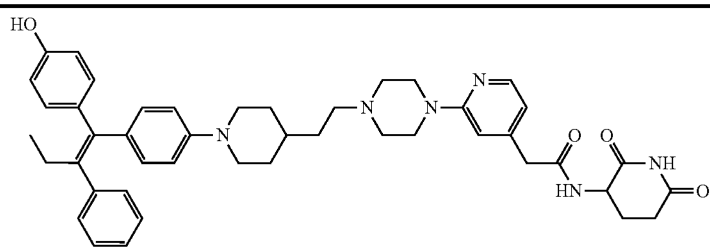 | (E)-N-(2,6-dioxopiperidin-3-yl)-2-(2-(4-(2-(1-(4-(1-(4-hydroxyphenyl)-2-phenylbut-1-en-1-yl)phenyl)piperidin-4-yl)ethyl)piperazin-1-yl)pyridin-4-yl)acetamide |

Pharmaceutical Compositions

Pharmaceutical compositions of the present disclosure comprise at least one compound of Formulae (I), (Ia), (Ib), or (Ic), or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (I), (Ia), (Ib), or (Ic), or pharmaceutically acceptable salts thereof, which are approximately isotonic with the blood of the intended recipient. These preparations are administered intravenously, although administration may also be affected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (I), (Ia), (Ib), or (Ic), or pharmaceutically acceptable salts thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 µg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

TABLE 2

Equivalent Surface Area Dosage Factors.

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | ½ | ¼ | 1/7 |
| Monkey | 4 | 2 | 1 | ⅗ | ⅓ |
| Dog | 6 | 4 | ⅗ | 1 | ½ |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formula (I), (Ia), (Ib), or (Ic), or a tautomer, stereoisomer, pharmaceutically acceptable salt or hydrate thereof, is administered to treat abnormal cellular proliferation, a tumor, cancer, an immune disorder, autoimmune disorder, arthritis, lupus, diabetes, cardiovascular disease, an infectious disease, sepsis, or an inflammatory condition in a subject in need thereof.

In some embodiments, a pharmaceutical composition comprising a compound of Formula (I), (Ia), (Ib), or (Ic), or a tautomer, stereoisomer, pharmaceutically acceptable salt or hydrate thereof, is administered to treat abnormal cellular proliferation, a tumor, cancer, an immune disorder, autoimmune disorder, arthritis, lupus, diabetes, cardiovascular disease, an infectious disease, sepsis, or an inflammatory condition in a subject in need thereof.

In some embodiments, the infectious disease is chosen from HIV, HBV, HCV, HSV, HPV, RSV, CMV, Ebola, Flavivirus, Pestivirus, Rotavirus, Influenza, Coronavirus, EBV, viral pneumonia, drug-resistant viruses, bird flu, RNA virus, DNA virus, adenovirus, poxvirus, meningitis, Picornavirus, Togavirus, Orthomyxovirus, Retrovirus, Hepadnovirus, gram-negative bacteria, gram-positive bacteria, atypical bacteria, *Staphylococcus, Streptococcus, E. coli, Salmonella, Helicobacter pylori*, gonorrhea, Chlamydiaceae, Mycoplasmataceae, fungus, protozoa helminth, worms, or a parasite. In some embodiments, the infectious disease is HIV.

In some embodiments, the cancer is selected from melanoma, breast cancer, prostate cancer, lung cancer, neuroblastoma, glioblastoma, hematologic malignancy, squamous-cell carcinoma, NUT carcinoma, basal cell carcinoma, adenocarcinoma, bladder cancer, bowel cancer, cervical cancer, colon cancer, esophageal cancer, head and neck cancer, kidney cancer, renal cell carcinoma, liver cancer, hepatocellular carcinoma, ovarian cancer, pancreatic cancer, stomach cancer, sarcoma, hemangiosarcoma, Kaposi's sarcoma, liposarcoma, myosarcoma, peripheral neuroepithelioma, synovial sarcoma, glioma, astrocytoma, oligodendroglioma, ependymoma, ganglioneuroma, ganglioglioma, medulloblastoma, pineal cell tumor, meningioma, meningeal sarcoma, neurofibroma, Schwannoma, uterine cancer, testicular cancer, thyroid cancer, carcinosarcoma, Wilms' tumor and teratocarcinoma. In some embodiments, the cancer is a hematologic malignancy. In some embodiments the hematologic malignancy is lymphoma, multiple myeloma, leukemia, myelodysplastic syndrome, or myeloproliferative neoplasms. In some embodiments, the cancer is leukemia. In some embodiments, the leukemia is acute myeloid leukemia. In some embodiments, the leukemia is acute lymphoblastic leukemia. In some embodiments, the leukemia is chronic myeloid leukemia. In some embodiments, the cancer is lymphoma. In some embodiments, the lymphoma is large B-cell lymphoma. In some embodiments, the lymphoma is peripheral T cell lymphoma. In some embodiments, the lymphoma is Burkitt's Lymphoma. In some embodiments, the lymphoma is Hodgkin's lymphoma. In some embodiments, the cancer is prostate cancer. In some embodiments, the prostate cancer is castrate-resistant prostate cancer. In some embodiments, the cancer is lung cancer. In some embodiments, the lung cancer is small cell lung cancer. In some embodiments, the lung cancer is non-small cell lung cancer. In some embodiments, the cancer is breast cancer. In some embodiments, the breast cancer is ER positive breast cancer. In some embodiments, the breast cancer is triple negative breast cancer.

In some embodiments, the subject suffering from cancer has been previously treated with an anti-cancer agent. In some embodiments, the anti-cancer agent may be selected from exemestane, fulvestrant, enzalutamide, a γ-secretase inhibitor, a RAF-inhibitor, an aromatase inhibitor, a selective estrogen modulator (SERM), a selective estrogen receptor down regulator (SERD), luteinizing hormone-releasing hormone superagonists, CYP17 inhibitor Abiraterone, and a small molecule antagonist that blocks the androgen/AR interaction. In some embodiments, the RAF-inhibitor may be vemurafenib. In some embodiments, the aromatase inhibitor may be letrozole or anastrozole. In some embodiments, the SERM may be tamoxifen, toremifene, or raloxifene. In some embodiments, the SERD may be fulvestrant. In some embodiments, the small molecule antagonist that blocks AR/androgen interaction is flutamide, bicalutamide, enzalutamide, apalutamide, or darolutamide.

In some embodiments, provided herein is a use of a compound of Formula (I), (Ia), (Ib), or (Ic), or a pharmaceutically acceptable salt thereof, in a therapeutic treatment. In some embodiments, the therapeutic treatment is for the treatment of abnormal cellular proliferation, a tumor, cancer, an immune disorder, autoimmune disorder, arthritis, lupus, diabetes, cardiovascular disease, an infectious disease, sepsis, or an inflammatory condition in a subject in need thereof.

In some embodiments, the therapeutic treatment is for the treatment of an infectious disease. In some embodiments, the infectious disease is chosen from HIV, HBV, HCV, HSV, HPV, RSV, CMV, Ebola, Flavivirus, Pestivirus, Rotavirus, Influenza, Coronavirus, EBV, viral pneumonia, drug-resistant viruses, bird flu, RNA virus, DNA virus, adenovirus, poxvirus, meningitis, Picornavirus, Togavirus, Orthomyxovirus, Retrovirus, Hepadnovirus, Gram-negative bacteria, Gram-positive bacteria, Atypical bacteria, *Staphylococcus, Streptococcus, E. coli, Salmonella, Helicobacter pylori*, gonorrhea, Chlamydiaceae, Mycoplasmataceae, fungus, protozoa helminth, worms, or parasite. In some embodiments, the infectious disease is HIV.

In some embodiments, the therapeutic treatment is for the treatment of cancer. In some embodiments, the cancer is selected from melanoma, breast cancer, prostate cancer, lung cancer, neuroblastoma, glioblastoma, hematologic malignancy, squamous-cell carcinoma, NUT carcinoma, basal cell carcinoma, adenocarcinoma, bladder cancer, bowel cancer, cervical cancer, colon cancer, esophageal cancer, head and neck cancer, kidney cancer, renal cell carcinoma, liver cancer, hepatocellular carcinoma, ovarian cancer, pancreatic cancer, stomach cancer, sarcoma, hemangiosarcoma, Kaposi's sarcoma, liposarcoma, myosarcoma, peripheral neuroepithelioma, synovial sarcoma, glioma, astrocytoma, oligodendroglioma, ependymoma, ganglioneuroma, ganglioglioma, medulloblastoma, pineal cell tumor, meningioma, meningeal sarcoma, neurofibroma, Schwannoma, uterine cancer, testicular cancer, thyroid cancer, carcinosarcoma, Wilms' tumor and teratocarcinoma. In some embodiments, the cancer is a hematologic malignancy. In some embodiments the hematologic malignancy is lymphoma, multiple myeloma, leukemia, myelodysplastic syndrome, or myeloproliferative neoplasms. In some embodiments, the cancer is leukemia. In some embodiments, the leukemia is acute myeloid leukemia. In some embodiments, the leukemia is acute lymphoblastic leukemia. In some embodiments, the leukemia is chronic myeloid leukemia. In some embodiments, the cancer is lymphoma. In some embodiments, the lymphoma is large B-cell lymphoma. In some embodiments, the lymphoma is peripheral T cell lymphoma. In some embodiments, the lymphoma is Burkitt's Lymphoma. In some embodiments, the lymphoma is Hodgkin's lymphoma.

In some embodiments, the cancer is prostate cancer. In some embodiments, the prostate cancer is castrate-resistant prostate cancer. In some embodiments, the cancer is lung cancer. In some embodiments, the lung cancer is small cell lung cancer. In some embodiments, the lung cancer is non-small cell lung cancer. In some embodiments, the cancer is breast cancer. In some embodiments, the breast cancer is ER positive breast cancer. In some embodiments, the breast cancer is triple negative breast cancer. In some embodiments, the subject suffering from cancer has been previously treated with an anti-cancer agent. In some embodiments, the anti-cancer agent may be selected from exemestane, fulvestrant, enzalutamide, a γ-secretase inhibitor, a RAF-inhibitor, an aromatase inhibitor, a selective estrogen modulator (SERM), a selective estrogen receptor down regulator (SERD), luteinizing hormone-releasing hormone superagonists, CYP17 inhibitor Abiraterone, and a small molecule antagonist that blocks the androgen/AR interaction. In some embodiments, the RAF-inhibitor may be vemurafenib. In some embodiments, the aromatase inhibitor may be letrozole or anastrozole. In some embodiments, the SERM may be tamoxifen, toremifene, or raloxifene. In some embodiments, the SERD may be fulvestrant. In some embodiments, the small molecule antagonist that blocks AR/androgen interaction is flutamide, bicalutamide, enzalutamide, apalutamide, or darolutamide. In some embodiments, the RAF-inhibitor is vemurafenib.

In some embodiments, provided herein is a use of a compound of Formula (I), (Ia), (Ib), or (Ic), or a pharmaceutically acceptable salt thereof, in the preparation of a medicament. In some embodiments, provided herein is a method of inhibiting cell growth comprising contacting a cell with a compound of Formula (I), (Ia), (Ib), or (Ic), or a pharmaceutically acceptable salt thereof. In some embodiments, the cell may be a cancer cell.

In one embodiment, a compound of Formula (I), (Ia), (Ib), or (Ic), or a pharmaceutically acceptable salt thereof is administered in combination with another therapeutic agent. The other therapeutic agent can provide additive or synergistic value relative to the administration of a compound of the present disclosure alone. The therapeutic agent can be selected from, for example, hormones and hormonal analogues; signal transduction pathway inhibitors; topoisomerase I inhibitors; topoisomerase II inhibitors; antimetabolite neoplastic agents; antibiotic neoplastic agents; alkylating agents; anti-microtubule agents; platinum coordination complexes; aromatase inhibitors; and anti-mitotic agents.

In some embodiments, the therapeutic agent may be a hormone or hormonal analogue. In some embodiments, the therapeutic agent may be a signal transduction pathway inhibitor. In some embodiments, the therapeutic agent may be a topoisomerase I inhibitor. In some embodiments, the therapeutic agent may be a topoisomerase II inhibitor. In some embodiments, the therapeutic agent may be an antimetabolite neoplastic agent. In some embodiments, the therapeutic agent may be an antibiotic neoplastic agent. In some embodiments, the therapeutic agent may be an alkylating agent. In some embodiments, the therapeutic agent may be an anti-microtubule agent. In some embodiments, the therapeutic agent may be a platinum coordination complex. In some embodiments, the therapeutic agent may be an aromatase inhibitor. In some embodiments, the therapeutic agent may be an anti-mitotic agent.

In some embodiments, the aromatase inhibitor may be selected from anastrazole, letrozole, vorozole, fadrozole, exemestane, and formestane. In some embodiments, the aromatase inhibitor is anastrazole. In some embodiments, the aromatase inhibitor may be letrozole. In some embodiments, the aromatase inhibitor may be vorozole. In some embodiments, the aromatase inhibitor may be fadrozole. In some embodiments, the aromatase inhibitor may be exemestane. In some embodiments, the aromatase inhibitor may be formestane.

In some embodiments, the anti-mitotic agent may be selected from paclitaxel, docetaxel, and Abraxane. In some embodiments, the anti-mitotic agent may be paclitaxel. In some embodiments, the anti-mitotic agent may be docetaxel. In some embodiments, the anti-mitotic agent may be Abraxane.

In some embodiments, a compound of Formula (I), (Ia), (Ib), or (Ic), or a pharmaceutically acceptable salt thereof, may be administered in combination with a hormone or hormonal analog. In some embodiments, a compound of Formula (I), (Ia), (Ib), or (Ic), or a pharmaceutically acceptable salt thereof, may be administered in combination with a signal transduction pathway inhibitor. In some embodiments, a compound of Formula (I), (Ia), (Ib), or (Ic), or a pharmaceutically acceptable salt thereof, may be administered in combination with an antimetabolite neoplastic agent. In some embodiments, a compound of Formulae (I), (Ta), (Ib), or (Ic), or a pharmaceutically acceptable salt thereof, may be administered in combination with a topoisomerase I inhibitor. In some embodiments, a compound of Formula (I), (Ia), (Ib), or (Ic), or a pharmaceutically acceptable salt thereof, may be administered in combination with a topoisomerase II inhibitor. In some embodiments, a compound of Formula (I), (Ia), (Ib), or (Ic), or a pharmaceutically acceptable salt thereof, may be administered in combination with an aromatase inhibitor. In some embodiments, a compound of Formula (I), (Ta), (Ib), or (Ic), or a pharmaceutically acceptable salt thereof, may be administered in combination with one or more anti-cancer agents.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be affected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, 3$^{rd}$ Ed., 1990 New York: Plenum Press; Mundy et al., Name Reaction and Reagents in Organic Synthesis, 2$^{nd}$ Ed., 2005 Hoboken, NJ: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, 3$^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain examples of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

The following abbreviations have the definitions set forth below:
1. DCM: Dichloromethane
2. DIPEA: N,N-Diisopropylethylamine
3. DMEM: Dulbecco's Modification of Eagle's Medium
4. DMSO: Dimethylsulfoxide
5. DMF: N,N-dimethylformamide
6. FBS: Fetal Bovine Serum
7. HATU Hexafluorophosphate Azabenzotriazole Tetramethyl Uronium
8. HPLC: High Pressure Liquid Chromatography
9. HRMS (ESI) High Resolution Mass Spectrometry (Electrospray Ionization)
10. LCMS Liquid Chromatography-Mass Spectrometry 11. MCF-7: Michigan Cancer Foundation-7 breast cancer cell line
12. NMR: Nuclear Magnetic Resonance
13. PBS; Phosphate-Buffered Saline
14. RPMI: Roswell Park Memorial Institute medium
15. TBST: Tris-Buffered Saline and Tween 20
16. TFA: Trifluoracetic Acid
17. SDS-PAGE Sodium Dodecyl Sulfate-Polyacrylamide Gel Electrophoresis Example 1: General Methods for Synthesizing CRBN Targeting PROTACs Compounds with structures as described and claimed herein, including in claim 1, can be prepared according to the following schemes. In general, the chimeric molecules can be approached in a step-wise or modular fashion. The three parts of modules, the target protein ligands, linkers, and the unique cereblon ligands can be assembled using known methods of chemical transformations to form amides, C—N bond and C—O bond. Representative modules of cereblon ligands are listed as the following:

CRBN-L1

CRBN-L2

CRBN-L3

CRBN-L4

CRBN-L5

CRBN-L6

CRBN-L7
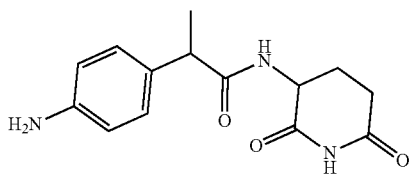

CRBN-L8
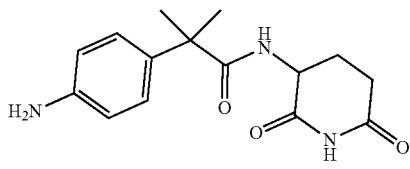

CRBN-L9
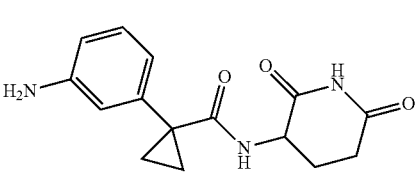

CRBN-L10
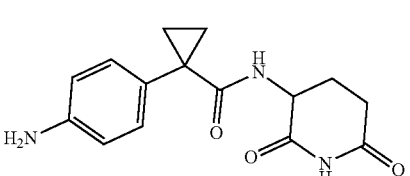

CRBN-L11
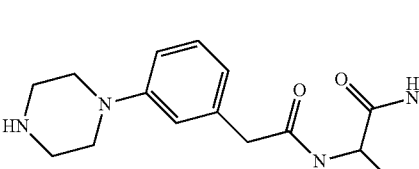

CRBN-L12
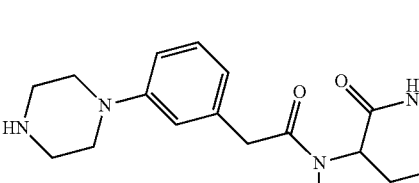

CRBN-L13
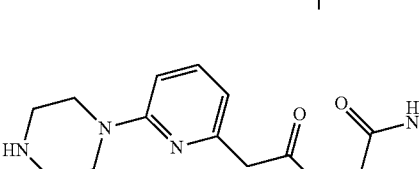

CRBN-L14
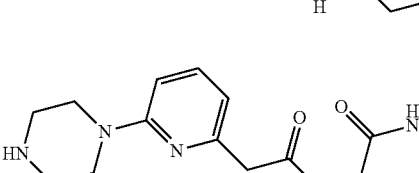

CRBN-L15

CRBN-L16

CRBN-L17

CRBN-L18

CRBN-L19

CRBN-L20

CRBN-L21

CRBN-L22

CRBN-L23

CRBN-24

CRBN-L25

CRBN-L26

CRBN-L27

CRBN-L28

CRBN-L29

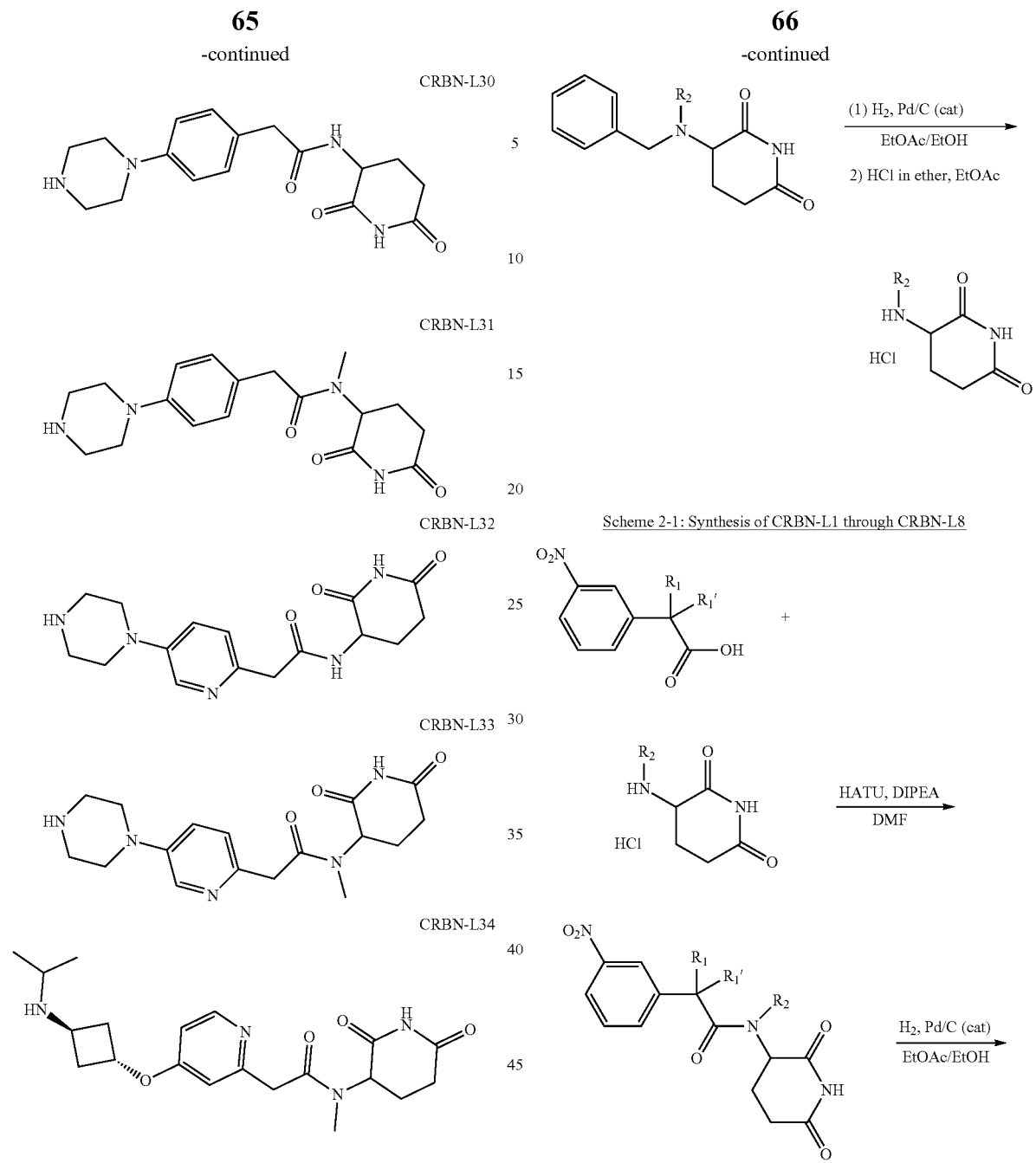
The following schemes represent general methods showing how the unique cereblon ligands CRBN-L1 through CRBN-L34 in this application can be made. There can be other methods to synthesize these ligands for those skilled in the art of chemical synthesis.
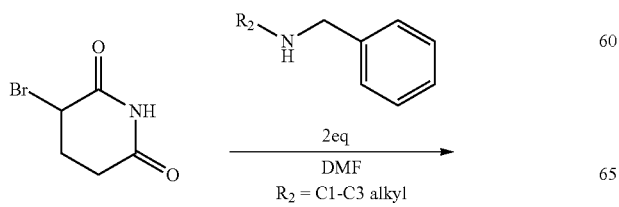

67
-continued
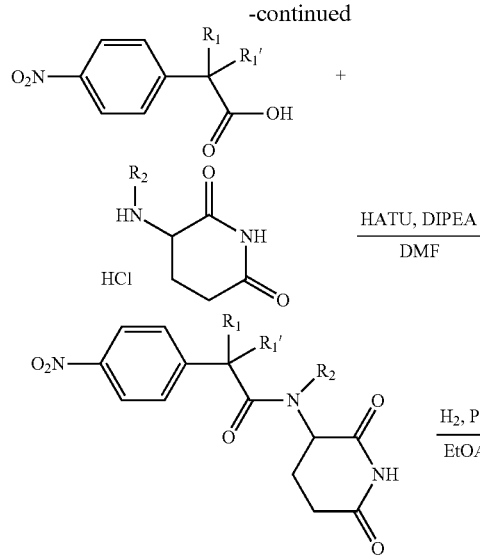
68
-continued
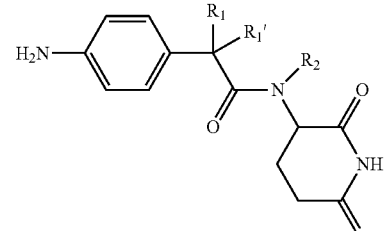
CRBN-L5: R1 = R1' = R2 = H
CRBN-L6: R1 = R1' = H, R2 = Me
CRBN-L7: R1 = Me, R1' = R2 = H
CRBN-L8: R1 = R1' = Me, R2 = H
Scheme 2-2: Synthesis of CRBN-L9 and CRBN-L10
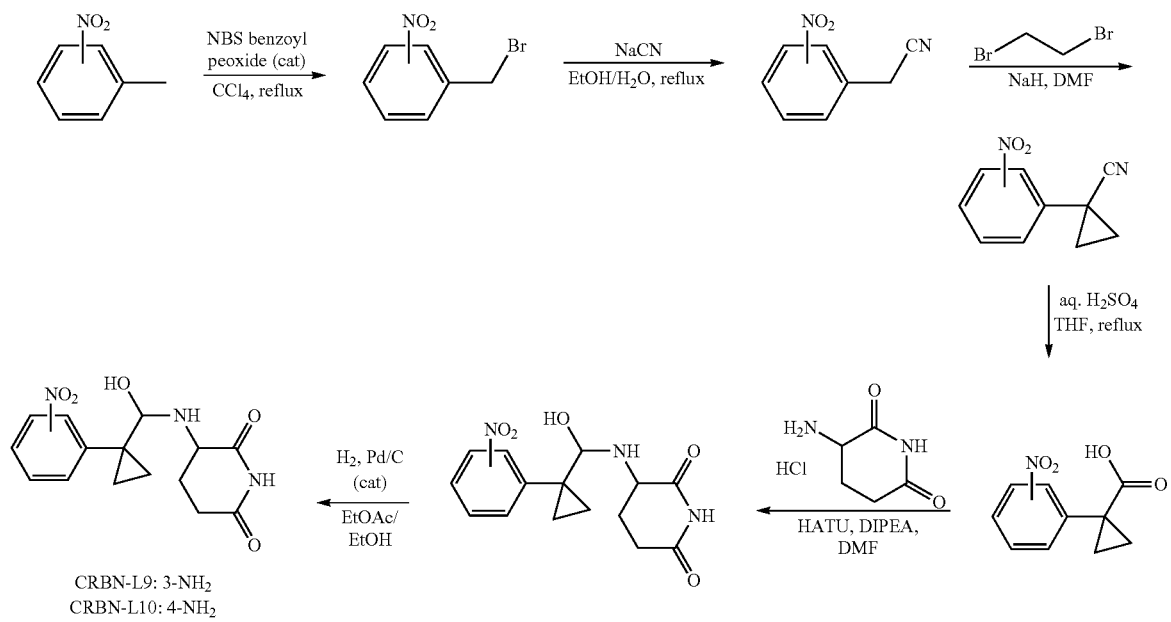
CRBN-L9: 3-$NH_2$
CRBN-L10: 4-$NH_2$
Scheme 2-3: Synthesis of CRBN-L11 through CRBN-L14
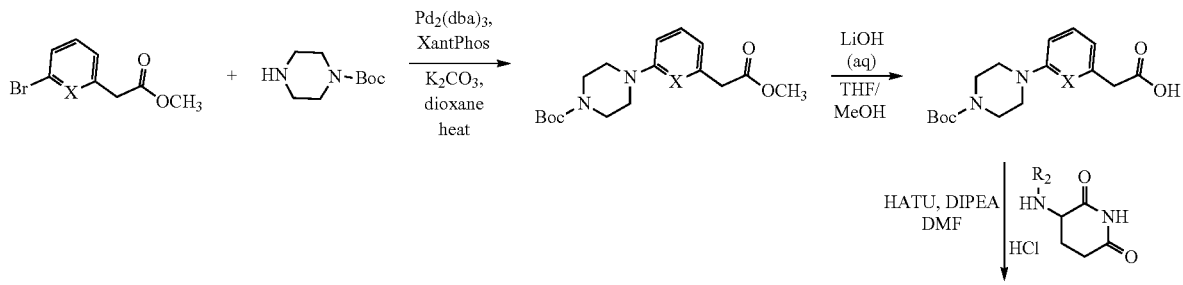

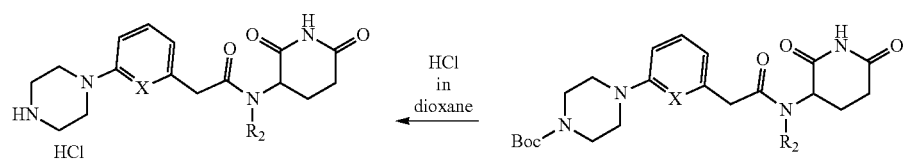
CRBN-L11: X = CH, R2 = H
CRBN-L12: X = CH, R2 = Me
CRBN-L13: X = N, R2 = H
CRBN-L14: X = N, R2 = Me
Scheme 2-4: Synthesis of CRBN-L15 through CRBN-L20
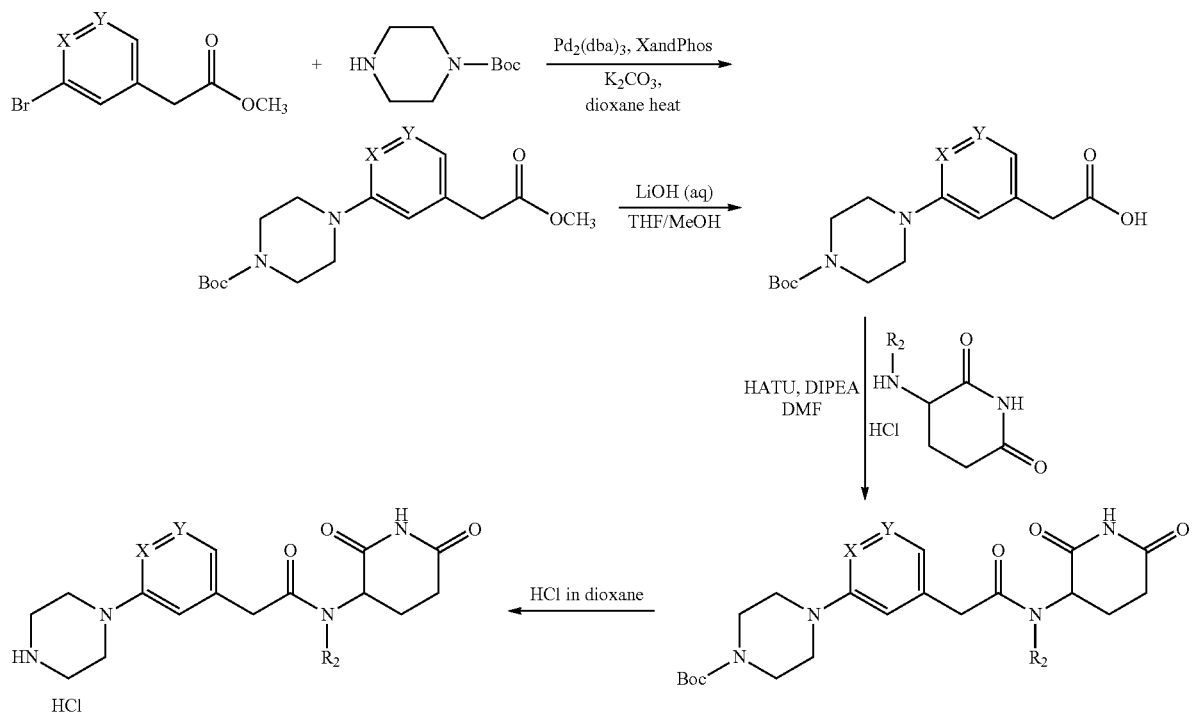
CRBN-L15: X = N, Y = CH, R2 = H
CRBN-L16: X = N, Y = CH, R2 = Me
CRBN-L17: X = CH, Y = N, R2 = H
CRBN-L18: X = CH, Y = N, R2 = Me
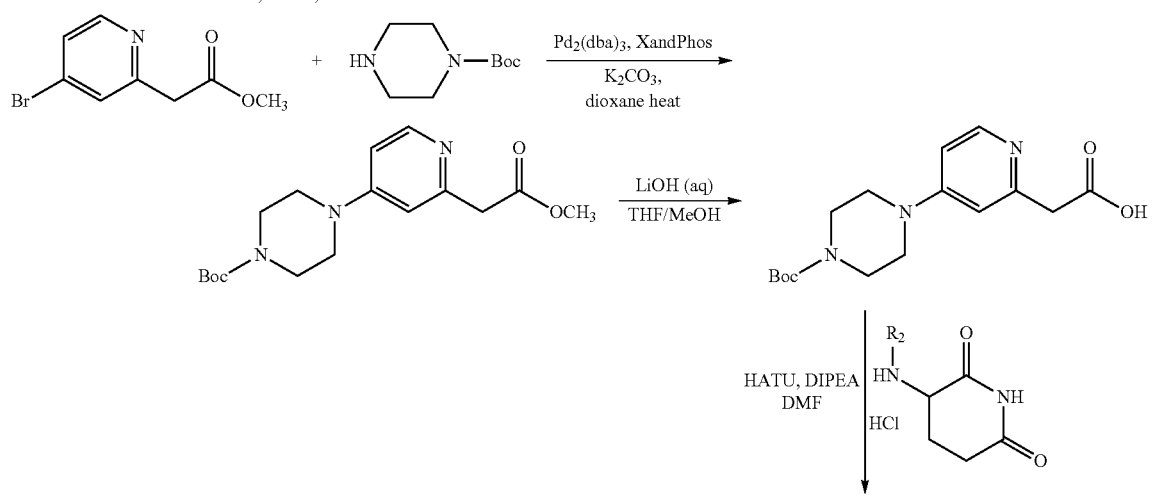

-continued
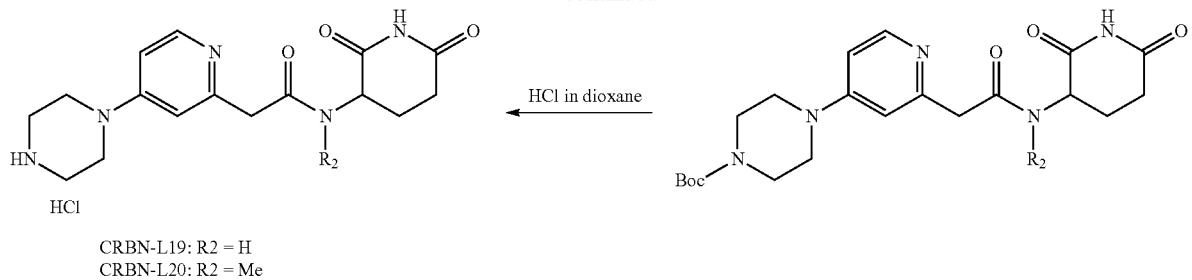
CRBN-L19: R2 = H
CRBN-L20: R2 = Me
Scheme 2-5: Synthesis of CRBN-L21 through CRBN-L25
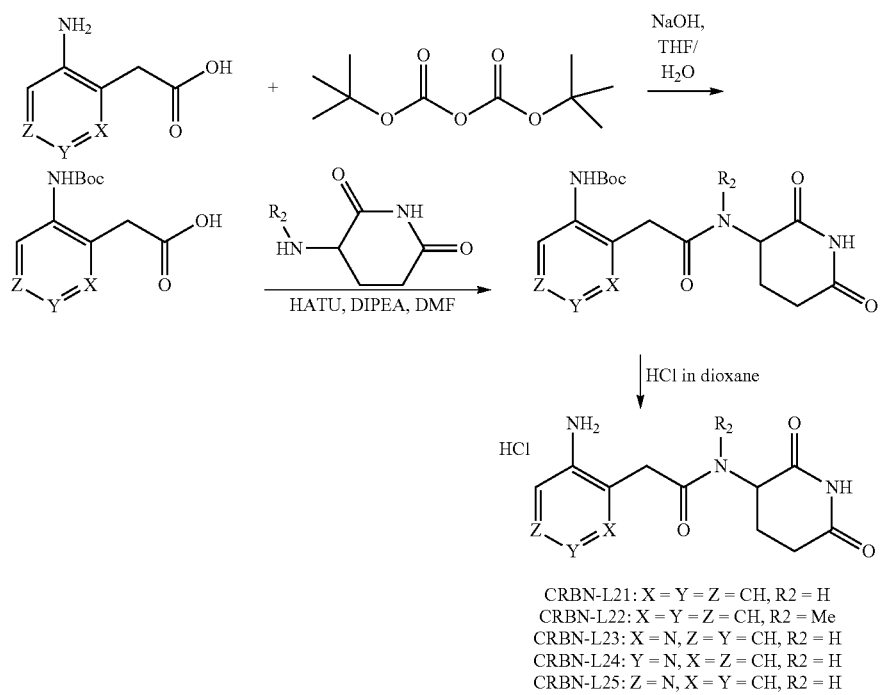
CRBN-L21: X = Y = Z = CH, R2 = H
CRBN-L22: X = Y = Z = CH, R2 = Me
CRBN-L23: X = N, Z = Y = CH, R2 = H
CRBN-L24: Y = N, X = Z = CH, R2 = H
CRBN-L25: Z = N, X = Y = CH, R2 = H
Scheme 2-6: Synthesis of CRBN-L26 through CRBN-L29
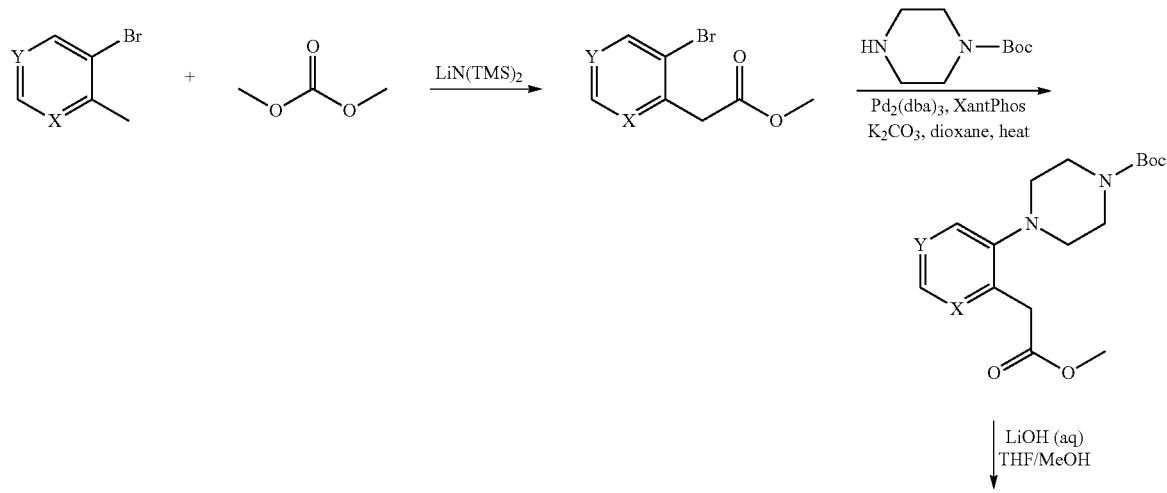

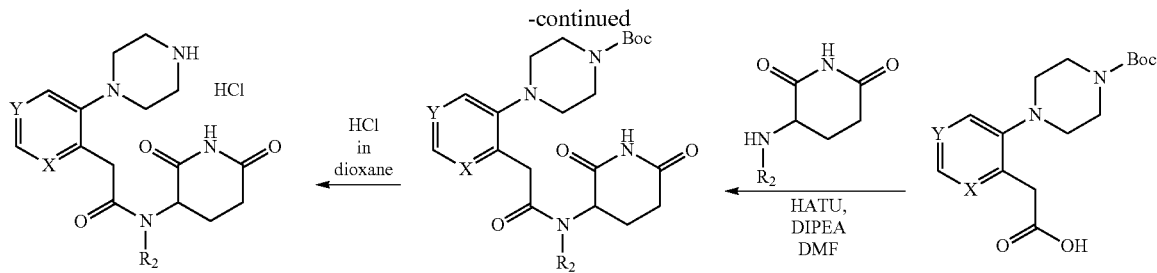
CRBN-L26: X = Y = CH, R2 = H
CRBN-L27: X = N, Y = CH, R2 = Me
CRBN-L28: Y = N, X = CH, R2 = H
CRBN-L29: Y = N, X = CH, R2 = Me
Scheme 2-7: Synthesis of CRBN-L30 through CRBN-L33
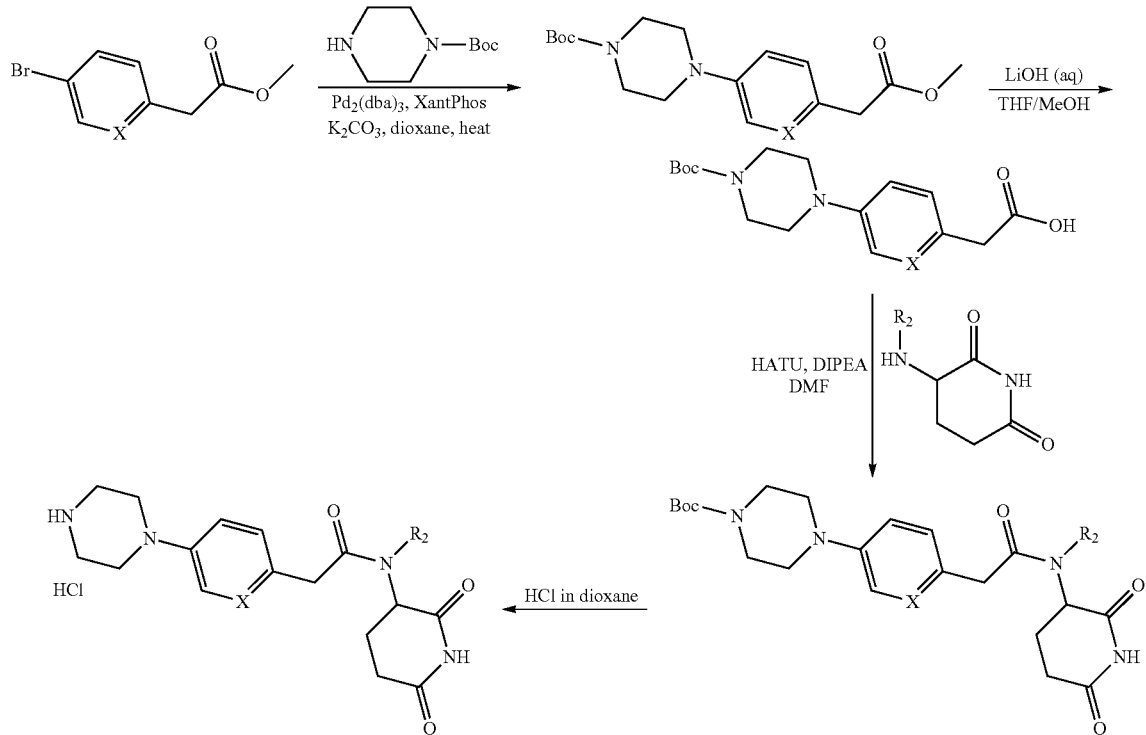
CRBN-L30: X = CH, R2 = H
CRBN-L31: X = CH, R2 = Me
CRBN-L32: X = N, R2 = H
CRBN-L33: X = N, R2 = Me
Example 2: Procedure for Synthesis of CRBN-L5
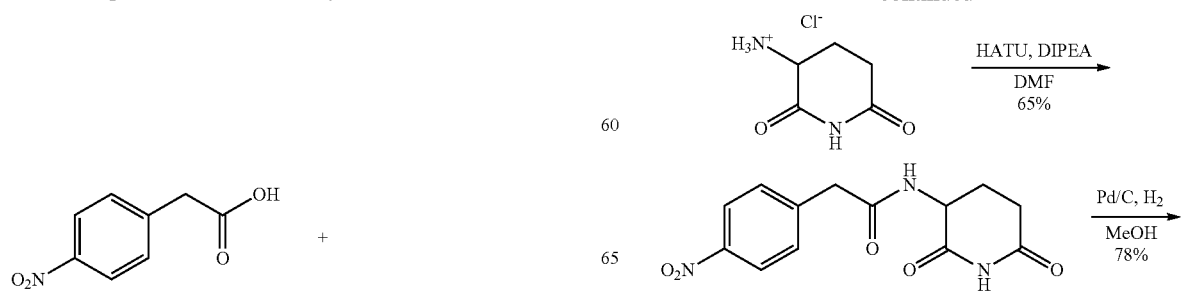

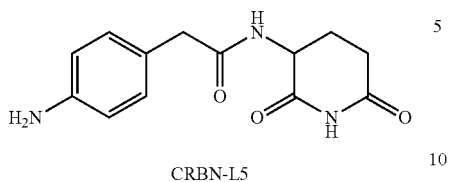

CRBN-L5

Step 1: Synthesis of N-(2,6-dioxopiperidin-3-yl)-2-(4-nitrophenyl)acetamide 2-(4-nitrophenyl)acetic acid (1.0 g, 5.52 mmol), 2,6-dioxopiperidin-3-aminium chloride (909 mg, 5.52 mmol) and HATU (252 mg, 6.62 mmol) were dissolved in DMF (5 mL), followed by addition of DIPEA (213 mg, 16.6 mmol). The mixture was stirred at room temperature for 4 hours. LCMS showed that the reaction was completed. The mixture was quenched by water (25 mL) at 20-30° C. The solid was precipitated and filtered. It was dried to get the orange solid (1.05 g, 65% yield). HRMS (ESI) m/z:[M+H]$^+$ calcd for $C_{13}H_{14}N_3O_5^+$, 292.0928. found: 292.0937.

Step 2: Synthesis of 2-(4-aminophenyl)-N-(2,6-dioxopiperidin-3-yl)acetamide (CRBN-L5)

A mixture of the above solid (100.0 mg, 343 umol) and Palladium/C catalyst (10.0 mg) in methanol (5 mL) was stirred in at hydrogen atmosphere. LCMS showed that the reaction was completed. The mixture was filtered and concentrated to get the crude product as a yellow solid (70.0 mg, 78% yield). HRMS (ESI) m/z:[M+H]$^+$ calcd for $C_{13}H_{16}N_3O_3^+$, 262.1128. found: 262.1190. $^1$H NMR (500 MHz, DMSO-$d_6$) δ 10.79 (s, 1H), 8.21 (d, J=8.2 Hz, 1H), 6.96-6.82 (m, 2H), 6.56-6.38 (m, 2H), 4.89 (s, 2H), 4.52 (ddd, J=10.7, 8.8, 7.4 Hz, 1H), 3.27 (s, 2H), 2.78-2.65 (m, 1H), 2.45 (t, J=3.8 Hz, OH), 2.00-1.82 (m, 2H).

Example 3: Procedure for Synthesis of CRBN-L1

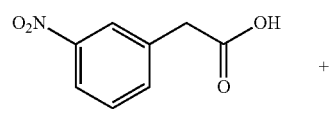

+

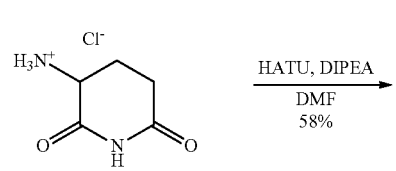

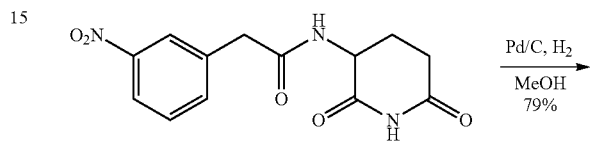

CRBN-L1

Step 1, Synthesis of N-(2,6-dioxopiperidin-3-yl)-2-(3-nitrophenyl)acetamide 2-(3-nitrophenyl)acetic acid (1.0 g, 5.52 mmol), 2,6-dioxopiperidin-3-aminium chloride (909 mg, 5.52 mmol) and HATU (252 mg, 6.62 mmol) were dissolved in DMF (5 mL), followed by addition of DIPEA (213 mg, 16.6 mmol). The mixture was stirred at room temperature for 4 hours. LCMS showed that the reaction was completed. The mixture was quenched by water (25 mL) at 20-30° C. The solid was precipitated and filtered. It was dried to get the pale solid (0.94 g, 58% yield). HRMS (ESI) m/z:[M+H]$^+$ calcd for $C_{13}H_{14}N_3O_5^+$, 292.0928. found: 292.1134.

Step 2, Synthesis of 2-(3-aminophenyl)-N-(2,6-dioxopiperidin-3-yl)acetamide (CRBN-L1)

A mixture of the above solid (100.0 mg, 343 umol) and Palladium/C catalyst (10.0 mg) in methanol (5 mL) was stirred in at hydrogen atmosphere. LCMS showed that the reaction was completed. The mixture was filtered and concentrated to get the crude product as a light green solid (71.0 mg, 79% yield). HRMS (ESI) m/z:[M+H]$^+$ calcd for $C_{13}H_{16}N_3O_3^+$, 262.1128. found: 262.1328. $^1$H NMR (500 MHz, DMSO-$d_6$) δ 10.80 (s, 1H), 8.30 (d, J=8.2 Hz, 1H), 6.91 (t, J=7.7 Hz, 1H), 6.46 (t, J=2.0 Hz, 1H), 6.44-6.38 (m, 2H), 4.98 (s, 2H), 4.53 (q, J=8.3 Hz, 1H), 3.30 (s, 2H), 2.81-2.62 (m, 1H), 2.46 (t, J=3.8 Hz, 1H), 1.91 (tt, J=7.2, 4.0 Hz, 2H).

Example 4: Procedure for Synthesis of Compound 222174
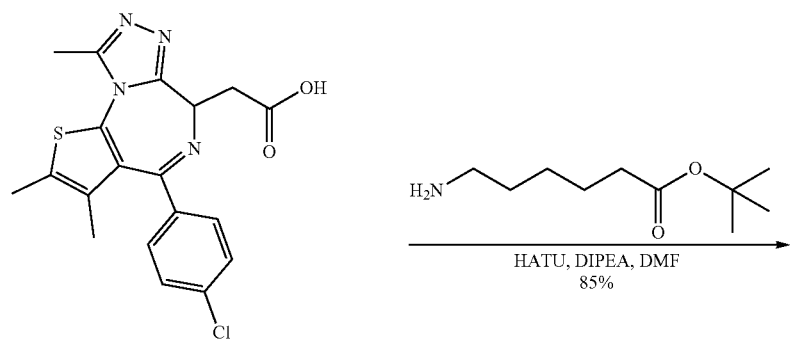
JQ-1
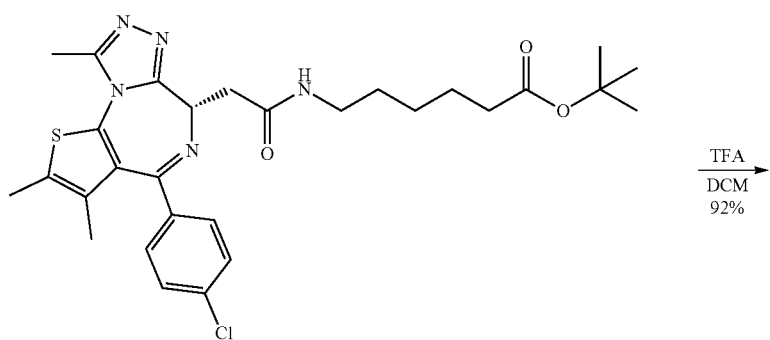
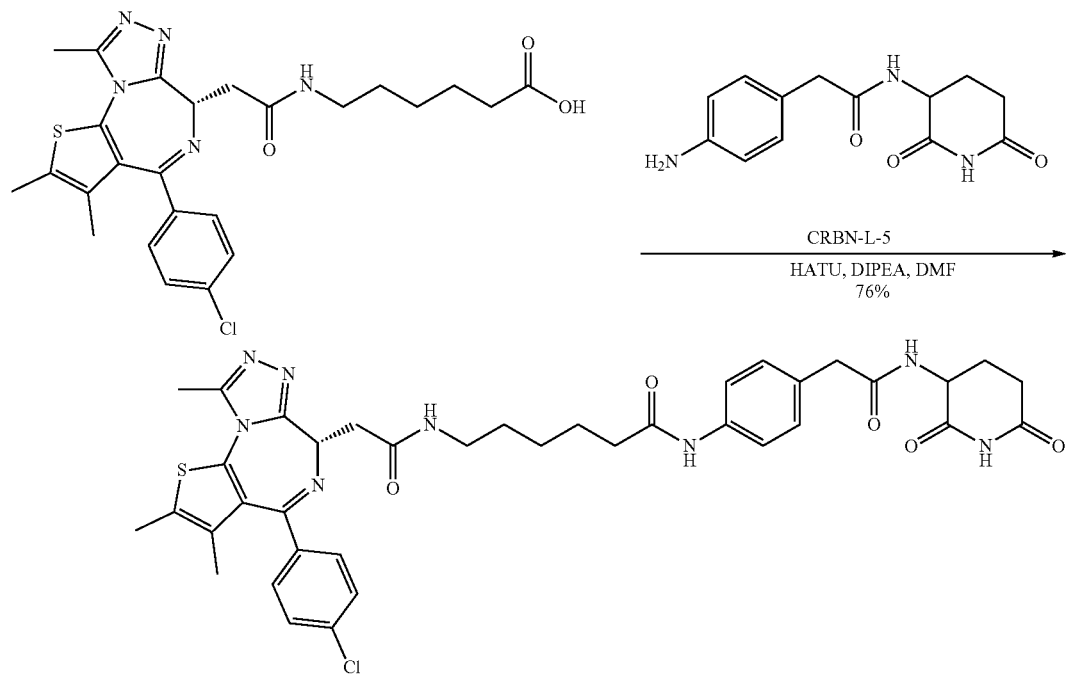
Compound 222174

Step 1, Synthesis of (S)-tert-butyl-6-(2-(4-(4-chlorophenyl)-2,3,9-trimethyl-6H-thieno[3,2-f][1,2,4]triazolo[4,3-a][1,4]diazepin-6-yl)acetamido)hexanoate (S)-2-(4-(4-chlorophenyl)-2,3,9-trimethyl-6H-thieno[3,2-f][1,2,4]triazolo[4,3-a][1,4]diazepin-6-yl)acetic acid (JQ-1, 30.0 mg, 74.8 umol), tert-butyl 6-aminohexanoate (14.0 mg, 74.8 umol) and HATU (34.1 mg, 90.0 umol) were dissolved in DMF (2 mL), followed by addition of DIPEA (29.0 mg, 225 umol). The mixture was stirred at room temperature for 4 hours. LCMS showed that the reaction was completed. The crude product was then purified by prep-HPLC to afford the desired product (36.3 mg, 85% yield) as a yellow solid. HRMS (ESI) r/z:[M+H]$^+$ calcd for $C_{29}H_{37}ClN_5O_3S^+$, 570.2300. found: 570.2280.

Step 2, Synthesis of(S)-6-(2-(4-(4-chlorophenyl)-2,3,9-trimethyl-6H-thieno[3,2-f]-[1,2,4]triazolo[4,3-a][1,4]diazepin-6-yl)acetamido)hexanoic acid The above solid (25.0 mg, 43.8 umol) was dissolved with DCM (2 mL), followed by addition of TFA (1.0 mL) drop-wise. The mixture was stirred at room temperature for 1 hour. LCMS showed that the reaction was completed. The reaction mixture was evaporated on vacuum to remove the solvent and the residue was then purified by prep-HPLC to afford the desired product (20.7 mg, 92% yield) as a yellow solid. HRMS (ESI) m/z:[M+H]$^+$ calcd for $C_{25}H_{29}ClN_5O_3S^+$, 514.1674. found: 514.1667.

Step 3, Synthesis of 6-(2-((S)-4-(4-chlorophenyl)-2,3,9-trimethyl-6H-thieno-[3,2-f][1,2,4]triazolo[4,3-a][1,4]diazepin-6-yl)acetamido)-N-(4-(2-((2,6-dioxopiperidin-3-yl)amino)-2-oxoethyl)phenyl)hexanamide (Compound 222174)

The above solid (10.0 mg, 19.5 umol), 2-(4-aminophenyl)-N-(2,6-dioxopiperidin-3-yl)-acetamide (5.1 mg, 19.5 umol) and HATU (9.0 mg, 23.4 umol) were dissolved in DMF (2 mL), followed by addition of DIPEA (7.8 mg, 60.4 umol). The mixture was stirred at room temperature for 4 hours. LCMS showed that the reaction was completed. The crude product was then purified by prep-HPLC to afford the desired product (11.1 mg, 75% yield) as a yellow foam. $^1$H NMR (500 MHz, DMSO-$d_6$) δ 10.80 (s, 1H), 9.94 (d, J=9.9 Hz, 1H), 8.44 (d, J=8.2 Hz, 1H), 8.23 (t, J=5.6 Hz, 1H), 7.51 (m, 5H), 7.45-7.39 (m, 2H), 7.17 (dd, J=11.5, 8.4 Hz, 2H), 4.51 (dd, J=8.2, 6.0 Hz, 2H), 3.44-3.43 (d, J=2.3 Hz, 2H), 3.29-3.14 (m, 4H), 2.73 (s, 1H), 2.60 (s, 3H), 2.41 (s, 3H), 2.30 (m, 2H), 1.91 (s, 2H), 1.62 (s, 3H), 1.48-1.44 (m, 2H), 1.24 (s, 2H), 1.21-1.13 (m, 2H). HRMS (ESI) m/z:[M+H]$^+$ calcd for $C_{38}H_{42}C_1N_8O_5S^+$, 757.2682. found: 757.2609.

Example 5: Procedure for Synthesis of Compound 222175

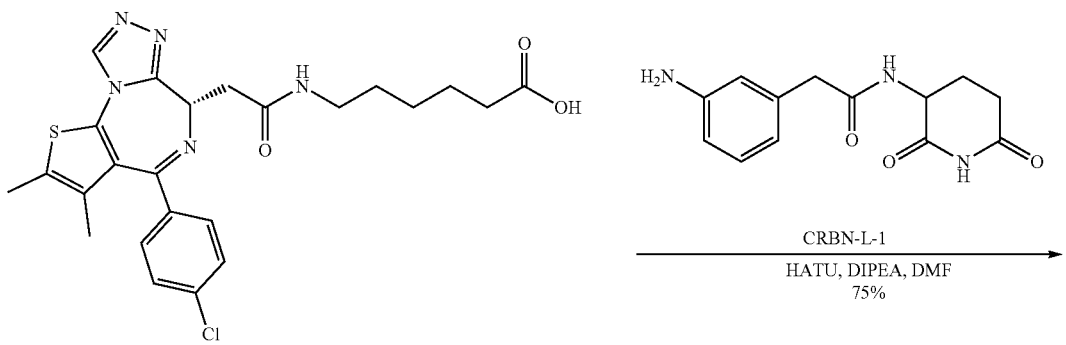

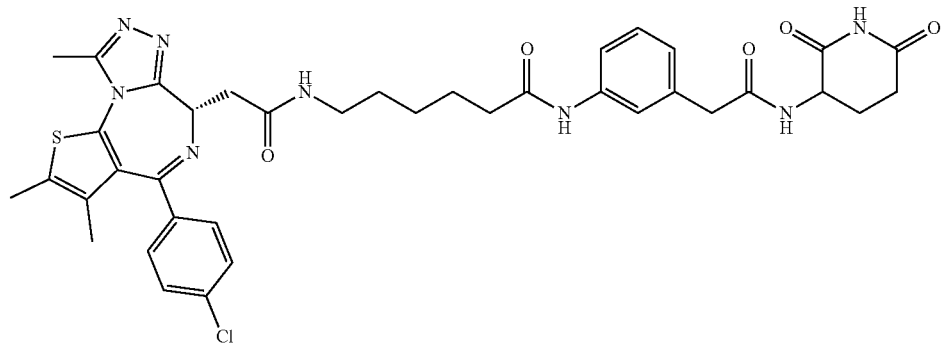

Compound 222175

Synthesis of 6-(2-((S)-4-(4-chlorophenyl)-2,3,9-trimethyl-6H-thieno[3,2-f][1,2,4]-triazolo[4,3-a][1,4]diazepin-6-yl)acetamido)-N-(3-(2-((2,6-dioxopiperidin-3-yl)amino)-2-oxoethyl)phenyl)hexanamide
(Compound 222175)

(S)-6-(2-(4-(4-chlorophenyl)-2,3,9-trimethyl-6H-thieno[3,2-f]-[1,2,4]triazolo[4,3-a][1,4]diazepin-6-yl)acetamido)hexanoic acid (10.0 mg, 19.5 umol), 2-(3-aminophenyl)-N-(2,6-dioxopiperidin-3-yl)-acetamide (5.1 mg, 19.5 umol) and HATU (9.0 mg, 23.4 umol) were dissolved in DMF (2 mL), followed by addition of DIPEA (7.8 mg, 60.4 umol). The mixture was stirred at room temperature for 4 hours. LCMS showed that the reaction was completed. The crude product was then purified by prep-HPLC to afford the desired product (11.1 mg, 75% yield) as a yellow solid. $^1$H NMR (500 MHz, DMSO-$d_6$) δ 10.80 (s, 1H), 9.88 (s, 1H), 9.14 (s, 1 H), 8.49-8.39 (m, 1H), 8.20 (t, J=5.8 Hz, 1H), 7.53-7.36 (m, 6H), 7.19 (td, J=7.8, 2.3 Hz, 1H), 6.95 (d, J=7.6 Hz, 1H), 4.61-4.47 (m, 2H), 3.44 (d, J=2.3 Hz, 2H), 3.15-3.07 (m, 4H), 2.70 (dd, J=17.9, 9.1 Hz, 1H), 2.60 (s, 3H), 2.41 (s, 3H), 2.32-2.27 (m, 2H), 1.91 (td, J=8.5, 4.6 Hz, 2H), 1.62 (s, 3H), 1.46 (q, J=7.4 Hz, 2H), 1.33 (t, J=8.0 Hz, 2H), 1.28 (m, 2H). HRMS (ESI) m/z:[M+H]$^+$ calcd for $C_{38}H_{42}ClN_8O_5S$, 757.2682. found: 757.2687.

Example 6: Procedure for Synthesis of Compound 253034

Step 1, Synthesis of tert-butyl (11-((4-(2-((2,6-dioxopiperidin-3-yl)amino)-2-oxoethyl)phenyl)amino)-11-oxoundecyl)carbamate 2-(4-aminophenyl)-N-(2,6-dioxopiperidin-3-yl)acetamide (20.0 mg, 76.5 umol), 11-((tert-butoxycarbonyl)amino)undecanoic acid (23.1 mg, 76.5 umol) and HATU (29.1 mg, 91.8 umol) were dissolved in DMF(2 mL), followed by addition of DIPEA (29.7 mg, 230 umol). The mixture was stirred at room temperature for 4 hours. LCMS showed that the reaction was completed. The crude product was then purified by prep-HPLC to afford the desired product (32.5 mg, 78% yield) as a yellow solid. HRMS (ESI) m/z:[M+H]$^+$ calcd for $C_{29}H_{45}N_4O_6^+$, 545.3334. found: 545.3329.

Step 2, Synthesis of 11-amino-N-(4-(2-((2,6-dioxopiperidin-3-yl)amino)-2-oxoethyl)-phenyl)undecanamide Tert-butyl (11-((4-(2-((2,6-dioxopiperidin-3-yl)amino)-2-oxoethyl)phenyl)amino)-11-oxoundecyl)carbamate (15.0 mg, 27.5 umol) was dissolved in DCM (2 mL), followed by addition of TFA (1.0 mL) drop-wise. The mixture was stirred at room temperature for 1 hour. LCMS showed that the reaction was completed. The reaction mixture was evaporated on vacuum to remove the solvent and the residue was then purified by prep-HPLC to afford the desired product

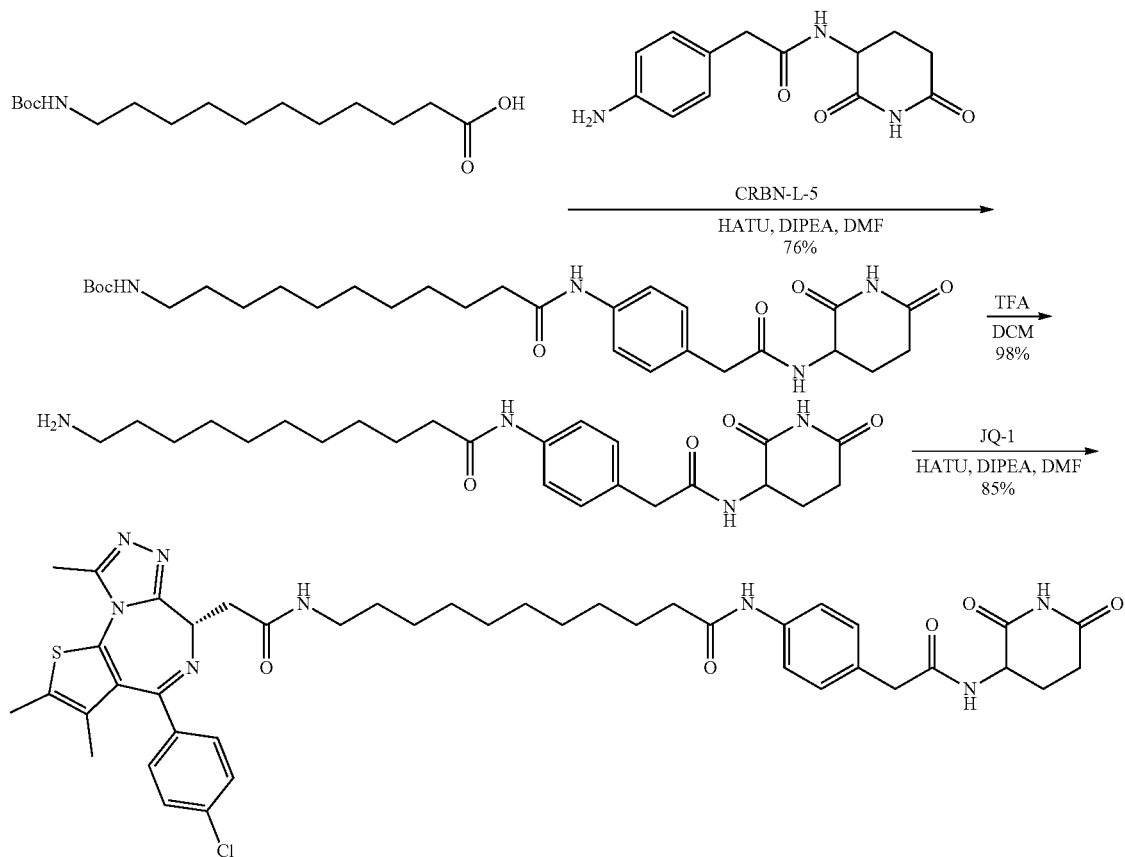

Compound 253034

(11.7 mg, 96% yield). HRMS (ESI) m/z:[M+H]+ calcd for $C_{24}H_{37}N_4O_4^+$, 445.2809. found: 445.2730.

Step 3, Synthesis of 11-(2-((S)-4-(4-chlorophenyl)-2,3,9-trimethyl-6H-thieno[3,2-f]-[1,2,4]triazolo[4,3-a][1,4]diazepin-6-yl)acetamido)-N-(4-(2-((2,6-dioxopiperidin-3-yl)amino)-2-oxoethyl)phenyl)undecanamide (Compound 253034) [0150](S)-2-(4-(4-chlorophenyl)-2,3,9-trimethyl-6H-thieno[3,2-f][1,2,4]triazolo[4,3-a][1,4]diazepin-6-yl) acetic acid (JQ-1, 11.0 mg, 27.5 umol), I 1-amino-N-(4-(2-((2,6-dioxopiperidin-3-yl)amino)-2-oxoethyl)-phenyl) undecanamide (12.2 mg, 27.5 umol) and HATU (15.7 mg, 41.3 umol) were dissolved in DMF (2 mL), followed by addition of DIPEA (10.7 mg, 82.6 umol). The mixture was stirred at room temperature for 4 hours. LCMS showed that the reaction was completed. The reaction mixture was then purified by prep-HPLC to afford the desired product (19.3 mg, 85% yield) as a yellow solid. $^1$H NMR (500 MHz, DMSO-d$_6$) δ 10.81 (s, 1H), 9.85 (s, 1H), 8.40 (d, J=8.2 Hz, 1H), 8.19 (t, J=5.7 Hz, 1H), 7.50 (dd, J=8.6, 6.7 Hz, 4H), 7.43 (d, J=8.6 Hz, 2H), 7.26-7.12 (m, 2H), 4.54 (ddd, J=10.2, 6.0, 4.0 Hz, 2H), 3.42 (s, 2H), 3.31-3.02 (m, 4H), 2.79-2.67 (m, 1H), 2.63 (s, 3H), 2.42 (s, 3H), 2.27 (t, J=7.4 Hz, 2H), 1.91 (ddt, J=10.9, 8.0, 4.1 Hz, 2H), 1.63 (s, 3H), 1.55 (q, J=7.1 Hz, 2H), 1.42 (q, J=6.9 Hz, 2H), 1.26 (q, J=8.5, 7.2 Hz, 12H). HRMS (ESI) m/z:[M+H]+ calcd for $C_{43}H_{52}ClN_8O_5S^+$, 827.3464. found: 827.3469.

Example 7: Procedure for Synthesis of Compound 253035

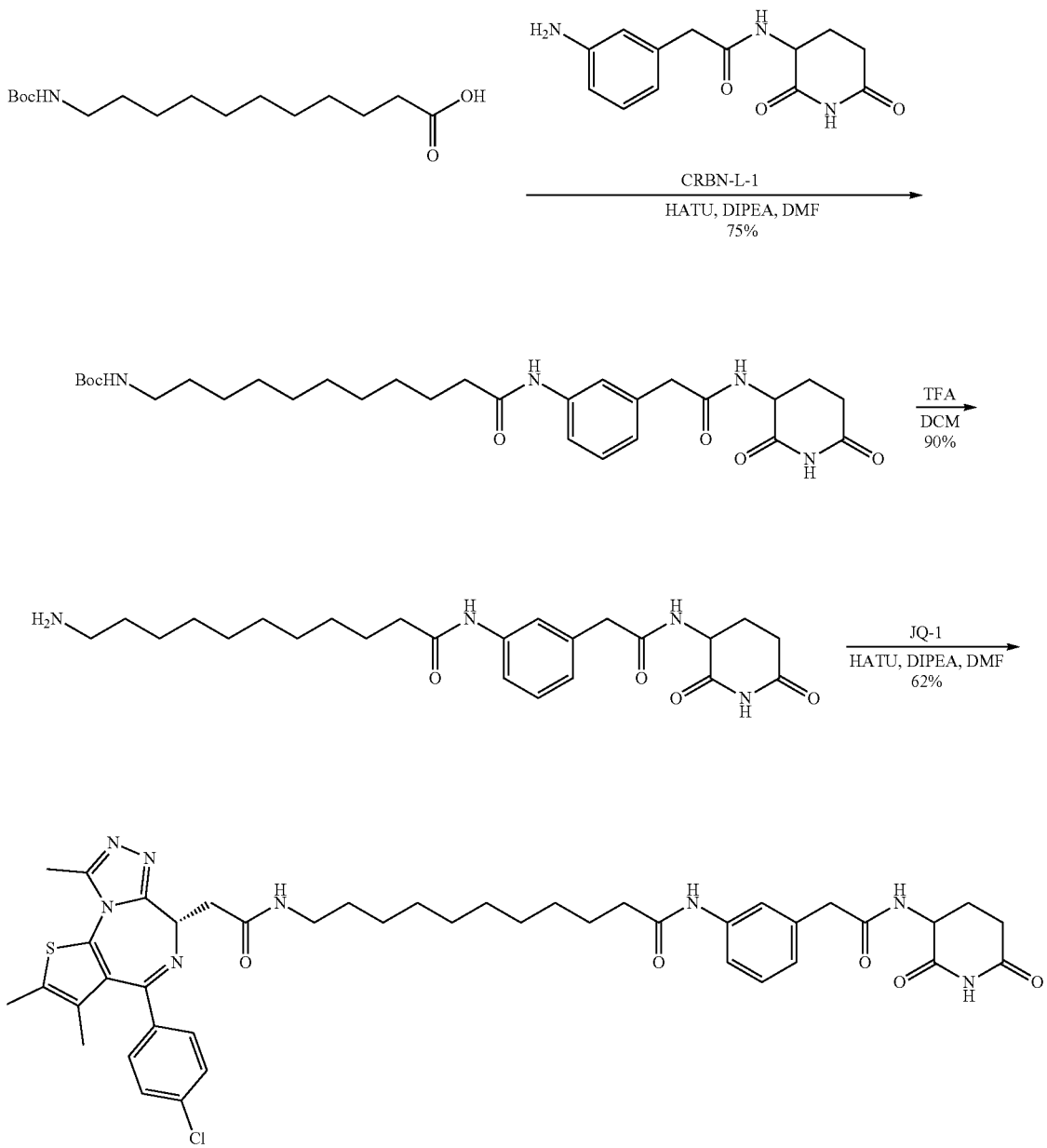

Compound 253035

Step 1, Synthesis of tert-butyl (11-((3-(2-((2,6-dioxopiperidin-3-yl)amino)-2-oxoethyl)phenyl)amino)-II-oxoundecyl)carbamate 2-(3-aminophenyl)-N-(2,6-dioxopiperidin-3-yl)acetamide (20.0 mg, 76.5 umol), 11-((tert-butoxycarbonyl)amino)undecanoic acid (23.1 mg, 76.5 umol) and HATU (29.1 mg, 91.8 umol) were dissolved in DMF (2 mL), followed by addition of DIPEA (29.7 mg, 230 umol). The mixture was stirred at room temperature for 4 hours. LCMS showed that the reaction was completed. The reaction mixture was then purified by prep-HPLC to afford the desired product (31.3 mg, 75% yield) as a yellow solid. HRMS (ESI) m/z:[M+H]$^+$ calcd for $C_{29}H_{45}N_4O_6^+$, 545.3334. found: 545.3342.

Step 2, Synthesis of 11-amino-N-(3-(2-((2,6-dioxopiperidin-3-yl)amino)-2-oxoethyl)-phenyl)undecanamide Tert-butyl (11-((3-(2-((2,6-dioxopiperidin-3-yl)amino)-2-oxoethyl)phenyl)amino)-11-oxoundecyl)carbamate (15.0 mg, 27.5 umol) was dissolved with DCM (2 mL) followed by addition of TFA (1.0 mL) drop-wise. The mixture was stirred at room temperature for 1 hour. LCMS showed that the reaction was completed. The reaction mixture was evaporated on vacuum to remove the solvent and the residue was then purified by prep-HPLC to afford the desired product (11.0 mg, 90% yield) as a yellow solid. HRMS (ESI) m/z:[M+H]$^+$ calcd for $C_{24}H_{37}N_4O_4^+$, 445.2809. found: 445.2736.

Step 3, Synthesis of 11-(2-((S)-4-(4-chlorophenyl)-3,9-dimethyl-6H-thieno[3,2-f]-[1,2,4]triazolo[4,3-a][1,4]diazepin-6-yl)acetamido)-N-(3-(2-((2,6-dioxopiperidin-3-yl)amino)-2-oxoethyl)phenyl) undecanamide (Compound 253035)

(S)-2-(4-(4-chlorophenyl)-2,3,9-trimethyl-6H-thieno[3,2-f][1,2,4]triazolo[4,3-a][1,4]diazepin-6-yl)acetic acid (JQ-1, 11.0 mg, 27.5 umol), 1l-amino-N-(3-(2-((2,6-dioxopiperidin-3-yl)amino)-2-oxoethyl)-phenyl)undecanamide (12.2 mg, 27.5 umol) and HATU (15.7 mg, 41.3 umol) were dissolved in DMF (2 mL), followed by addition of DIPEA (10.7 mg, 82.6 umol). The mixture was stirred at room temperature for 4 hours. LCMS showed that the reaction was completed. The reaction mixture was then purified by prep-HPLC to afford the desired product (18.7 mg, 82% yield) as a yellow solid. $^1$H NMR (500 MHz, DMSO-d$_6$) δ 10.81 (s, 1H), 9.87 (s, 1H), 8.45 (d, J=8.2 Hz, 1H), 8.20 (t, J=5.6 Hz, 1H), 7.55-7.39 (m, 6H), 7.19 (t, J=7.8 Hz, 1H), 7.00-6.88 (m, 1H), 4.63-4.46 (m, 2H), 3.45 (s, 2H), 3.33-3.00 (m, 4H), 2.71 (ddd, J=18.1, 10.4, 8.5 Hz, 1H), 2.64 (s, 3H), 2.42 (s, 3H), 2.28 (t, J=7.4 Hz, 2H), 1.92 (tt, J=10.2, 4.3 Hz, 2H), 1.63 (s, 3H), 1.56 (q, J=7.0 Hz, 2H), 1.43 (p, J=7.0 Hz, 2H), 1.27 (dt, J=11.2, 5.7 Hz, 12H). HRMS (ESI) m/z:[M+H]$^+$ calcd for $C_{43}H_{52}ClN_8O_5S^+$, 827.3464. found: 827.3462.

Example 8: PROTACS Containing JQ1 have Degradative Activity Against Proteins Containing BET Domains In Vitro MCF7 cells were plated in 24-well plates at 1.5×10$^5$ cells/well in DMEM growth medium containing 10% FBS and 1% Penicillin Streptomycin, and incubated overnight at 37° C. The following day, test compound was administered to the cells using 1000× compound stock solution prepared in DMSO at various concentrations. After administration of the compound, the cells were incubated at 37° C. for 6 hours. Cells were then washed with PBS and protein was collected in Laemmli sample buffer (1×; VWR International). Protein was isolated from cell lysate (approximately 25 μg) by SDS-PAGE and transferred to nitrocellulose membranes. Non-specific binding was blocked by incubating with blocking buffer (5% milk in Tris-buffered saline with 0.1% Tween 20 ("TBS-T")) at room temperature for 60 minutes. The membrane was then incubated with primary antibodies (rabbit anti-BRD2 (1:1000, Cell Signaling), mouse anti-GAPDH (1:5,000, Santa Cruz), mouse anti-BRD3 (1:500, Abcam) and rabbit anti-BRD4 (1:500, Abcam)) overnight at 4° C., followed by washing (3 times) with TBS-T, and incubation with horseradish peroxidase-conjugated rabbit anti-mouse IgG (1:5,000, Jackson Immunoresearch) or goat anti-mouse IgG (1:5,000, Jackson Immunoresearch) for 60 minutes. After washing with TBS-T, blots were developed using an enhanced chemiluminescence kit (ThermoFisher Scientific) and the bands were imaged and quantified by densitometry (Bio-Rad).

Figure 1B:
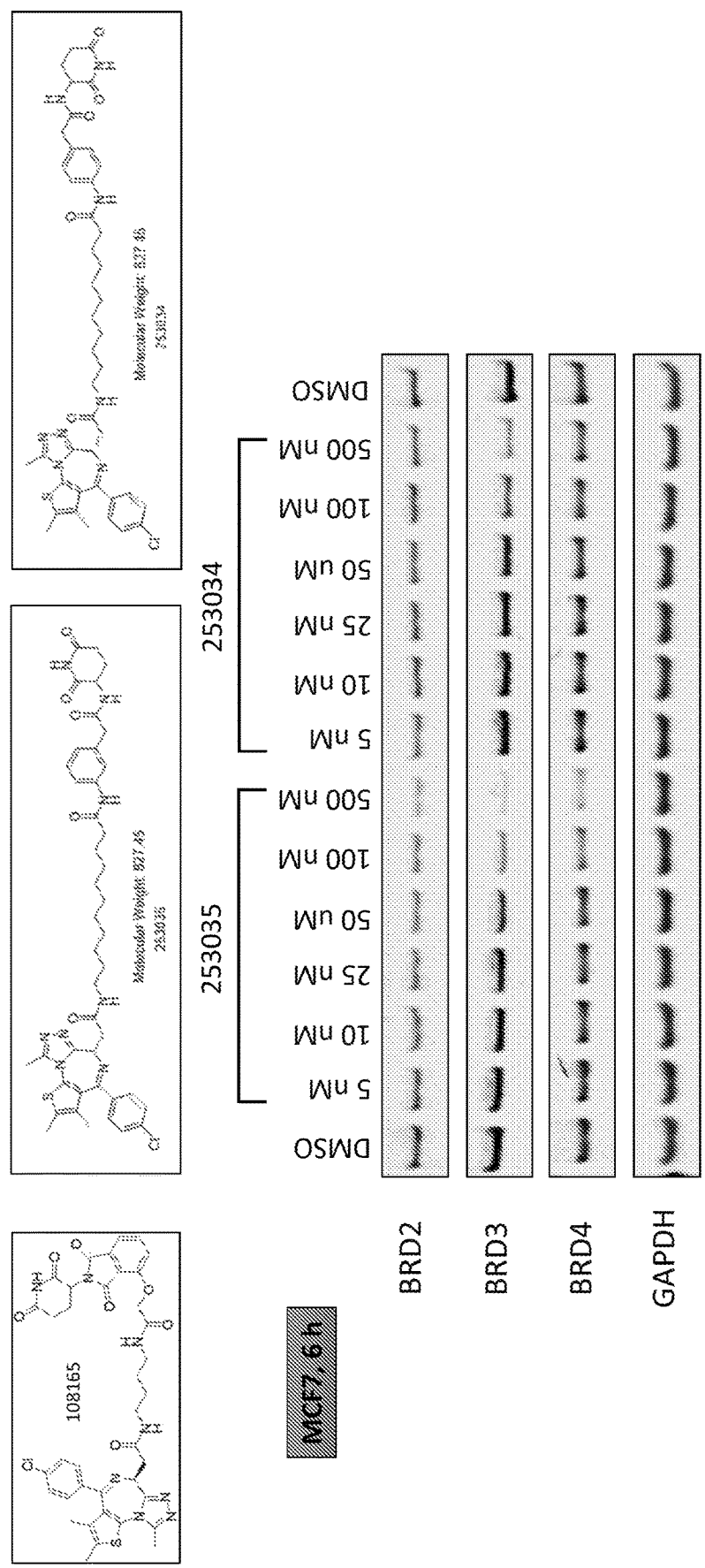
Figure 1C:
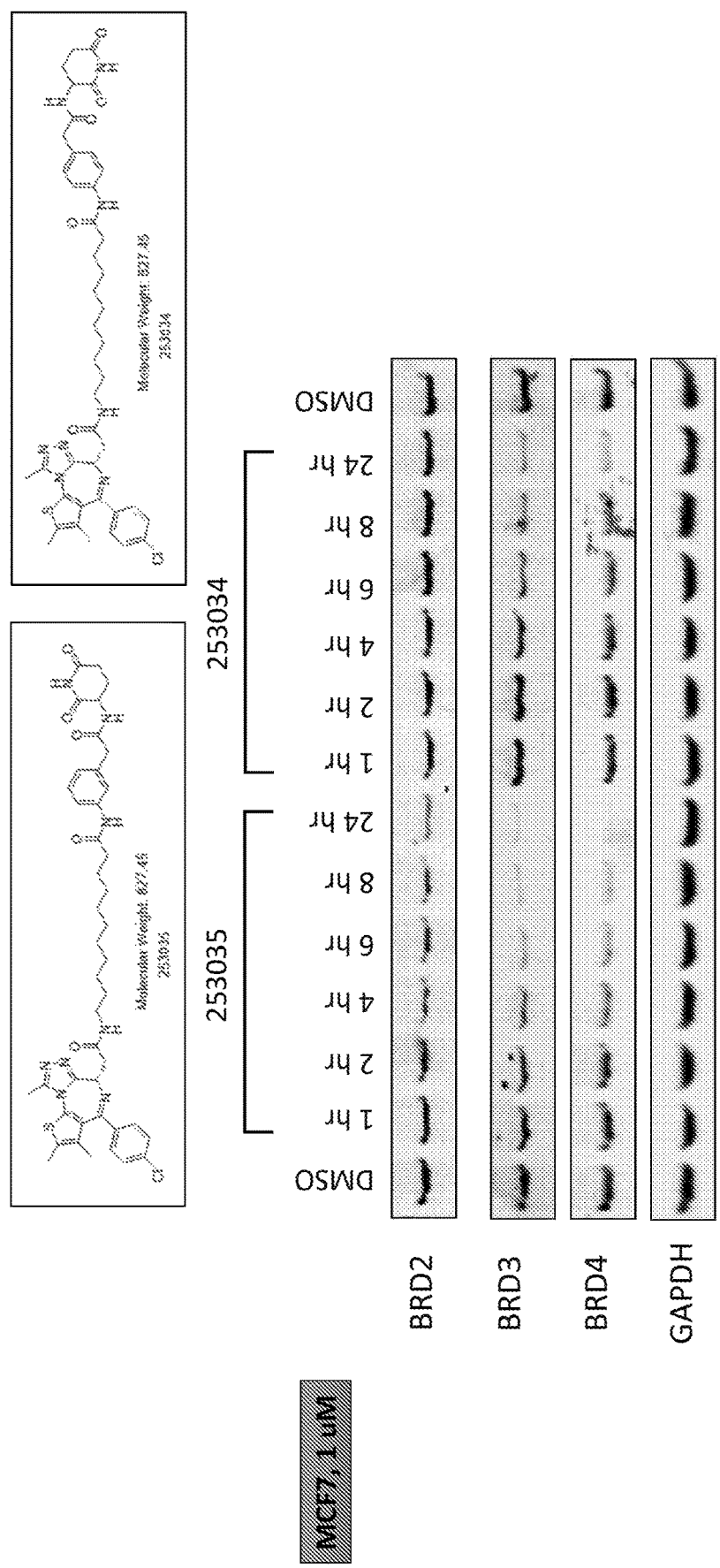
FIG. 1c illustrates the degradative activity of exemplary compounds 253035 and 253034 towards BRD2, BRD3, and BRD4 over a 24-hour time course experiment.

FIG. 1a and FIG. 1b illustrate the degradative activity of exemplary compounds 253035 and 253034 towards BRD2, BRD3 and BRD4 in a MCF7 cell line 6 hours after administration. 108165 (dBET1) is used as a positive control for BET degradative activity. FIG. 1c illustrates the degradative activity of exemplary compounds 253035 and 253034 towards BRD2, BRD3, and BRD4 over a 24 hour time course experiment.

Figure 2:
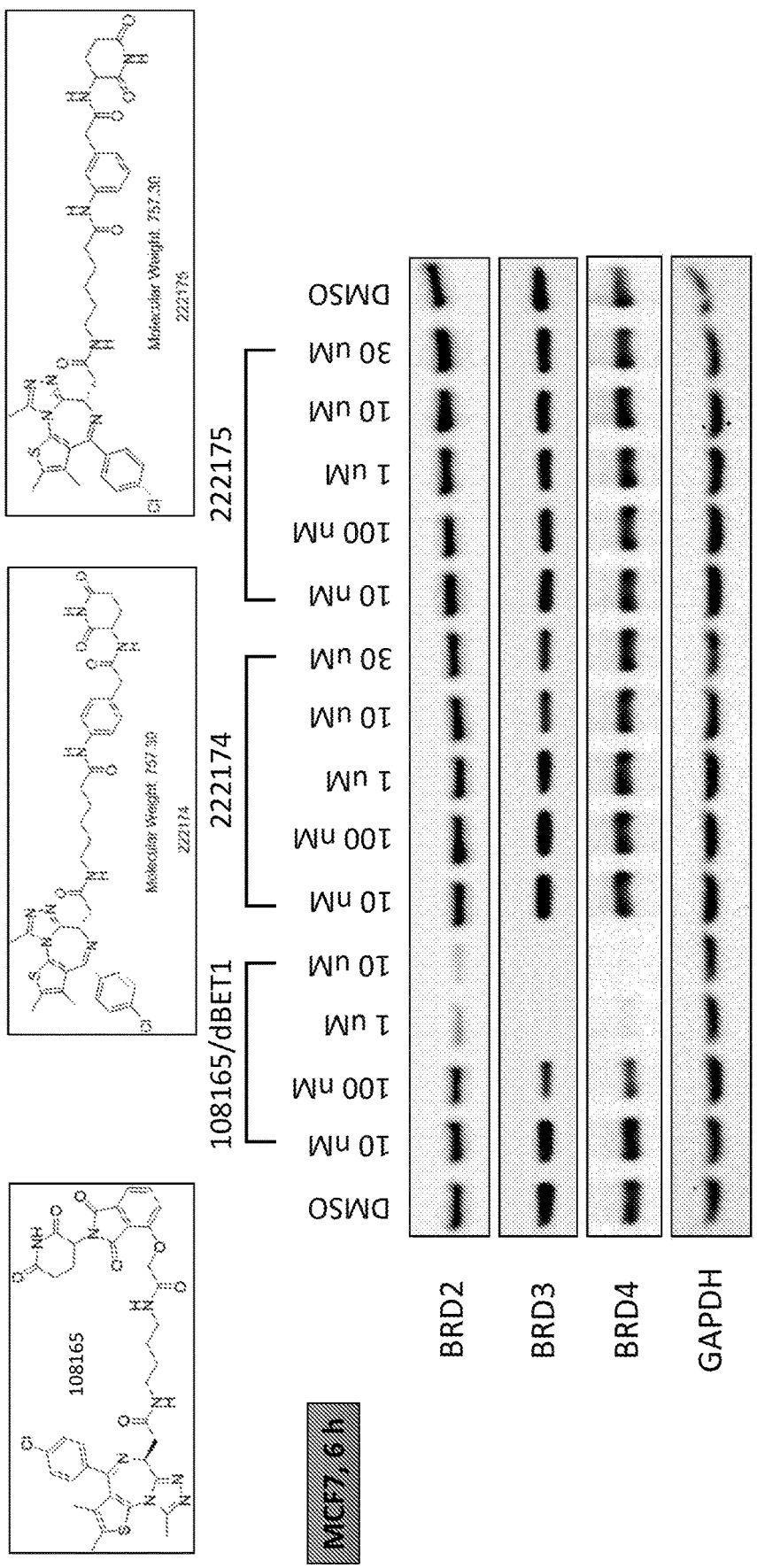
FIG. 2 illustrates the degradative activity of exemplary compounds 222174 and 222175 of the present disclosure towards BRD2, BRD3 and BRD4 in a MCF7 cell line 6 hours after administration. 108165 (dBET1) was used as a positive control for BET degradative activity.

FIG. 2 illustrates the degradative activity of exemplary compounds 22174 and 22175 of the present disclosure towards BRD2, BRD3 and BRD4 in a MCF7 cell line 6 hours after administration. 108165 (dBET1) is used as a positive control for BET degradative activity.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)amino)-2-oxoethyl) phenyl)undecanamide;

11-(2-((S)-4-(4-chlorophenyl)-2,3,9-trimethyl-6H-thieno[3,2-f][1,2,4]triazolo[4,3-a][1,4]diazepin-6-yl)acetamido)-N-(4-(2-((2,6-dioxopiperidin-3-yl)amino)-2-oxoethyl) phenyl)undecanamide;

7-(2-((S)-4-(4-chlorophenyl)-2,3,9-trimethyl-6H-thieno[3,2-f][1,2,4]triazolo[4,3-a][1,4]diazepin-6-yl)acetamido)-N-(4-(2-((2,6-dioxopiperidin-3-yl)amino)-2-oxoethyl) phenyl)heptanamide; and 6-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)amino)-2-oxoethyl) phenyl)hexanamide.

In some embodiments, provided herein is a compound of Formula (I), (Ia), (In), or (Ic), or a tautomer, stereoisomer, pharmaceutically acceptable salt or hydrate thereof.

In some embodiments, provided herein is a compound, or pharmaceutically acceptable salt thereof, chosen from the compounds listed in Table 1.

Pharmaceutical Compositions

Pharmaceutical compositions of the present disclosure comprise at least one compound of Formulae (I), (Ia), (Ib), or (Ic), or tautomer, stereoisomer, pharmaceutically acceptable salt or hydrate thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

What is claimed is:

1. A compound of Formula (I) or a pharmaceutically acceptable salt thereof:

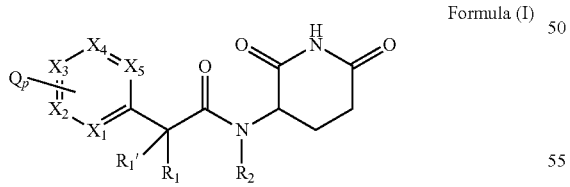

Formula (I)

wherein:
X$^1$, X$^2$, X$^3$, X$^4$, and X$^5$ are independently selected from C-Q, CH, and N;
R$^1$, R$^{1'}$ and R$^2$ are independently selected from H, C$_1$-C$_6$ alkyl, C$_3$-C$_6$ cycloalkyl, aryl, halo, hydroxy, and sulfhydryl, each of which is substituted with 0, 1, 2, or 3 R$^4$, wherein R$^1$ and R$^{1'}$ can be connected to form a 3 to 6 member heterocyclic or heteroaryl ring, and R$^1$ and R$^2$ can be connected to form a 5 to 7 member heterocyclic or heteroaryl ring;

Q is

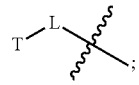

p is 1;
L is a linker of 1 to 22 carbon atoms in length, wherein one or more carbon atoms are each optionally and independently replaced by a group selected from C(O), O, NR$^3$, S, SO, SO$_2$, C$_2$-alkenyl, C$_2$-alkynyl, cycloalkyl, aryl, heterocycle, and heteroaryl, each of which can be substituted with 0, 1, 2, or 3 R$^4$;
T is a targeting ligand;
R$^3$ is independently selected from H, C$_1$-C$_6$ alkyl, aryl, heteroaryl, and acyl, where acyl can contain C$_1$-C$_6$ alkyl, C$_1$-C$_6$ cycloalkyl, aryl and heteroaryl, each of which can be substituted with 0, 1, 2, or 3 R$^4$; and
each R$^4$ is independently selected from C$_1$-C$_6$ alkyl, halo, cyano, and hydroxyl.

2. The compound according to claim 1, wherein the compound is a compound of Formula (Ia):

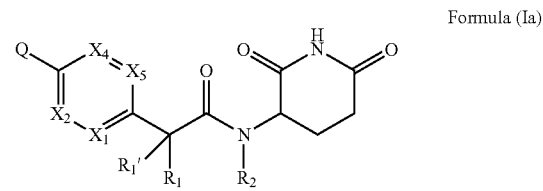

Formula (Ia)

wherein:
X$^1$, X$^2$, X$^4$, and X$^5$ are independently selected from CH and N;
R$^1$, R$^{1'}$ and R$^2$ are independently selected from H, C$_1$-C$_6$ alkyl, C$_3$-C$_6$ cycloalkyl, aryl, halo, hydroxy, and sulfhydryl, each of which is substituted with 0, 1, 2, or 3 R$^4$, wherein R$^1$ and R$^{1'}$ can be connected to form a 3 to 6 member heterocyclic or heteroaryl ring, and R$^1$ and R$^2$ can be connected to form 5 to 7 member heterocyclic or heteroaryl ring;
Q is

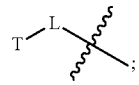

L is a linker of 1 to 22 carbon atoms in length, wherein one or more carbon atoms are each optionally and independently replaced by a group selected from C(O), O, NR$^3$, S, SO, SO$_2$, C$_2$-alkenyl, C$_2$-alkynyl, cycloalkyl, aryl, heterocycle, and heteroaryl, each of which can be substituted with 0, 1, 2, or 3 R$^4$;
T is a targeting ligand;
R$^3$ is independently selected from H, C$_1$-C$_6$ alkyl, aryl, heteroaryl, and acyl, where acyl can contain C$_1$-C$_6$ alkyl, C$_1$-C$_6$ cycloalkyl, aryl and heteroaryl, each of which can be substituted with 0, 1, 2, or 3 R$^4$; and
each R$^4$ is independently selected from C$_1$-C$_6$ alkyl, halo, cyano, and hydroxyl.

3. The compound according to claim 1, wherein the compound is a compound of Formula (Ib):

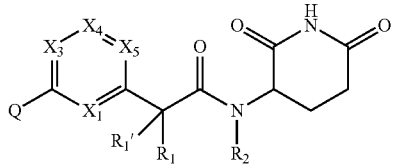

Formula (Ib)

wherein:
$X^1$, $X^3$, $X^4$, and $X^5$ are independently selected from CH and N;
$R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form 5 to 7 member heterocyclic or heteroaryl ring;
Q is

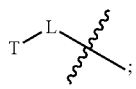

L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;
T is a targeting ligand;
$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and
each $R^4$ is independently selected from $C_1$-$C_6$ alkyl, halo, cyano, and hydroxyl.

4. The compound according to claim 1, wherein the compound is a compound of Formula (Ic):

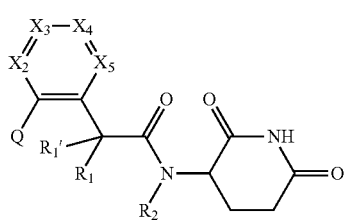

Formula (Ic)

wherein:
$X^2$, $X^3$, $X^4$, and $X^5$ are independently selected from CH and N;
$R^1$, $R^{1'}$ and $R^2$ are independently selected from H, $C_1$-$C_6$ alkyl, $C_3$-$C_6$ cycloalkyl, aryl, halo, hydroxy, and sulfhydryl, each of which is substituted with 0, 1, 2, or 3 $R^4$, wherein $R^1$ and $R^{1'}$ can be connected to form a 3 to 6 member heterocyclic or heteroaryl ring, and $R^1$ and $R^2$ can be connected to form 5 to 7 member heterocyclic or heteroaryl ring;

Q is

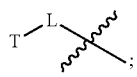

L is a linker of 1 to 22 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which can be substituted with 0, 1, 2, or 3 $R^4$;
T is a targeting ligand;
$R^3$ is independently selected from H, $C_1$-$C_6$ alkyl, aryl, heteroaryl, and acyl, where acyl can contain $C_1$-$C_6$ alkyl, $C_1$-$C_6$ cycloalkyl, aryl and heteroaryl, each of which can be substituted with 0, 1, 2, or 3 $R^4$; and
each $R^4$ is independently selected from $C_1$-$C_6$ alkyl, halo, cyano, and hydroxyl.

5. The compound according to claim 1, wherein $R^1$, $R^{1'}$ and $R^2$ are each independently selected from H, C, alkyl, $C_3$ cycloalkyl, halo, and hydroxy, each of which may be substituted with 0, 1, 2, or 3 $R^4$.

6. The compound according to claim 1, wherein $X^1$ is N and $X^2$, $X^3$, $X^4$, and $X^5$ are C-Q or CH.

7. The compound according to claim 1, wherein $X^4$ is N, and $X^2$, $X^3$, and $X^5$ are CH.

8. The compound according to claim 1, wherein L is a linker of 1 to 16 carbon atoms in length, wherein one or more carbon atoms are each optionally and independently replaced by a group selected from C(O), O, $NR^3$, S, SO, $SO_2$, $C_2$-alkenyl, $C_2$-alkynyl, cycloalkyl, aryl, heterocycle, and heteroaryl, each of which is independently substituted with 0, 1, 2, or 3 $R^4$.

9. The compound according to claim 1, wherein L is a linker with one or more carbon atoms, wherein the one or more carbon atoms is each independently replaced by a group selected from C(O), O, $NR^3$, $C_2$-alkynyl, and heterocycle, each of which is independently substituted with 0, 1, 2, or 3 $R^4$.

10. The compound according to claim 1, wherein $R^3$ is independently selected from H and $C_1$-$C_6$ alkyl.

11. The compound according to claim 1, wherein L is selected from

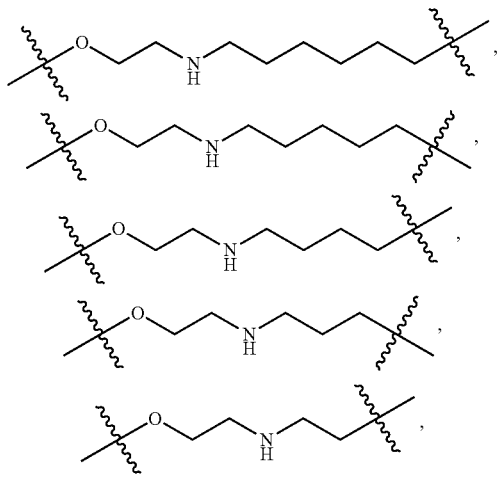

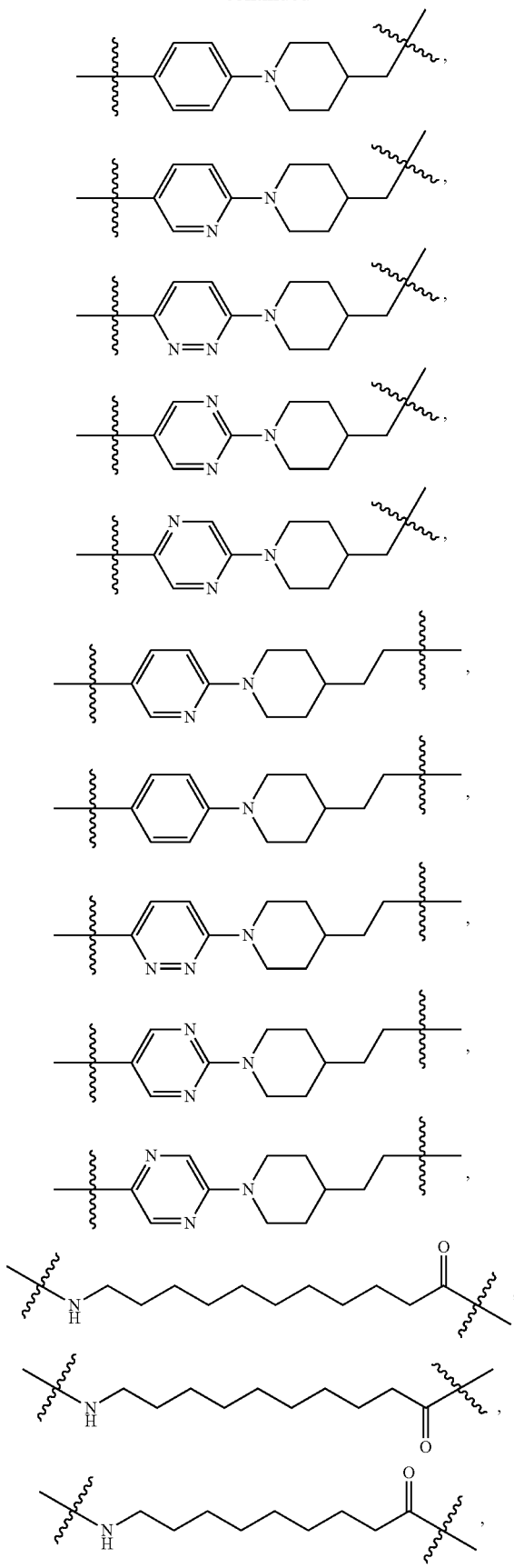
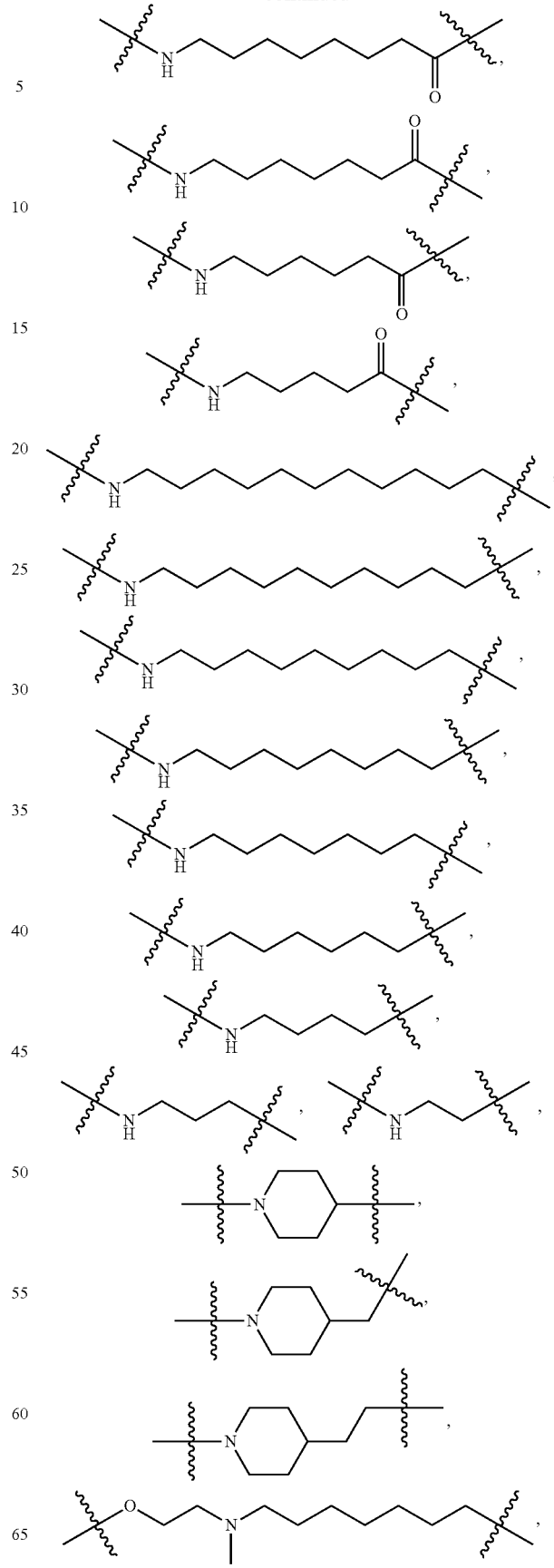

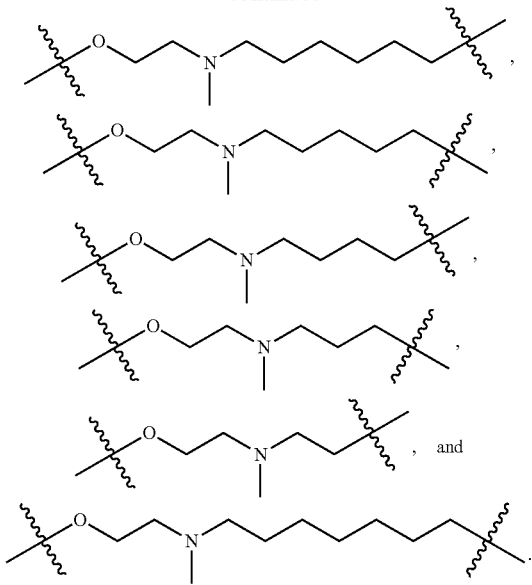

12. The compound according to claim 1, wherein L is

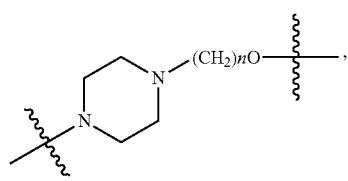

wherein n is 2 to 8.

13. The compound according to claim 1, wherein the targeting ligand binds to a target protein selected from a protein containing a BET domain, an Estrogen Receptor (ER), and an Androgen Receptor (AR).

14. The compound according to claim 13, wherein the targeting ligand is a compound of Formula (II):

Formula (II)

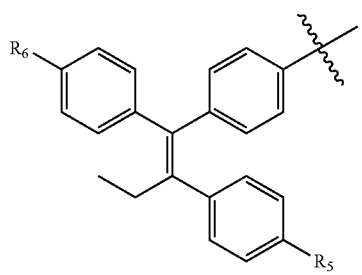

wherein:

$R^5$ is selected from H, $C_1$-$C_6$ alkyl, halo, hydroxy, and sulfhydryl, each of which is substituted with 0, 1, 2, or 3 $R^8$;

$R^6$ is selected from H, OH, $C_1$-$C_6$ alkyl, and acyl, each of which is substituted with 0, 1, 2, or 3 $R^8$;

each $R^8$ is independently selected from $C_1$-$C_6$ alkyl, halo, cyano, and hydroxy; and wherein

is a bond to L.

15. The compound according to claim 13, wherein the targeting ligand binds BRD2, BRD3, BRD4 or BRDT.

16. The compound according to claim 15, wherein the targeting ligand is a compound of Formula (III):

Formula (III)

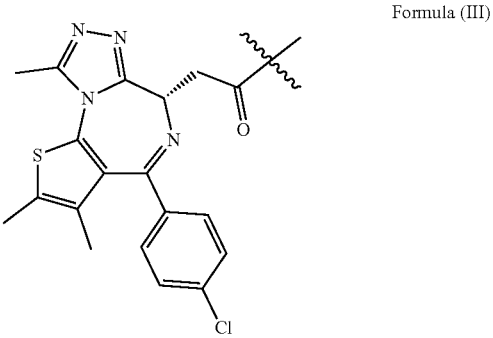 [SMILES: *C(=O)C[C@@H]1N=C(c2ccc(Cl)cc2)c2c(sc(C)c2C)-n2c(C)nnc21]

wherein

is a bond to L.

17. The compound according to claim 13, wherein the target protein is an androgen receptor.

18. The compound according to claim 17, wherein the targeting ligand is a compound of Formula (IV):

Formula (IV)

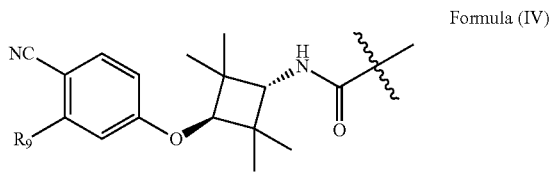

wherein $R^9$ is selected from Cl, $CH_3$, $CF_3$, and $OCH_3$, and wherein

is a bond to L.

19. The compound according to claim 17, wherein the targeting ligand is a compound of Formula (V):

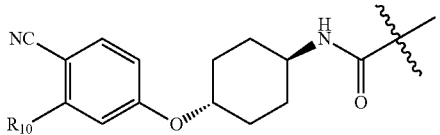

Formula (V)

wherein R$^{10}$ is selected from Cl, CH$_3$, CF$_3$, and OCH$_3$; and wherein

is a bond to L.

20. The compound according to claim 17, wherein the targeting ligand is a compound of Formula (VI):

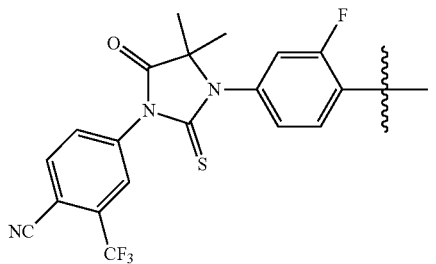

Formula (VI)

wherein

is a bond to L.

21. The compound according to claim 17, wherein the targeting ligand is a compound of Formula (VII):

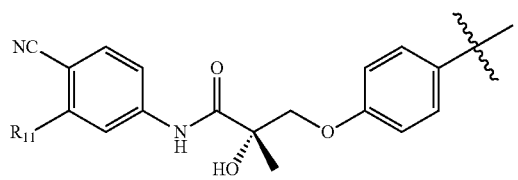

Formula (VII)

wherein R$^{11}$ is selected from Cl, CH$_3$, CF$_3$, and OCH$_3$; and wherein

is a bond to L.

22. The compound according to claim 1, wherein the compound is selected from:

N-((1r,4r)-4-(3-chloro-4-cyanophenoxy)cyclohexyl)-6-(4-((4-(3-(2-((2,6-dioxopiperidin-3-yl)(methyl)amino)-2-oxoethyl)phenyl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)(methyl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(2-(2-((2,6-dioxopiperidin-3-yl)(methyl)amino)-2-oxoethyl)pyridin-4-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)(methyl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)amino)-2-oxoethyl)phenyl)piperazin-1-yl)methyl)piperidin-1-yl)pyridazine-3-carboxamide;

N-((1r,4r)-4-(3-chloro-4-cyanophenoxy)cyclohexyl)-6-(4-((4-(4-(2-((2,6-dioxopiperidin-3-yl)(methyl)amino)-2-oxoethyl)phenyl)piperazin-1-yl)methyl)piperidin-1-yl)pyridazine-3-carboxamide;

N-((1r,4r)-4-(3-chloro-4-cyanophenoxy)cyclohexyl)-6-(4-((4-(5-(2-((2,6-dioxopiperidin-3-yl)(methyl)amino)-2-oxoethyl)pyridin-2-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)(methyl)amino)-2-oxoethyl)pyridin-3-yl)piperazin-1-yl)methyl)piperidin-1-yl)pyridazine-3-carboxamide;

N-((1r,4r)-4-(3-chloro-4-cyanophenoxy)cyclohexyl)-6-(4-((4-(6-(2-((2,6-dioxopiperidin-3-yl)amino)-2-oxoethyl)pyridin-3-yl)piperazin-1-yl)methyl)piperidin-1-yl)pyridazine-3-carboxamide;

(2S)—N-(4-cyano-3-(trifluoromethyl)phenyl)-3-(4-(4-(2-(4-(3-(2-((2,6-dioxopiperidin-3-yl)(methyl)amino)-2-oxoethyl)phenyl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(5-(2-((2,6-dioxopiperidin-3-yl)(methyl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(4-(2-((2,6-dioxopiperidin-3-yl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(2-(2-((2,6-dioxopiperidin-3-yl)(methyl)amino)-2- oxoethyl)pyridin-4-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(6-(2-((2,6-dioxopiperidin-3-yl)(methyl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(6-(2-((2,6-dioxopiperidin-3-yl)amino)-2-oxoethyl)pyridin-2-yl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(4-(2-((2,6-dioxopiperidin-3-yl)amino)-2-oxoethyl)phenyl)piperazin-1-yl)ethyl)piperazin-1-yl)phenoxy)-2-hydroxy-2-methylpropanamide;

(2S)—N-(4-cyano-3-(trifluoromethyl)phenyl)-3-(4-(4-(2-(4-(4-(2-((2,6-dioxopiperidin-3-yl)(methyl)amino)-2-oxoethyl)phenyl)piperazin-1-yl)ethyl)piperazin-1-yl)phenoxy)-2-hydroxy-2-methylpropanamide;

N-(4-cyano-3-(trifluoromethyl)phenyl)-3-(4-(4-(3-(4-(2-((2,6-dioxopiperidin-3-yl)(methyl)amino)-2-oxoethyl)phenoxy)propyl)piperazin-1-yl)phenoxy)-2-hydroxy-2-methylpropanamide;

N-(4-cyano-3-(trifluoromethyl)phenyl)-3-(4-(4-(3-(4-(2-((2,6-dioxopiperidin-3-yl)amino)-2-oxoethyl)phenoxy)propyl)piperazin-1-yl)phenoxy)-2-hydroxy-2-methylpropanamide;

N-(4-cyano-3-(trifluoromethyl)phenyl)-3-(4-((4-(3-(3-(2-((2,6-dioxopiperidin-3-yl)amino)-2-oxoethyl)phenoxy)propyl)piperazin-1-yl)methyl)phenoxy)-2-hydroxy-2-methylpropanamide;

N-(4-cyano-3-(trifluoromethyl)phenyl)-3-(4-((4-(3-(3-(2-((2,6-dioxopiperidin-3-yl)(methyl)amino)-2-oxoethyl)phenoxy)propyl)piperazin-1-yl)methyl)phenoxy)-2-hydroxy-2-methylpropanamide;

N-(4-(3-((4-cyano-3-(trifluoromethyl)phenyl)amino)-2-hydroxy-2-methyl-3-oxopropoxy)benzyl)-5-(4-(4-(2-((2,6-dioxopiperidin-3-yl)amino)-2-oxoethyl)pyridin-2-yl)piperazin-1-yl)pentanamide;

N-(4-(3-((4-cyano-3-(trifluoromethyl)phenyl)amino)-2-hydroxy-2-methyl-3-oxopropoxy)benzyl)-5-(4-(4-(2-((2,6-dioxopiperidin-3-yl)(methyl)amino)-2-oxoethyl)pyridin-2-yl)piperazin-1-yl)pentanamide;

N-(4-((S)-3-((4-cyano-3-(trifluoromethyl)phenyl)amino)-2-hydroxy-2-methyl-3-oxopropoxy)benzyl)-4-(4-(4-(2-((2,6-dioxopiperidin-3-yl)amino)-2-oxoethyl)pyridin-2-yl)piperazin-1-yl)butanamide; and N-(4-((S)-3-((4-cyano-3-(trifluoromethyl)phenyl)amino)-2-hydroxy-2-methyl-3-oxopropoxy)benzyl)-4-(4-(4-(2-((2,6-dioxopiperidin-3-yl)(methyl)amino)-2-oxoethyl)pyridin-2-yl)piperazin-1-yl)butanamide.

23. The compound according to claim 1, wherein the compound is selected from:

2-((S)-4-(4-chlorophenyl)-2,3,9-trimethyl-6H-thieno[3,2-f][1,2,4]triazolo[4,3-a][1,4]diazepin-6-yl)-N-(2-(4-(3-(2-((2,6-dioxopiperidin-3-yl)amino)-2-oxoethyl)phenyl)piperazin-1-yl)ethyl)acetamide;

2-((S)-4-(4-chlorophenyl)-2,3,9-trimethyl-6H-thieno[3,2-f][1,2,4]triazolo[4,3-a][1,4]diazepin-6-yl)-N-(3-(4-(3-(2-((2,6-dioxopiperidin-3-yl)amino)-2-oxoethyl)phenyl)piperazin-1-yl)propyl)acetamide;

2-((S)-4-(4-chlorophenyl)-2,3,9-trimethyl-6H-thieno[3,2-f][1,2,4]triazolo[4,3-a][1,4]diazepin-6-yl)-N-(4-(4-(3-(2-((2,6-dioxopiperidin-3-yl)amino)-2-oxoethyl)phenyl)piperazin-1-yl)butyl)acetamide;

2-((S)-4-(4-chlorophenyl)-2,3,9-trimethyl-6H-thieno[3,2-f][1,2,4]triazolo[4,3-a][1,4]diazepin-6-yl)-N-(5-(4-(3-(2-((2,6-dioxopiperidin-3-yl)amino)-2-oxoethyl)phenyl)piperazin-1-yl)pentyl)acetamide;

2-((S)-4-(4-chlorophenyl)-2,3,9-trimethyl-6H-thieno[3,2-f][1,2,4]triazolo[4,3-a][1,4]diazepin-6-yl)-N-(6-(4-(3-(2-((2,6-dioxopiperidin-3-yl)amino)-2-oxoethyl)phenyl)piperazin-1-yl)hexyl)acetamide;

2-((S)-4-(4-chlorophenyl)-2,3,9-trimethyl-6H-thieno[3,2-f][1,2,4]triazolo[4,3-a][1,4]diazepin-6-yl)-N-(7-(4-(3-(2-((2,6-dioxopiperidin-3-yl)amino)-2-oxoethyl)phenyl)piperazin-1-yl)heptyl)acetamide;

2-((S)-4-(4-chlorophenyl)-2,3,9-trimethyl-6H-thieno[3,2-f][1,2,4]triazolo[4,3-a][1,4]diazepin-6-yl)-N-(8-(4-(3-(2-((2,6-dioxopiperidin-3-yl)amino)-2-oxoethyl)phenyl)piperazin-1-yl)octyl)acetamide;

2-((S)-4-(4-chlorophenyl)-2,3,9-trimethyl-6H-thieno[3,2-f][1,2,4]triazolo[4,3-a][1,4]diazepin-6-yl)-N-(9-(4-(3-(2-((2,6-dioxopiperidin-3-yl)amino)-2-oxoethyl)phenyl)piperazin-1-yl)nonyl)acetamide;

11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)(methyl)amino)-2-oxoethyl)phenyl)undecanamide;

2-((S)-4-(4-chlorophenyl)-2,3,9-trimethyl-6H-thieno[3,2-f][1,2,4]triazolo[4,3-a][1,4]diazepin-6-yl)-N-(8-(4-(2-((2,6-dioxopiperidin-3-yl)amino)-2-oxoethyl)phenyl)piperazin-1-yl)octyl)acetamide;

2-((S)-4-(4-chlorophenyl)-2,3,9-trimethyl-6H-thieno[3,2-f][1,2,4]triazolo[4,3-a][1,4]diazepin-6-yl)-N-(7-(4-(4-(2-((2,6-dioxopiperidin-3-yl)amino)-2-oxoethyl)phenyl)piperazin-1-yl)heptyl)acetamide;

11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-((2S)-1-((2,6-dioxopiperidin-3-yl)amino)-1-oxopropan-2-yl)phenyl)undecanamide;

11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-((2R)-1-((2,6-dioxopiperidin-3-yl)amino)-1-oxopropan-2-yl)phenyl)undecanamide;

1-(3-(11-(2-((S)-4-(4-chlorophenyl)-2,3,9-trimethyl-6H-thieno[3,2-f][1,2,4]triazolo[4,3-a][1,4]diazepin-6-yl)acetamido)undecanamido)phenyl)-N-(2,6-dioxopiperidin-3-yl)cyclopropane-1-carboxamide;

2-((S)-4-(4-chlorophenyl)-2,3,9-trimethyl-6H-thieno[3,2-f][1,2,4]triazolo[4,3-a][1,4]diazepin-6-yl)-N-(8-(4-(4-(2-((2,6-dioxopiperidin-3-yl)amino)-2-oxoethyl)pyridin-2-yl)piperazin-1-yl)octyl)acetamide 2-(2-(4-(8-(2-((S)-4-(4-chlorophenyl)-2,3,9-trimethyl-6H-thieno[3,2-f][1,2,4]triazolo[4,3-a][1,4]diazepin-6-yl)acetamido)octyl)piperazin-1-yl)pyridin-4-yl)-N-(2,6-dioxopiperidin-3-yl)-N-methylacetamide;

11-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)amino)-2-oxoethyl)phenyl)undecanamide;

6-(2-((S)-4-(4-chlorophenyl)-2,3,9-trimethyl-6H-thieno[3,2-f][1,2,4]triazolo[4,3-a][1,4]diazepin-6-yl)acetamido)-N-(4-(2-((2,6-dioxopiperidin-3-yl)amino)-2-oxoethyl)phenyl)hexanamide;

6-(2-((S)-4-(4-chlorophenyl)-2,3,9-trimethyl-6H-thieno[3,2-f][1,2,4]triazolo[4,3-a][1,4]diazepin-6-yl)acetamido)-N-(3-(2-((2,6-dioxopiperidin-3-yl)amino)-2-oxoethyl)phenyl)hexanamide; and 11-(2-((S)-4-(4-chlorophenyl)-2,3,9-trimethyl-6H-thieno[3,2-f][1,2,4]triazolo[4,3-a][1,4]diazepin-6-yl)acetamido)-N-(4-(2-((2,6-dioxopiperidin-3-yl)amino)-2-oxoethyl)phenyl)undecanamide.

24. The compound according to claim 1, wherein the compound is selected from:

(E)-N-(2,6-dioxopiperidin-3-yl)-2-(3-(4-((1-(4-(1-(4-hydroxyphenyl)-2-phenylbut-1-en-1-yl)phenyl)piperidin-4-yl)methyl)piperazin-1-yl)phenyl)-N-methylacetamide;

(E)-N-(2,6-dioxopiperidin-3-yl)-2-(2-(4-((1-(4-(1-(4-hydroxyphenyl)-2-phenylbut-1-en-1-yl)phenyl)piperidin-4-yl)methyl)piperazin-1-yl)pyridin-4-yl)-N-methylacetamide;

(E)-N-(2,6-dioxopiperidin-3-yl)-2-(2-(4-((1-(4-(1-(4-hydroxyphenyl)-2-phenylbut-1-en-1-yl)phenyl)piperidin-4-yl)methyl)piperazin-1-yl)pyridin-4-yl)acetamide;

(E)-N-(2,6-dioxopiperidin-3-yl)-2-(4-(4-((1-(4-(1-(4-hydroxyphenyl)-2-phenylbut-1-en-1-yl)phenyl)piperidin-4-yl)methyl)piperazin-1-yl)pyridin-2-yl)-N-methylacetamide;

(E)-N-(2,6-dioxopiperidin-3-yl)-2-(6-(4-((1-(4-(1-(4-hydroxyphenyl)-2-phenylbut-1-en-1-yl)phenyl)piperidin-4-yl)methyl)piperazin-1-yl)pyridin-2-yl)-N-methylacetamide;

(E)-N-(2,6-dioxopiperidin-3-yl)-2-(6-(4-((1-(4-(1-(4-hydroxyphenyl)-2-phenylbut-1-en-1-yl)phenyl)piperidin-4-yl)methyl)piperazin-1-yl)pyridin-2-yl)acetamide;

(E)-N-(2,6-dioxopiperidin-3-yl)-2-(4-(4-((1-(4-(1-(4-hydroxyphenyl)-2-phenylbut-1-en-1-yl)phenyl)piperidin-4-yl)methyl)piperazin-1-yl)phenyl)acetamide;

(E)-N-(2,6-dioxopiperidin-3-yl)-2-(4-(4-((1-(4-(1-(4-hydroxyphenyl)-2-phenylbut-1-en-1-yl)phenyl)piperidin-4-yl)methyl)piperazin-1-yl)phenyl)-N-methylacetamide;

(E)-N-(2,6-dioxopiperidin-3-yl)-2-(6-(4-((1-(4-(1-(4-hydroxyphenyl)-2-phenylbut-1-en-1-yl)phenyl)piperidin-4-yl)methyl)piperazin-1-yl)pyridin-3-yl)-N-methylacetamide;

(E)-N-(2,6-dioxopiperidin-3-yl)-2-(5-(4-((1-(4-(1-(4-hydroxyphenyl)-2-phenylbut-1-en-1-yl)phenyl)piperidin-4-yl)methyl)piperazin-1-yl)pyridin-2-yl)-N-methylacetamide;

(E)-N-(2,6-dioxopiperidin-3-yl)-2-(3-(4-((1-(4-(1-(4-hydroxyphenyl)-2-phenylbut-1-en-1-yl)phenyl)piperidin-4-yl)methyl)piperazin-1-yl)phenyl)acetamide; and (E)-N-(2,6-dioxopiperidin-3-yl)-2-(2-(4-(2-(1-(4-(1-(4-hydroxyphenyl)-2-phenylbut-1-en-1-yl)phenyl)piperidin-4-yl)ethyl)piperazin-1-yl)pyridin-4-yl)acetamide.

25. The compound according to claim 1, wherein at least one of $X^1$, $X^2$, $X^3$, $X^4$, or $X^5$ is N, or $R^{1'}$ or $R^1$ is not H.

26. A pharmaceutical composition comprising the compound according to claim 1 and at least one additional component selected from pharmaceutically acceptable carriers, pharmaceutically acceptable vehicles, and pharmaceutically acceptable excipients.

27. A method of treating abnormal cellular proliferation, a tumor, cancer, an immune disorder, autoimmune disorder, arthritis, lupus, diabetes, cardiovascular disease, an infectious disease, sepsis, or an inflammatory condition in a subject in need thereof, comprising administering to said subject an effective amount of the compound according to claim 1.

28. A method of treating abnormal cellular proliferation, a tumor, cancer, an immune disorder, autoimmune disorder, arthritis, lupus, diabetes, cardiovascular disease, an infectious disease, sepsis, or an inflammatory condition in a subject in need thereof, comprising administering to said subject an effective amount of the pharmaceutical composition of claim 26.

29. The method of claim 27, wherein the infectious disease is HIV, HBV, HCV, HSV, HPV, RSV, CMV, Ebola, Flavivirus, Pestivirus, Rotavirus, Influenza, Coronavirus, EBV, viral pneumonia, drug-resistant viruses, bird flu, RNA virus, DNA virus, adenovirus, poxvirus, meningitis, Picornavirus, Togavirus, Orthomyxovirus, Retrovirus, Hepadnovirus, Gram-negative bacteria, Gram-positive bacteria, Atypical bacteria, *Staphylococcus, Streptococcus, E. coli, Salmonella, Helicobacter pylori*, gonorrhea, Chlamydiaceae, Mycoplasmataceae, fungus, protozoa helminth, worms, or parasite.

30. The method according to claim 27, wherein the cancer is selected from melanoma, breast cancer, prostate cancer, lung cancer, neuroblastoma, glioblastoma, hematologic malignancy, squamous-cell carcinoma, NUT carcinoma, basal cell carcinoma, adenocarcinoma, bladder cancer, bowel cancer, cervical cancer, colon cancer, esophageal cancer, head and neck cancer, kidney cancer, renal cell carcinoma, liver, hepatocellular carcinoma, ovarian cancer, pancreatic cancer, stomach cancer, sarcoma, hemangiosarcoma, Kaposi's sarcoma, liposarcoma, myosarcoma, peripheral neuroepithelioma, synovial sarcoma, glioma, astrocytoma, oligodendroglioma, ependymoma, ganglioneuroma, ganglioglioma, medulloblastoma, pineal cell tumor, meningioma, meningeal sarcoma, neurofibroma, Schwannoma, uterine cancer, testicular cancer, thyroid cancer, carcinosarcoma, Wilms' tumor and teratocarcinoma.

31. The method according to claim 30, wherein the hematologic malignancy is lymphoma, multiple myeloma, leukemia, myelodysplastic syndrome, or myeloproliferative neoplasms.

32. The method according to claim 31, wherein the leukemia is acute myeloid leukemia, acute lymphoblastic leukemia, or chronic myeloid leukemia.

33. The method according to claim 31, wherein the lymphoma is large B-cell lymphoma, peripheral T cell lymphoma, Burkitt's Lymphoma, or Hodgkin's lymphoma.

34. The method according to claim 30, wherein the cancer is castrate-resistant prostate cancer, small cell lung cancer, non-small cell lung cancer, ER positive breast cancer, or triple negative breast cancer.

35. The method according to claim 27, wherein the subject has been previously treated with an anti-cancer agent, and wherein the anti-cancer agent is exemestane, fulvestrant, enzalutamide, a γ-secretase inhibitor, RAF-inhibitor, an aromatase inhibitor, a selective estrogen modulator (SERM), a selective estrogen receptor down regulator (SERD), luteinizing hormone-releasing hormone superagonists, CYP17 inhibitor Abiraterone, or a small molecule antagonist that blocks the androgen/AR interaction.

36. A method of inhibiting cell growth, comprising contacting a cell with the compound according to claim 1.

* * * * *